US 7,939,677 B2

(12) United States Patent  (10) Patent No.: US 7,939,677 B2
Bhat et al.  (45) Date of Patent: May 10, 2011

(54) OLIGOMERIC COMPOUNDS COMPRISING 4'-THIONUCLEOSIDES FOR USE IN GENE MODULATION

(75) Inventors: Balkrishen Bhat, Carlsbad, CA (US);
Prasad Dande, Chicago, IL (US);
Thazha P. Prakash, Carlsbad, CA (US);
Charles Allerson, San Diego, CA (US);
Eric E. Swayze, Encinitas, CA (US);
Richard H. Griffey, Vista, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/872,438

(22) Filed: Aug. 31, 2010

(65) Prior Publication Data

US 2010/0324277 A1    Dec. 23, 2010

Related U.S. Application Data

(62) Division of application No. 10/946,147, filed on Sep. 20, 2004.

(60) Provisional application No. 60/503,997, filed on Sep. 18, 2003.

(51) Int. Cl.
*C07D 409/04* (2006.01)

(52) U.S. Cl. ........................................ 549/59

(58) Field of Classification Search ............... 549/59
See application file for complete search history.

(56) References Cited

U.S. PATENT DOCUMENTS

| | | | |
|---|---|---|---|
| 3,687,808 A | 8/1972 | Merigan, Jr. | |
| 4,415,732 A | 11/1983 | Caruthers | |
| 4,458,066 A | 7/1984 | Caruthers | |
| 4,469,863 A | 9/1984 | Tso | |
| 4,476,301 A | 10/1984 | Imbach | |
| 4,500,707 A | 2/1985 | Caruthers | |
| 4,605,735 A | 8/1986 | Miyoshi | |
| 4,667,025 A | 5/1987 | Miyoshi | |
| 4,667,777 A | 5/1987 | Nomura | |
| 4,725,677 A | 2/1988 | Koster | |
| 4,762,779 A | 8/1988 | Snitman | |
| 4,789,737 A | 12/1988 | Miyoshi | |
| 4,824,941 A | 4/1989 | Gordon | |
| 4,828,979 A | 5/1989 | Klevan | |
| 4,835,263 A | 5/1989 | Nguyen | |
| 4,876,335 A | 10/1989 | Yamane | |
| 4,904,582 A | 2/1990 | Tullis | |
| 4,948,882 A | 8/1990 | Ruth | |
| 4,958,013 A | 9/1990 | Letsinger | |
| 4,973,679 A | 11/1990 | Caruthers | |
| 4,981,957 A | 1/1991 | Lebleu | |
| 5,013,830 A | 5/1991 | Ohtsuka | |

(Continued)

FOREIGN PATENT DOCUMENTS

EP    0421777    4/1991

(Continued)

OTHER PUBLICATIONS

U.S. Appl. No. 08/468,037, filed Jun. 5, 1995, Cook.

(Continued)

*Primary Examiner* — Taofiq A Solola

(74) *Attorney, Agent, or Firm* — Jones Day

(57) ABSTRACT

The present invention provides modified oligomeric compounds and compositions of oligomeric compounds for use in the RNA interference pathway of gene modulation. The modified oligomeric compounds include siRNA and asRNA having at least one affinity modification.

20 Claims, 2 Drawing Sheets

PTEN siRNA Constructs

| Alias Id | Notation | Equivalent Sequence | |
|---|---|---|---|
| 341401 | $A_{ro}A_{ro}G_{ro}U_{ro}A_{ro}A_{ro}G_{ro}G_{ro}A_{ro}C_{ro}C_{ro}A_{ro}G_{ro}A_{ro}G_{ro}A_{ro}C_{ro}A_{ro}A_{r}$ | AAGTAAGGACCAGAGACAA (Sense) | (SEQ ID NO: 8) |
| 341391 | $U_{ro}U_{ro}G_{ro}U_{ro}C_{ro}U_{ro}C_{ro}U_{ro}G_{ro}G_{ro}U_{ro}C_{ro}C_{ro}U_{ro}U_{ro}A_{ro}C_{ro}U_{ro}U_{r}$ | TTGTCTCTGGTCCTTACTT (Antisense) | (SEQ ID NO: 9) |
| 375761 | $U_{so}U_{so}G_{ro}U_{ro}C_{ro}U_{ro}C_{ro}U_{ro}G_{ro}G_{ro}U_{ro}C_{ro}C_{ro}U_{ro}U_{ro}A_{ro}C_{xo}U_{xo}U_{x}$ | TTGTCTCTGGTCCTTACTT (Antisense) | (SEQ ID NO: 9) |
| 375762 | $U_{ro}U_{ro}G_{mo}U_{ro}C_{ro}U_{ro}C_{ro}U_{xo}G_{ro}G_{ro}U_{ro}C_{ro}C_{xo}U_{ro}U_{ro}A_{ro}C_{ro}U_{xo}U_{r}$ | TTGTCTCTGGTCCTTACTT (Antisense) | (SEQ ID NO: 9) |

Key: o = phosphodiester linkage
r = ribose sugar;
s = 4'-thioribose sugar
m = 2'-O-methylribose sugar
x = 2'-O-methyl-4'-thioribose sugar

U.S. PATENT DOCUMENTS

| | | | |
|---|---|---|---|
| 5,023,243 A | 6/1991 | Tullis | |
| 5,034,506 A | 7/1991 | Summerton | |
| 5,082,830 A | 1/1992 | Brakel | |
| 5,109,124 A | 4/1992 | Ramachandran | |
| 5,112,963 A | 5/1992 | Pieles | |
| 5,118,800 A | 6/1992 | Smith | |
| 5,118,802 A | 6/1992 | Smith | |
| 5,130,302 A | 7/1992 | Spielvogel | |
| 5,132,418 A | 7/1992 | Caruthers | |
| 5,134,066 A | 7/1992 | Rogers | |
| RE34,036 E | 8/1992 | McGeehan | |
| 5,138,045 A | 8/1992 | Cook | |
| 5,149,797 A | 9/1992 | Pederson | |
| 5,166,315 A | 11/1992 | Summerton | |
| 5,175,273 A | 12/1992 | Bischofberger | |
| 5,177,196 A | 1/1993 | Meyer, Jr. | |
| 5,177,198 A | 1/1993 | Spielvogel | |
| 5,185,444 A | 2/1993 | Summerton | |
| 5,188,897 A | 2/1993 | Suhadolnik | |
| 5,194,599 A | 3/1993 | Froehler | |
| 5,214,134 A | 5/1993 | Weis | |
| 5,214,136 A | 5/1993 | Lin | |
| 5,216,141 A | 6/1993 | Benner | |
| 5,218,105 A | 6/1993 | Cook | |
| 5,220,007 A | 6/1993 | Pederson | |
| 5,223,618 A | 6/1993 | Cook | |
| 5,235,033 A | 8/1993 | Summerton | |
| 5,245,022 A | 9/1993 | Weis | |
| 5,254,469 A | 10/1993 | Warren | |
| 5,256,775 A | 10/1993 | Froehler | |
| 5,258,506 A | 11/1993 | Urdea | |
| 5,262,536 A | 11/1993 | Hobbs | |
| 5,264,423 A | 11/1993 | Cohen | |
| 5,264,562 A | 11/1993 | Matteucci | |
| 5,264,564 A | 11/1993 | Matteucci | |
| 5,272,250 A | 12/1993 | Spielvogel | |
| 5,276,019 A | 1/1994 | Cohen | |
| 5,278,302 A | 1/1994 | Caruthers | |
| 5,286,717 A | 2/1994 | Cohen | |
| 5,292,873 A | 3/1994 | Rokita | |
| 5,317,098 A | 5/1994 | Shizuya | |
| 5,319,080 A | 6/1994 | Leumann | |
| 5,321,131 A | 6/1994 | Agrawal | |
| 5,359,044 A | 10/1994 | Cook | |
| 5,366,878 A | 11/1994 | Pederson | |
| 5,367,066 A | 11/1994 | Urdea | |
| 5,371,241 A | 12/1994 | Brush | |
| 5,378,825 A | 1/1995 | Cook | |
| 5,386,023 A | 1/1995 | Sanghvi | |
| 5,391,723 A | 2/1995 | Priest | |
| 5,393,878 A | 2/1995 | Leumann | |
| 5,399,676 A | 3/1995 | Froehler | |
| 5,403,711 A | 4/1995 | Walder | |
| 5,405,938 A | 4/1995 | Summerton | |
| 5,405,939 A | 4/1995 | Suhadolnik | |
| 5,414,077 A | 5/1995 | Lin | |
| 5,416,203 A | 5/1995 | Letsinger | |
| 5,432,272 A | 7/1995 | Benner | |
| 5,434,257 A | 7/1995 | Matteucci | |
| 5,446,137 A | 8/1995 | Maag | |
| 5,451,463 A | 9/1995 | Nelson | |
| 5,453,496 A | 9/1995 | Caruthers | |
| 5,455,233 A | 10/1995 | Spielvogel | |
| 5,457,187 A | 10/1995 | Gmeiner | |
| 5,459,255 A | 10/1995 | Cook | |
| 5,466,677 A | 11/1995 | Baxter | |
| 5,466,786 A | 11/1995 | Buhr | |
| 5,470,967 A | 11/1995 | Huie | |
| 5,476,925 A | 12/1995 | Letsinger | |
| 5,484,908 A | 1/1996 | Froehler | |
| 5,486,603 A | 1/1996 | Buhr | |
| 5,487,044 A | 1/1996 | Kawaguchi | |
| 5,489,677 A | 2/1996 | Sanghvi | |
| 5,491,133 A | 2/1996 | Walder | |
| 5,502,177 A | 3/1996 | Matteucci | |
| 5,508,270 A | 4/1996 | Baxter | |
| 5,510,475 A | 4/1996 | Agrawal | |
| 5,512,439 A | 4/1996 | Hornes | |
| 5,512,667 A | 4/1996 | Reed | |
| 5,514,785 A | 5/1996 | Van Ness | |
| 5,519,126 A | 5/1996 | Hecht | |
| 5,519,134 A | 5/1996 | Acevedo | |
| 5,525,465 A | 6/1996 | Haralambidis | |
| 5,525,711 A | 6/1996 | Hawkins | |
| 5,527,899 A | 6/1996 | Froehler | |
| 5,536,821 A | 7/1996 | Agrawal | |
| 5,541,306 A | 7/1996 | Agrawal | |
| 5,541,307 A | 7/1996 | Cook | |
| 5,541,313 A | 7/1996 | Ruth | |
| 5,545,730 A | 8/1996 | Urdea | |
| 5,550,111 A | 8/1996 | Suhadolnik | |
| 5,552,538 A | 9/1996 | Urdea | |
| 5,552,540 A | 9/1996 | Haralambidis | |
| 5,561,225 A | 10/1996 | Maddry | |
| 5,563,253 A | 10/1996 | Agrawal | |
| 5,565,350 A | 10/1996 | Kmiec | |
| 5,565,552 A | 10/1996 | Magda | |
| 5,565,555 A | 10/1996 | Froehler | |
| 5,567,810 A | 10/1996 | Weis | |
| 5,567,811 A | 10/1996 | Misiura | |
| 5,571,799 A | 11/1996 | Tkachuk | |
| 5,574,142 A | 11/1996 | Meyer | |
| 5,576,427 A | 11/1996 | Cook | |
| 5,578,717 A | 11/1996 | Urdea | |
| 5,578,718 A | 11/1996 | Cook | |
| 5,580,731 A | 12/1996 | Chang | |
| 5,585,481 A | 12/1996 | Arnold | |
| 5,587,361 A | 12/1996 | Cook | |
| 5,587,371 A | 12/1996 | Sessler | |
| 5,587,469 A | 12/1996 | Cook | |
| 5,591,584 A | 1/1997 | Chang | |
| 5,591,722 A | 1/1997 | Montgomery | |
| 5,594,121 A | 1/1997 | Froehler | |
| 5,595,726 A | 1/1997 | Magda | |
| 5,596,086 A | 1/1997 | Matteucci | |
| 5,596,091 A | 1/1997 | Switzer | |
| 5,597,696 A | 1/1997 | Linn | |
| 5,597,909 A | 1/1997 | Urdea | |
| 5,599,923 A | 2/1997 | Sessler | |
| 5,599,928 A | 2/1997 | Hemmi | |
| 5,602,240 A | 2/1997 | De Mesmaeker | |
| 5,608,046 A | 3/1997 | Cook | |
| 5,610,289 A | 3/1997 | Cook | |
| 5,610,300 A | 3/1997 | Altmann | |
| 5,614,617 A | 3/1997 | Cook | |
| 5,614,621 A | 3/1997 | Ravikumar | |
| 5,618,704 A | 4/1997 | Sanghvi | |
| 5,623,065 A | 4/1997 | Cook | |
| 5,623,070 A | 4/1997 | Cook | |
| 5,625,050 A | 4/1997 | Beaton | |
| 5,627,053 A | 5/1997 | Usman et al. | |
| 5,633,360 A | 5/1997 | Bischofberger | |
| 5,639,873 A | 6/1997 | Barascut | |
| 5,645,985 A | 7/1997 | Froehler | |
| 5,646,265 A | 7/1997 | McGee | |
| 5,646,269 A | 7/1997 | Matteucci | |
| 5,652,355 A | 7/1997 | Metelev | |
| 5,658,873 A | 8/1997 | Bertsch-Frank | |
| 5,663,312 A | 9/1997 | Chaturvedula | |
| 5,670,633 A | 9/1997 | Cook | |
| 5,672,697 A | 9/1997 | Buhr | |
| 5,677,437 A | 10/1997 | Teng | |
| 5,677,439 A | 10/1997 | Weis | |
| 5,681,941 A | 10/1997 | Cook | |
| 5,688,941 A | 11/1997 | Cook | |
| 5,700,920 A | 12/1997 | Altmann | |
| 5,700,922 A | 12/1997 | Coo | |
| 5,721,218 A | 2/1998 | Froehler | |
| 5,750,692 A | 5/1998 | Cook | |
| 5,760,209 A | 6/1998 | Cheruvallath | |
| 5,763,588 A | 6/1998 | Matteucci | |
| 5,770,713 A | 6/1998 | Imbach | |
| 5,792,608 A | 8/1998 | Swaminathan | |
| 5,792,747 A | 8/1998 | Schally | |
| 5,830,653 A | 11/1998 | Froehler | |
| 5,845,205 A | 12/1998 | Alanara | |
| 5,874,443 A | 2/1999 | Kiely | |

| | | |
|---|---|---|
| 5,898,031 A | 4/1999 | Crooke |
| 6,005,096 A | 12/1999 | Matteucci |
| 6,007,992 A | 12/1999 | Lin |
| 6,020,475 A | 2/2000 | Capaldi |
| 6,028,183 A | 2/2000 | Lin |
| 6,051,699 A | 4/2000 | Ravikumar |
| 6,107,094 A | 8/2000 | Crooke |
| 6,118,800 A | 9/2000 | Kidoguchi |
| 6,121,437 A | 9/2000 | Guzaev |
| 6,127,346 A | 10/2000 | Peyman |
| 6,136,568 A | 10/2000 | Hiatt et al. |
| 6,147,200 A | 11/2000 | Manoharan |
| 6,169,177 B1 | 1/2001 | Manoharan |
| 6,252,061 B1 | 6/2001 | Sampath |
| 6,287,860 B1 | 9/2001 | Monia |
| 6,326,478 B1 | 12/2001 | Cheruvallath |
| 6,465,628 B1 | 10/2002 | Ravikumar |
| 6,610,289 B2 | 8/2003 | Drake |
| 6,914,054 B2 | 7/2005 | Sommadossi et al. |
| 7,030,230 B2 | 4/2006 | Ross et al. |

FOREIGN PATENT DOCUMENTS

| | | |
|---|---|---|
| EP | 0770621 | 5/1997 |
| EP | 1541581 | 6/2005 |
| WO | WO 89/12060 | 12/1989 |
| WO | WO 90/02749 | 3/1990 |
| WO | WO 91/04982 | 4/1991 |
| WO | WO 93/07883 | 4/1993 |
| WO | WO 93/24510 | 12/1993 |
| WO | WO 94/02499 | 2/1994 |
| WO | WO 94/17093 | 8/1994 |
| WO | WO 94/26764 | 11/1994 |
| WO | WO 96/07392 | 3/1996 |
| WO | WO 97/38001 | 10/1997 |
| WO | WO 98/39352 | 9/1998 |
| WO | WO 99/14226 | 3/1999 |
| WO | WO 99/32619 | 7/1999 |
| WO | WO 00/08044 | 2/2000 |
| WO | WO 00/44895 | 8/2000 |
| WO | WO 00/44914 | 8/2000 |
| WO | WO 00/49035 | 8/2000 |
| WO | WO 00/63364 | 10/2000 |
| WO | WO 01/29058 | 4/2001 |
| WO | WO 01/36641 | 4/2001 |
| WO | WO 01/36646 | 5/2001 |
| WO | WO 01/48183 | 7/2001 |
| WO | WO 01/75164 | 10/2001 |
| WO | WO 2004/044138 | 5/2004 |

OTHER PUBLICATIONS

U.S. Appl. No. 09/123,108, filed Jul. 27, 1998, Manoharan.
U.S. Appl. No. 09/130,973, filed Aug. 7, 1998, Manoharan.
U.S. Appl. No. 09/349,040, filed Jul. 7, 1999, Manoharan.
U.S. Appl. No. 09/370,541, filed Aug. 9, 1999, Manoharan.
U.S. Appl. No. 09/334,130, filed Jun. 15, 1999, Manoharan.
U.S. Appl. No. 09/344,260, filed Jun. 25, 1999, Manoharan.
U.S. Appl. No. 09/996,292, filed No. 28, 2001, Manoharan.
U.S. Appl. No. 10/013,295, filed May 24, 2002, Manoharan.
U.S. Appl. No. 10/155,920, filed May 24, 2002, Manoharan.
Bayer et al., "Improved Conditions for Solid Phase Synthesis of Oligonucleotides on P5-PEG Copolymers" Z. Naturforsch (1995) 50b:1096-1100.
Beaucage et al., "Deoxynucleoside Phosphoramidites—A New Class of Key Intermediates for Deoxypolynucleotide Synthesis" Tetrahedron Lett. (1981) 22:1859-1862.
Belikova et al., "Synthesis of Ribonucleosides and Dribonucleoside Phosphates Containing 2- Chlorethylamine and Nitrogen Mustard Residues" Tet. Lett. (1967) 37:3557-3562.
Bellon et al., "4-thio-RNA: a novel class of sugar-modified Beta-RNA" ACS Symposium Series (1994) 580:68-79.
Berg et al., "Long Chain Polyethylene Film Matrix: A New Support for Solid-Phase Peptide Synthesis" J. Am. Chem. Soc. (1989) 111:8024.
Berger et al., "Crystal Structures of B-DNA with Incorporated 2'-Deoxy-Fluoro-Arabino-Furanosyl Thymines: Implications of Conformational Preorganization for Duplex Stability" Nucleic Acids Research (1998) 26:2473-2480.

Boggon et al., "The crystal structure analysis of d(CGCGAASSCGCG)2, a synthetic DNA dodecamer duplex containing four 4'-thio-2'-deoxythymidine nucleotides" Nucleic Acids Research (1996) 24(5):951-961.
Bonora et al., "A Liquid-Phase Process Suitable for Large-Scale Synthesis of Phosphorothioate Oligonucleotides" Organic Process Research & Development (2000) 4:225-231.
Boutla et al., "Short 5'-phosphorylated double-stranded RNAs induce RNA interference in *Drosophila*" Curr. Biol. (2001) 11:1776-1780.
Brantl, "Antisense-RNA regulation and RNA interference" Biochim. Biophys. Acta. (2002) 1575(1-3):15-25.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
Agrawal, Protocols for Oligonucleotides and Analogs ed., (1993) Totowa, New Jersey: Humana Press, Inc.
Altmann et al., "Second Generation of Antisense Oligonucleotides: From Nuclease Resistance to Biological Efficacy in Animals" Chimia (1996) 50:168-176.
Altmann et al., "Second-Generation Antisense Oligonucleotides: Structure-Activity Relationships and the Design of Improved Signal-Transudction Inhibitors" Biochem Soc Trans. (1996) 24:640-637.
Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16:917-926.
Altschul et al., "Basic Local Alignment Search Tool" J. Mol. Biol. (1990) 215:403-410.
Alul et al., "Oxalyl-CPG: A Labile Support for Synthesis of Sensitive Oligonucleotide Derivatives" Nucleic Acids Research (1991) 19:1527-1532.
Arnott et al., "Optimised Parameters for A-DNA and B-DNA" Biochem. Biophys. Res. Comm. (1972) 47:1504-1509.
Atherton et al., "Polyamide supports for polypeptide synthesis" J. Am. Chem. Soc. (1975) 97:6584-6855.
Atherton et al., "The polyamide method of solid phase peptide and Oligonucleotide synthesis" Bioorg. Chem. (1979) 8:351-370.
Atherton et al., "Peptide synthesis. Part 2. Procedures for solid-phase synthesis using Na-fluorenylmethoxycarbonylamino-acids on polyamide supports. Synthesis of substance p and of acyl carrier protein 65-74 decapeptide" J.C.S. Perkin I (1981) 538-546.
Baker et al., "2-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11944-12000.
Bass, "Double-stranded RNA as a template for gene silencing" Cell (2000) 101:235-238.
Bayer et al., "A New Support for Polypeptide Synthesis" Tetrahedron Lett. (1970) 4503.
Chiang et al., "Antisense Oligonucleotides Inhibit Intercellular Adhesion Molecule 1 Expression by Two Distinct Mechanisms" J. Biol. Chem. (1991) 266:18162-18171.
Chiu et al., "RNAi in human cells: basic structural and functional features of small interfering RNA" Molecular Cell (2002) 10:549-561.
Cogoni et al., "Post-Transcriptional Gene Silencing Across Kingdoms" Curr. Opin. Genetics Dev. (2000) 10:638-643.
Conte et al., "Conformational properties and thermodynamics of the RNA duplex r(CGCAAUUUGCG)2: comparison with the DNA analogue d(CGCAAATTTGCG)2" Nucleic Acids Res. (1997) 25:2627-2634.
Crooke et al., "Pharmacokinetic Properties of Several Novel Oligonucleotide Analogs in Mice" J. Pharmacol. Exp. Ther. (1996) 277:923-937.

Dahl et al., "A Highly Reactive Odourless Substitute for Thiophenol/Triethylamine as a Deprotective Reagent in the Synthesis of Oligonucleotides and their Analogues" Acta Chem. Scand. (1990) 44:639-641.

Damha et al., "Oligoribonucleotide synthesis. The silyl-phosphoramidite method" Methods Mol. Biol. (1993) 20:81-114.

Daniels et al., "Membranes as Solid Supports for Peptide Synthesis" Tetrahedron Lett. (1989) 4345-4348.

Dukhan et al., "4'-thio-RNA: synthesis, base pairing properties and interaction with dimerization initiation site of HIV-1" Nucleosides & Nucleotides (1999) 18(6&7):1423-1424.

Eckstein, Oligonucleotides and Analogues, a Practical Approach (1991) Oxford Univ. Press, NY.

Egli et al., "RNA Hydration: A Detailed Look" Biochemistry (1996) 35:8489-8494.

Eichler et al., "Applications of Cellulose Paper as Support Material in Simultaneous Solid Phase Peptide Synthesis" Collect. Czech. Chem. Commun. (1989) 54:1746.

Elbashir et al., "Functional anatomy of siRNAs for mediating efficient RNAi in Drosophila melanogaster embryo lysate" EMBO J. (2001) 29:6877-6888.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., "Chemically Modified Oligonucleotides as Probes and Inhibitors" Agnew Chem. Int. Ed. Engl. (1991) 30:613-629.

Fedoroff et al., "Structure of a DNA:RNA hybrid duplex. Why RNase H does no cleave pure RNA" J. Mol Biol. (1993) 233:509-523.

Fire et al., "Potent and Specific Genetic Interference by Double-Stranded RNA in Caenorhabditis elegans" Nature (1998) 391:806-811.

Flanagan et al., "A cytosine analog that confers enhanced potency to antisense oligonucleotides" PNAS (1999) 96:3513-3518.

Francis et al., "Probing the Requirements for Recognition and Catalysis in Fpg and MutY with Nonpolar Adenine Isosteres" J. Am. Chem. Soc. (2003) 125:16235-26242.

Fromageot et al., "The synthesis of oligoribonucleotides. 3. Monoacylation of ribonucleosides and derivatives via orthoester exchange" Tetrahedron (1967) 23:2315-2331.

Fuchs et al., "Identification of Differentially Expressed Genes by Mutually Subtracted RNA Fingerprinting" Anal. Biochem. (2000) 286:91-98.

Gait, "Oligoribonucleotides" Antisense Research and Applications (1993), CRC Press, Boca Raton, pp. 289-301.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Geysen et al., "Use of Peptide Synthesis to Probe Viral Antigens for Epitopes to a Resolution of a Single Amino Acid" PNAS (1984) 81:3998.

Going et al., "Molecular Pathology and Future Developments" Eur. J. Cancer (1999) 35:1895-1904.

Gonzalez et al., "Structure and dynamics of a DNA:RNA hybrid duplex with a chiral phosphorothioate moiety: NMR and molecular dynamics with conventional and time-averaged restraints" Biochemistry (1995) 34:4969-4982.

Gorman, "An Apparatus for Simultaneous Manual Solid-Phase Synthesis of Multiple Peptide Analogs" Anal. Biochem (1984) 136;397.

Gravert et al., "Organic Synthesis on Soluble Polymer Supports: Liquid-Phase Methodologies" Chem. Rev. (1997) 97:489-510.

Greene et al., Protecting Groups in Organic Synthesis 2nd Ed. (1991) John Wiley & Sons, NY.

Griffin et al., "The Synthesis of Oligoribonucleotides—2 Methoxymethylidene Derivatives of Ribonucleosides and 5'-Ribonucleotides" Tetrahedron Lett. (1967) 23:2301-2313.

Guckian et al., "Structure and Base Pairing Properties of a Replicable Nonpolar Isotere for Deoxyadenosine" J. Org. Chem. (1998) 63:9652-9656.

Guillerm et al., "Synthesis of 4'-Fluoroadenosine as an Inhibitor of S-Adenosyl-L-Homocysteine Hydrolase" Bioorganic and Medicinal Chemistry Letters (1995) 5:1455-1460.

Guo et al., "par-1, a gene required for establishing polarity in C. elegans embryos, encodes a putative Ser/Thr kinase that is asymmetrically distributed" Cell (1995) 81:611-620.

Gura, "A silence that speaks volumes" Nature (2000) 404:804-808.

Hakimelahi et al., "High Yield Selective 3'-Silylation of Ribonucleosides" Tetrahedron Lett. (1981) 22:5243-5246.

Harry-O'Kura et al., "A Short, Flexible Route Toward 2'-C-Branched Ribonucleosides" J. Org. Chem. (1997) 62:1754-1759.

Hill et al., "Polymerase recognition of synthetic oligodeoxynucleotides incorporating degenerate pyrimidine and purine bases" PNAS (1998) 95:4258-4263.

Holm et al., "Proceedings of the 20th European Peptide Symposium" G. Jung and E. Bayer eds., Berlin: Walter de Gruyter & Co. (1989) pp. 208-210.

Horton et al., "The structure of a RNA/DNA hybrid: a substrate of the ribonuclease activity of HIV-1 reverse transcriptase" J. Mol. Biol. (1996) 264:521-533.

Houghten "General method for the rapid solid-phase synthesis of large numbers of peptides: specificity of antigen-antibody interaction at the level of individual amino acids" PNAS (1985) 82:5131-5135.

Jacobson et al., "Methanocarba analogues of purine nucleosides as potent and selective adenosine receptor agonists" J. Med Chem. (2000) 43:2196-2203.

Jacques et al., Enantiomers, Racemates, and Resolutions (1981) New York: John Wiley & Sons.

Jones et al., "Migration of t-Butyldimethylsilyl Protecting Groups" J. Chem. Soc. (1979) 2762-2764.

Jones et al., "RNA Quantitation by Fluorescence-Based Solution Assay: RiboGreen Reagent Characterization" Analytical Biochemistry (1998) 265:368-374.

Jones et al., "Investigation of some properties of oligodeoxynucleotides containing 4'-thio-2'-deoxynucleotides: duplex hybridization and nuclease sensitivity" Nucleic Acids Research (1996) 24(21):4117-4122.

Jorgensen et al., "Chalcone synthase cosuppression phenotypes in petunia flowers: comparison of sense vs. antisense constructs and single-copy vs. complex T-DNA sequences" Plant. Mol. Biol. (1996) 31:957-973.

Jungblut et al., "Proteomics in human disease: Cancer, heart and infections diseases" Electrophoresis (1999)20:2100-2110.

Jurecic et al., "Long-distance DD-PCR and cDNA microarrays" Curr. Opin. Microbiol. (2000) 3:316-321.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-30.

Kawasaki et al., "Uniformly modified 2'-deoxy-2'-fluoro phosphorothioate oligonucleotides as nuclease-resistant antisense compounds with high affinity and specificity for RNA targets" J. Med. Chem. (1993) 36:831-41.

Kent et al., "Preparation and properties of tert-Butyloxcarbonylaminoacyl-4-(oxymethyl)phenylacetamidomethyl-(Kel F-g-styrene) Resin, an insoluble, noncrosslinked support for solid phase peptide synthesis" Israel J. Chem. (1978) 17:243-247.

Klopffer et al., "The effect of universal fluorinated nucleobases on the catalytic activity of ribozymes" Nucleosides, Nucleotides & Nucleic Acids (2003) 22:1347-1350.

Klopffer et al., "Synthesis of 2'-aminoalkyl-substituted fluorinated nucleobases and their influence on the kinetic properties of hammerhead ribozymes" ChemBioChem (2004) 5:707-716.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Koshkin et al., "LNA (locked nucleic acid): An RNA Mimic Forming Exceedingly Stable LNA:LNA Duplexes" J. Am. Chem. Soc. (1998) 120:13252-13253.

Krchnak et al., "Multiple continuous-flow solid-phase peptide synthesis" Int. J. Peptide Protein Res. (1989) 33:209-213.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16:1837-1846.

Lai et al., "Fluorinated DNA bases as probes of electrostatic effects in DNA base stacking" Angew. Chem. Int. Ed. (2003) 42:5973-5977.

Lai et al., "Selective pairing of polyfluorinated DNA bases" J. Am. Chem. Soc. (2004) 126:3040-3041.

Lane et al., "NMR assignments and solution conformation of the DNA:RNA hybrid duplex d(GTGAACTT)r(AAGUUCAC)" Eur. J. Biochem. (1993) 215:297-306.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotech. (2000) 80:143-157.

Lebl et al., "Simulation of continuous solid phase synthesis: synthesis of methionine enkephalin and its analogs" Peptide Res. (1989) 2:232.

Lee et al., "Ring-Constrained (N)-methanocarba nucleosides as adenosine receptor agonists: independent 5'-uronamide and 2'-deoxy modifications" Bioorg Med Chem Lett (2001) 11:1333-1337.

Lesnik et al., "Relative thermodynamic stability of DNA, RNA and DNA:RNA hybrid duplexes: relationship with base composition and structure" Biochemistry (1995) 34:10807-10815.

Letsinger et al., "Cholesteryl-conjugated oligonucleotides: synthesis, properties, and activity as inhibitors of replication of human immunodeficiency virus in cell culture" PNAS (1989) 86:6553-6.

Leydier "A new synthesis of some 4'-thio-d-ribonucleosides and preliminary enzymatic evaluation" Nucleosides & Nucleotides (1994) 13:2035-2050.

Leydier et al., "4'-thio-RNA: synthesis of mixed base 4'-thio-oligoribonucleotides, nuclease resistance, and base pairing properties with complementary single and double strand" Antisense Research and Development (1995) 5:167-174.

Leydier et al., "4'-thio-B-D-Oligoribonucleotides: nuclease resistance and hydrogen bonding properties" Nucleosides & Nucleotides (1995) 14:1027-1030.

Lin et al., "Tricyclic 2'-Deoxycytidine Analogs: Syntheses and Incorporation into Oligodeoxynucleotide Which Have Enhanced Binding to Complementary RNA" J. Am. Chem. Soc. (1995) 117:3873-3874.

Lin et al., "A Cytosine Analogue Capable of Clamp-Like Binding to a Guanine in Helical Nucleic Acids" J. Am. Chem. Soc. (1998) 120:8531-8532.

Liu et al., "A four-base paired genetic helix with expanded size" Sceience (2003) 302:868-871.

Liu et al., "Toward a new genetic system with expanded dimensions: size-expanded analogues of deoxyadenosine and thymidine" J. Am. Chem. Soc. (2004) 126:1102-1109.

Loakes, "Survey and summary: The applications of universal DNA base analogues" Nucleic Acids Research (2001) 29(12):2437-2447.

Madden et al., "Serial analysis of gene expression: from gene discovery to target identification" DDT (2000) 5:415-425.

Manoharan et al., "Chemical Modifications to Improve Uptake and Bioavailability of Antisense Oligonucleotides" Ann NY Acad Sci (1992) 28:306-309.

Manoharan et al., "Introduction of a Lipophilic Thioether Tether in the Minor Groove of Nucleic Acids for Antisense Applications" Bioorg. Med. Chem. (1993) 3:2765-2770.

Manoharan et al., "Cholic Acid-Oligonucleotide Conjugates for Antisense Applications" Bioorg. Med. Chem. Let. (1994) 4:1053-1060.

Manoharan et al., "Lipidic Nucleic Acids" Tetrahedron Lett. (1995) 36:3651-3654.

Manoharan et al., "Oligonucleotide Conjugates: Alteration of the Pharmacokinetic Properties of Antisense Agents" Tetrahedron Lett. (1995) 14:969-973.

Martin et al., "Ein Neuer Zugang Zu 2'-O-Alkyribonucleoslden Und Eigenschaften Deren Oligonucleotide" Helv. Chim. Acta (1995) 78:486-504.

Martinez et al., "Single-stranded antisense siRNAs guide target RNA cleavage in RNAi" Cell (2002) 110:563-574.

Matteucci et al., "Synthesis of deoxyoligonucleotides on a polymer support" J. Am. Chem. Soc. (1981) 103:3185-3191.

Mellitzer et al., "Spatial and temporal 'knock down' of gene expression by electroporation of double-stranded RNA and morpholinos into early postimplantation mouse embryos" Mechanisms of Development (2002) 118:57-63.

Miller et al., "Synthesis of 4'-thiofuranoid 1, 2-glcals and their application to stereoselective synthesis of 4'-thionucleosides" Tetrahedron Letters (2000) 41:3265-3268, especially compound 5 on p. 3266.

Mishra et al., "Improved leishmanicidal effect of phosphorotioate antisense oligonucleotides by LDL-mediated delivery" Biochim Biophys Acta (1995) 1264:229-237.

Montgomery et al., "RNA as a target of double-stranded RNA-mediated genetic interference in Caenorhabditis elegans" Proc Natl. Acad. Sci. (1998) 95:15502-7.

Moran et al., "A thymidine triphosphate shape analog lacking Watson-Crick pairing ability is replicated with high sequence selectivity" PNAS (1997) 94:10506-10511.

Moran et al., "Difluorotoluene, a nonpolar isostere for thymine, codes specifically and efficiently for adenine in DNA replication" J. Am. Chem. Soc. (1997) 119:2056-2057.

Morita et al., "2-O-4'-C-Ethylene-Bridged Nucleic Acids (ENA): Highly Nuclease-Resistant and Thermodynamically Stable Oligonucleotides for Antisense Drug" Bioorg. Med. Chem. Lett. (2002) 12:73-76.

Naka et al., "Stereoselective synthesis of 4'-thioribonucleosides utilizing Pummerer reaction" Nucleic Acids Symposium Ser. (1998) 39:21-22.

Naka et al., "The stereoselective synthesis of 4'-Beta-thioribonucleosides via the pummerer reaction" J. Am. Chem. Soc. (2000) 122(30):7233-7243.

Napoli et al., "Introduction of a Chimeric Chalcone Synthase Gene into Petunia Results in Reversible Co-Suppression of Homologous Genes in trans" Plant Cell (1990) 2:279-289.

Nishikura et al., "A Short Primer on RNAi: RNA-Directed RNA Polymerase Acts as a Key Catalyst" Cell (2001) 107:415-418.

Oberhauser et al., "Effective incorporation of 2'-O-methyl-oligoribonucleotides into lipsomes and enhanced cell association through modification with thiocholesterol" Nucleic Acids Res. (1992) 20:533-538.

Ogilvie et al., "The Use of Silyl Groups in Protecting the Hydroxyl Functions of Ribonucleosides" Tetrahedron Lett. 15:2861-2863, (1974).

O'Neil et al., "A highly effective nonpolar isostere of deoxyguanosine: synthesis, structure, stacking, and base pairing" J. Org. Chem. (2002) 67:5869-5875.

Owen et al., "4'-Substituted Nucleosides. 3. Synthesis of some 4'-fluorouridine derivatives" J. Org. Chem. (1976) 41:3010-3017.

Parr et al., "Solid-Phase Peptide Synthesis on an Inorganic Matrix having Organic Groups on the Surface" Angew. Chem. Internal, ed. (1972) 11:314-315.

Parrish et al., "Functional anatomy of a dsRNA trigger: differential requirement for the two trigger strands in RNA interference" Molecular Cell (2000) 6:1077-1087.

Pitsch, "Protecting Groups for the Synthesis of Ribonucleic Acides" Chimia (2001) 55:320-324.

Prashar et al., "READS: A Method for Display of 3'-End Fragment of Restriction Enzyme-Digested cDNAs for Analysis of Differential Gene Expression" Methods Enzymol. (1999) 303:258-272.

Rausch et al., "Hydrolysis of RNA/DNA hybrids containing nonpolar pyrimidine isosteres defines regions essential for HIV type 1 polypurine tract selection" PNAS (2003) 100:11279-11284.

Reddy et al., "Fast cleavage and deprotection of Oligonucleotides" Tetrahedron Lett. (1994) 35:4311-4314.

Reese et al., "An Acetal Group Suitable for the Protection of 2'-Hydroxy Functions in Rapid Oligoribonucleotide Synthesis" Tetrahedron Lett. (1986) 27:2291.

Renneberg et al., "Watson-Crick base-pairing properties of tricycle-DNA" J. Am. Chem. Soc. (2002) 124:5993-6002.

Saison-Behmoaras et al., "Short modified antisense oligonucleotides directed against Ha-ras point mutation induce selective cleavage of the mRNA and inhibit T24 cells proliferation" EMBO J. (1991) 10:1111-1118.

Sanger et al., Principles of Nucleic Acid Structure (1984) Springer-Verlag: New York, NY.

Sanghvi et al., "Heterocyclic Base Modifications in Nucleic Acids and Their Applications in Antisense Oligonucleotides" Antisense Research and Applications (1993) 276-278.

Scaringe, "RNA Oligonucleotide Synthesis via 5'-Silyl-2'-Orthoester Chemistry" Methods (2001) 23:206-217.

Scaringe et al., "Novel RNA Synthesis Method using 5'-O-Silyl-2'-O-orthoester protecting groups" J. Am. Chem. Soc. (1998) 120:11820-11821.

Scaringe et al., "Chemical synthesis of biologically active oligoribonucleotides using Beta-cyanoethyl protected ribonucleoside phosphoramidites" Nucleic Acids Research (1990) 18(18):5433-5441.

Schwartz et al., "Rapid synthesis of oligoribonucleotides using 2'-O-(o-nitrobenzyloxymethyl)-protected monomers" Bioorg. Med. Chem. Lett. (1992) 9:1019-1024.

Schwarz et al., "Evidence that siRNAs function as guides, not primers, in the *Drosophila* and human RNAi pathways" Molecular Cell (2002) 10:537-548.

Scott et al., "The use of resing coated glass beads in the form of a packed bed for the solid phase synthesis of peptides" J. Chrom. Sci. (1971) 9:577-591.

Searle et al., "On the stability of nucleic acid structures in solution: enthalpy-entropy compensations, internal rotations and reversibility" Nucleic Acids Res. (1993) 21:2051-2056.

Shea et al., "Synthesis, hybridization properties and antiviral activity of lipid-oligodeoxynucleotide conjugates" Nucleic Acids Res. (1990) 18:3777-83.

Singh et al., "Synthesis of 2'-amino-LNA: A novel conformationally restricted high-affinity oligonucleotide analogue with a handle" J. Org. Chem. (1998) 63: 10035-10039.

Singh et al., "LNA (locked nucleic acids): synthesis and high-affinity nucleic acid recognition" Chem. Commun. (1998) 455-456.

Steffens et al., "Nucleic-acid analogs with constraint conformational flexibility in the sugar-phosphate backbone 'tricycle-DNA'," Helv. Chim. Acta (1997) 80:2426-2439.

Steffens et al., "Synthesis and thermodynamic and biophysical properties of tricycle-DNA" J. Am. Chem. Soc. (1999) 121:3249-3255.

Sutcliffe et al., "TOGA: An automated parsing technology for analyzing expression of nearly all genes" PNAS (2000) 97:1976-1981.

Svinarchuk et al., "Inhibition of HIV proliferation of MT-4 cells by antisense oligonucleotide conjugated to lipophilic groups" Biochimie (1993) 75:49-54.

Tabara et al., "RNAi in *C. elegans*: Soaking in the Genome Sequence" Science (1998) 282:430-431.

Tang et al., "2'-C-Branched Ribonucleosides: Synthesis of the Phosphoramidite Derivatives of 2'-C-beta-Methylcytidine and their Incorporation into Oligonucleotides" J. Org. Chem. (1999) 64:747-754.

Tijsterman et al., "RNA hellcase MUT-14-dependent gene silencing triggered in *C. elegans* by short antisense RNAs" Science (2002) 295:694-7.

Timmons et al., "Specific Interference by Ingested dsRNA" Nature (1998) 395:854.

Timmons et al., "Ingestion of bacterially expressed dsRNAs can produce specific and potent genetic interference in *Caenorhabditis elegans*" Gene (2001) 263:103-112.

To, "Identification of Differential Gene Expression by High Throughput Analysis" Comb. Chem. High Throughput Screen (2000) 3:235-241.

Townsend, Chemistry of Nucleosides and Nucleotides, vol. 1-3, ed., Plenum press (1988).

Treagear, "Graft copolymers as insoluble supports in peptide synthesis" Chemistry and Biology of Peptides, J. Meienhofer, ed., Ann Arbor Sci. Publ., Ann Arbor (1972) pp. 175-178.

Tuschl et al., "Targeted mRNA degradation by double-stranded RNA in vitro" Genes Dev. (1999) 15:3191-7.

Van Rietschoten et al., "Simultaneous synthesis of two peptide analogs on different insoluble supports" Peptides (1975) 13:113-116.

Wahlestedt et al., "Potent and nontoxic antisense oligonucleotide containing locked nucleic acids" Proc. Natl. Acad. Sci. USA (2000) 97: 5633-5638.

Wang et al., "Synthesis and binding property of an oligonucleotide containing tetrafluorophenoxazine" Tetrahedron Lett. (1998) 39:8385-8388.

Wengel et al., "LNA (locked nucleic acid)" Nucleosides & Nucleotides (1999) 18:1365-1370.

Wincott et al., "Synthesis, deprotection, analysis and purification or RNA and ribozymes" Nucleic Acids Res. (1995) 23:2677-2684.

Wright et al., "Large scale synthesis of Oligonucleotides via phosphoramidite nucleosides and a high-loaded polystyrene support" Tetrahedron Letters (1993) 34:3373-3376.

Yoshimura et al., "An alternative synthesis of the antinneoplastic nucleoside 4'-ThioFAC and its application to the synthesis of 4'-ThioFAG and 4'-Thiocytarazid" J. Org. Chem. (1999) 64:7912-7920, especially compound 33 on p. 7916.

Yoshimura et al., "An Alternative Synthesis of Antineoplastic 4'-Thiocytidine Analogue 4'-ThioFAC" Tetrahedorn Letters (1999) 41(10):1937-1940.

Zamecnik et al., "Inhibition of Rous sarcoma virus replication and cell transformation by a specific oligodeoxynucleotide" PNAS (1978) 75:280-284.

Zhang et al., "PowerBLAST: A New Network BLAST Application for Interactive or Automated Sequence Analysis and Annotation" Genome Res. (1997) 7:649-656.

Organic Solvents Physical Properties and Methods of Purification, 4th edition, vol. II, in the Techniques of Chemistry Series, New York: John Wiley & Sons (1986).

Principles of Nucleic Acid Structure, Wolfgang Sanger (1984) Springer-Verlag.

Synthetic Peptides: A User's Guide, Gregory A. Grant, ed. Oxford University Press (1992).

Supplementary European Search Report for EP 04816222 dated Jul. 22, 2009.

International Search Report for PCT/US04/30874 dated Apr. 18, 2007.

PTEN siRNA Constructs

| Alias id | Notation | Equivalent Sequence |
|---|---|---|
| 341401 | $A_{ro}A_{ro}G_{ro}U_{ro}A_{ro}A_{ro}G_{ro}G_{ro}A_{ro}C_{ro}C_{ro}A_{ro}G_{ro}A_{ro}G_{ro}A_{ro}C_{ro}A_{ro}A_r$ | AAGTAAGGACCAGAGACAA (Sense) (SEQ ID NO: 8) |
| 341391 | $U_{ro}U_{ro}G_{ro}U_{ro}C_{ro}U_{ro}C_{ro}U_{ro}G_{ro}G_{ro}U_{ro}C_{ro}C_{ro}U_{ro}U_{ro}A_{ro}C_{ro}U_{ro}U_r$ | TTGTCTCTGGTCCTTACTT (Antisense) (SEQ ID NO: 9) |
| 375761 | $U_{so}U_{so}G_{ro}U_{ro}C_{ro}U_{ro}C_{ro}U_{ro}G_{ro}G_{ro}U_{ro}C_{ro}C_{ro}U_{ro}U_{ro}A_{ro}C_{xo}U_{xo}U_x$ | TTGTCTCTGGTCCTTACTT (Antisense) (SEQ ID NO: 9) |
| 375762 | $U_{ro}U_{ro}G_{mo}U_{ro}C_{ro}U_{ro}C_{ro}U_{xo}G_{ro}G_{ro}U_{ro}C_{ro}C_{xo}U_{ro}U_{ro}A_{ro}C_{ro}U_{xo}U_r$ | TTGTCTCTGGTCCTTACTT (Antisense) (SEQ ID NO: 9) |

Key: o = phosphodiester linkage
r = ribose sugar;
s = 4'-thioribose sugar
m = 2'-O-methylribose sugar
x = 2'-O-methyl-4'-thioribose sugar

Figure 1

OLIGOMERIC COMPOUNDS COMPRISING 4'-THIONUCLEOSIDES FOR USE IN GENE MODULATION

CROSS-REFERENCE TO RELATED APPLICATIONS

This application is a divisional of U.S. application Ser. No. 10/946,147, filed Sep. 20, 2004, which claims priority to U.S. provisional application Ser. No. 60/503,997 filed Sep. 18, 2003, each above application is incorporated herein by reference in its entirety.

SEQUENCE LISTING

The present application is being filed along with a Sequence Listing in electronic format. The Sequence Listing is provided as a file entitled CHEM0011USD1SEQ.txt, created on Aug. 30, 2010 which is 4 Kb in size. The information in the electronic format of the sequence listing is incorporated herein by reference in its entirety.

FIELD OF THE INVENTION

The present invention provides monomeric and oligomeric compounds comprising 4'-thionucleosides. More particularly, the present invention provides oligomeric compounds and compositions comprising at least one 4'-thionucleoside of the invention. In some embodiments, the oligomeric compounds and compositions of the present invention hybridize to a portion of a target RNA resulting in loss of normal function of the target RNA.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense compounds have been employed as therapeutic agents in the treatment of disease states in animals, including humans. Antisense oligonucleotide drugs are being safely and effectively administered to humans in numerous clinical trials. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently used in the treatment of cytomegalovirus (CMV)-induced retinitis in AIDS patients. A New Drug Application (NDA) for Genasense™ (oblimersen sodium; developed by Genta, Inc., Berkeley Heights, N.J.), an antisense compound which targets the Bcl-2 mRNA overexpressed in many cancers, was accepted by the FDA. Many other antisense compounds are in clinical trials, including those targeting c-myc (NeuGene® AVI-4126, AVI BioPharma, Ridgefield Park, N.J.), TNF-alpha (ISIS 104838, developed by Isis Pharmaceuticals, Inc.), VLA4 (ATL1102, Antisense Therapeutics Ltd., Toorak, Victoria, Australia) and DNA methyltransferase (MG98, developed by MGI Pharma, Bloomington, Minn.), to name a few.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Antisense technology is an effective means for reducing the expression of one or more specific gene products and can therefore prove to be uniquely useful in a number of therapeutic, diagnostic, and research applications.

Consequently, there remains a long-felt need for agents that specifically regulate gene expression via antisense mechanisms. Disclosed herein are antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the petunia flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., Plant Cell, 1990, 2, 279-289; Jorgensen et al., Plant Mol. Biol., 1996, 31, 957-973).

Cosuppression has since been found to occur in many species of plants, fungi, and has been particularly well characterized in *Neurospora crassa*, where it is known as "quelling" (Cogoni et al., Genes Dev. 2000, 10, 638-643; and Guru, Nature, 2000, 404, 804-808).

The first evidence that dsRNA could lead to gene silencing in animals came from work in the nematode, *Caenorhabditis elegans*. In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo et al., Cell, 1995, 81, 611-620). This result was a puzzle until Fire et al. injected dsRNA (a mixture of both sense and antisense strands) into *C. elegans*. This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., Nature, 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, Nature 1998, 395, 854; and Timmons et al., Gene, 2001, 263, 103-112). Further work showed that soaking worms in dsRNA was also able to induce silencing (Tabara et al., Science, 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *C. elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene. Introduction of exogenous double-stranded RNA (dsRNA) into *C. elegans* has been shown to specifically and potently disrupt the activity of genes containing homologous sequences. Montgomery et al. suggests that the primary interference effects of dsRNA are post-transcriptional; this conclusion being derived from examination of the primary DNA sequence after dsRNA-mediated interference a finding of no evidence of alterations followed by studies involving alteration of an upstream operon having no effect on the activity of its downstream gene. These results argue against an effect on initiation or elongation of transcription. Finally, they observed by in situ hybridization, that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted mRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., Proc. Natl. Acad. Sci. USA, 1998, 95, 15502-15507).

Recently, the development of a cell-free system from syncytial blastoderm *Drosophila* embryos that recapitulates many of the features of RNAi has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., Genes Dev., 1999, 13, 3191-3197).

In subsequent experiments, Tuschl et al, using the *Drosophila* in vitro system, demonstrated that 21- and 22-nt RNA fragments are the sequence-specific mediators of RNAi. These fragments, which they termed short interfering RNAs (siRNAs) were shown to be generated by an RNase III-like processing reaction from long dsRNA. They also showed that chemically synthesized siRNA duplexes with overhanging 3' ends mediate efficient target RNA cleavage in the *Drosophila* lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., Genes Dev., 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., Nature, 2001, 411, 494-498).

Most recently, Tijsterman et al. have shown that, in fact, single-stranded RNA oligomers of antisense polarity can be potent inducers of gene silencing. As is the case for co-suppression, they showed that antisense RNAs act independently of the RNAi genes rde-1 and rde-4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., Science, 2002, 295, 694-697).

Several recent publications have described the structural requirements for the dsRNA trigger required for RNAi activity. Recent reports have indicated that ideal dsRNA sequences are 21 nt in length containing 2 nt 3'-end overhangs (Elbashir et al, EMBO, 2001, 20, 6877-6887; and Sabine Brantl, Biochimica et Biophysica Acta, 2002, 1575, 15-25). In this system, substitution of the 4 nucleosides from the 3'-end with 2'-deoxynucleosides has been demonstrated to not affect activity. On the other hand, substitution with 2'deoxynucleosides or 2'-OMe-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., Molecular Cell, 2000, 6, 1077-1087). It was also shown by Parrish et al., that chemical modification like 2'-amino or 5'-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Same "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-F-2'-deoxynucleosides appeared to be efficient in triggering RNAi response independent of the position (sense or antisense) of the 2'-F-2'-deoxynucleosides.

In one experiment the reduction of gene expression was studied using electroporated dsRNA and a 25 mer morpholino in post implantation mouse embryos (Mellitzer et al., Mehanisms of Development, 2002, 118, 57-63). The morpholino oligomer did show activity but was not as effective as the dsRNA.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these olibonucleotides serve as substrates for a dsRNase enzyme with resultant cleavage of the RNA by the enzyme.

In another recently published paper (Martinez et al., Cell, 2002, 110, 563-574) it was shown that double stranded as well as single stranded siRNA resides in the RNA-induced silencing complex (RISC) together with elF2C1 and elf2C2 (human GERp950 Argonaute proteins. The activity of 5'-phosphorylated single stranded siRNA was comparable to the double stranded siRNA in the system studied. In a related study, the inclusion of a 5'-phosphate moiety was shown to enhance activity of siRNAs in vivo in *Drosophilia* embryos (Boutla et al., Curr. Biol., 2001, 11, 1776-1780). In another study, it was reported that the 5'-phosphate was required for siRNA function in human HeLa cells (Schwarz et al., Molecular Cell, 2002, 10, 537-548).

In yet another recently published paper (Chiu et al., Molecular Cell, 2002, 10, 549-561) it was shown that the 5'-hydroxyl group of the siRNA is essential as it is phosphorylated for activity while the 3'-hydroxyl group is not essential and tolerates substitute groups such as biotin. It was further shown that bulge structures in one or both of the sense or antisense strands either abolished or severely lowered the activity relative to the unmodified siRNA duplex. Also shown was severe lowering of activity when psoralen was used to cross link an siRNA duplex.

Phosphorus protecting groups such as SATE ((S-acetyl-2-thioethyl) phosphate) have been used to block the phosphorus moiety of individual nucleotides and the internucleotide phosphorus linking moietys of oligonucleotides. These groups have also been used in biological systems to afford deprotected oligonucleotides intracellularly due to the action of intercellular esterases. Such groups are disclosed in PCT publications WO 96/07392, WO 93/24510, WO 94/26764 and U.S. Pat. No. 5,770,713.

One group of researchers has been studying the synthesis and certain properties of 4'-thio-containing compounds and have published their results (Nucleosides & Nucleotides, 1999, 18(6 & 7), 1423-1424; Antisense Research and Development, 1995, 5(3), 167-74; ACS Symposium Series, 1994, 580 (Carbohydrate Modifications in Antisense Research), 68-79; and Nucleosides & Nucleotides, 1995, 14(3-5), 1027-30).

Another paper describes the properties of oligodeoxynucleotides containing deoxy 4'-thionucleotides (Nucleic Acids Research, 1996, 24(21), 4117-4122).

The stereosynthesis of 4'-thioribonucleosides utilizing Pummerer reaction has been described by another group of researchers (Nucleic Acids Symposium Series, 1998, 39, 21-22; and J. American Chemical Society, 2000, 122(30), 7233-7243).

Like the RNAse H pathway, the RNA interference pathway of antisense modulation of gene expression is an effective means for modulating the levels of specific gene products and may therefore prove to be uniquely useful in a number of therapeutic, diagnostic, and research applications involving gene silencing. The present invention therefore further provides oligomeric compounds useful for modulating gene expression pathways, including those relying on an antisense mechanism of action such as RNA interference and dsRNA enzymes as well as non-antisense mechanisms. One having skill in the art, once armed with this disclosure will be able, without undue experimentation, to identify additional oligomeric compounds for these and other uses.

SUMMARY OF THE INVENTION

The present invention provides compounds having of formula (I):

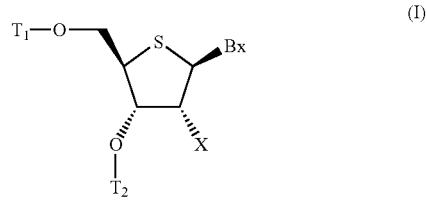

wherein:
$T_1$ is H, a protecting group, an activated phosphorus group, or, or -$L_s$-SS, wherein $L_s$ is a linking moiety and SS is a solid support medium;
$T_2$ is H, a protecting group, an activated phosphorus group, or -$L_s$-SS, wherein $L_s$ is a linking moiety and SS is a solid support medium;
Bx is hydrogen or a nucleobase;
X is halogen, amino, azido, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted alkoxy, substituted or unsubstituted —O—$C_2$-$C_{12}$ alkenyl, or substituted or unsubstituted —O—$C_2$-$C_{12}$ alkynyl, or X is a group of formula Ia or Ib:

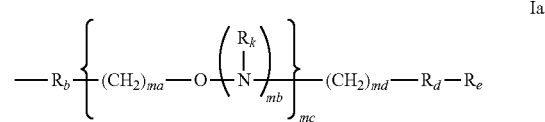

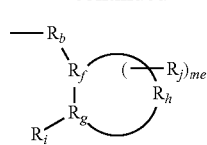

Ib wherein:
$R_b$ is O, S or NH;
$R_d$ is a single bond, O, S or C(=O);
$R_e$ is $C_1$-$C_{10}$ alkyl, $N(R_k)(R_m)$, $N(R_k)(R_n)$, N=C($R_p$)($R_q$), N=C($R_p$)($R_r$) or has formula Ic;

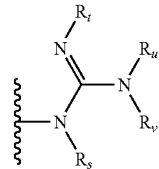

(Ic)

$R_p$ and $R_q$ are each independently hydrogen or $C_1$-$C_{10}$ alkyl;
$R_r$ is —$R_x$—$R_y$;
each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, $R_u$ and $R_v$, together form a phthalimido moiety with the nitrogen atom to which they are attached;
each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;
$R_k$ is hydrogen, an amino protecting group or —$R_x$—$R_y$;
$R_p$ is hydrogen, an amino protecting group or —$R_x$—$R_y$;
$R_x$ is a bond or a linking moiety;
$R_y$ is a chemical functional group, a conjugate group or a solid support medium;
each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;
or $R_m$ and $R_n$, together, are an amino protecting group, are joined in a ring structure that optionally includes an additional heteroatom selected from N and O or are a chemical functional group;
$R_i$ is $OR_z$, $SR_z$, or $N(R_z)_2$;
each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;
$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;
$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;
$m_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

In another embodiment of the present invention, oligomeric compounds are disclosed having at least one moiety of formula (II):

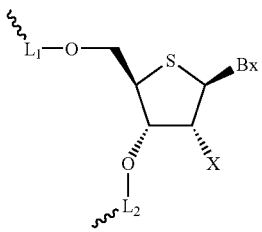

(II)

wherein Bx and X are defined herein and $L_1$ and $L_2$ are an internucleoside linkage as defined herein. Preferred internucleoside linkages for the oligomers of the present invention include, but are not limited to, phosphodiester linkages, phosphothioate linkages, and mixtures thereof. Preferred oligomers of the present invention include, but are not limited to, oligomers 8-80 nucleotides, 8-50 nucleotides, 8-30 nucleotides, 10-30 nucleotides, 15-30 nucleotides, 15-25 nucleotides, and the like.

Preferred X 2'-substituents include, but are not limited to: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_nCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gH]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heteroaromatic, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In other embodiments, X can include 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504). In further embodiments of the invention, X can include 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples delineated herein.

Other preferred modifications include 2'-methoxy(2'-O—CH$_3$), 2'-aminopropoxy(2'-OCH$_2$CH$_2$CH$_2$NH$_2$), 2'-allyl(2'-CH$_2$—CH═CH$_2$), 2'-O-allyl(2'-O—CH$_2$—CH═CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Particularly useful sugar substituent groups include O[(CH$_2$)$_g$O]$_h$CH$_3$, O(CH$_2$)$_g$OCH$_3$, O(CH$_2$)$_g$NH$_2$, O(CH$_2$)$_g$CH$_3$, O(CH$_2$)$_g$ONH$_2$, and O(CH$_2$)$_g$ON[(CH$_2$)$_g$H)]$_2$, where g and h are from 1 to about 10.

In one embodiment of the present invention, R$_2$ is H or hydroxyl and R$_1$ is allyl, amino, azido, O—CH$_3$, O—CH$_2$CH$_2$—O—CH$_3$, O—(CH$_2$)$_{ma}$—O—N(R$_m$)(R$_n$) or O—CH$_2$—C(═O)—N(R$_m$)(R$_n$);

wherein:
each R$_m$ and R$_n$ is, independently, H, an amino protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$)(R$_v$), guanidino and acyl where said acyl is an acid amide or an ester; and ma is from 1 to about 10.

A further embodiment of the present invention includes phorphoramidites of the nucleosides described by formula I, wherein one of T$_1$ or T$_2$ is an activated phosphorous group.

In yet another embodiment of the present invention are solid support bound nucleosides, wherein for formula I, one of T$_1$ or T$_2$ is -L$_s$-SS, wherein L$_s$ is a linking moiety and SS is a support medium.

In another embodiment of the present invention, compositions are disclosed comprising a first oligonucleotide and a second oligonucleotide, wherein:

at least a portion of said first oligonucleotide is capable of hybridizing with at least a portion of said second oligonucleotide, at least a portion of said first oligonucleotide is complementary to and capable of hybridizing to a selected target nucleic acid, and at least one of said first or said second oligonucleotides includes at least one nucleoside having a modification comprising a 4'-thionucleoside of formula II:

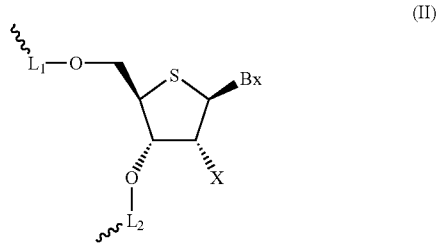

(II)

wherein Bx, L$_1$ and L$_2$ are defined herein.

In one embodiment, the composition comprises first and second oligonucleotides that are a complementary pair of siRNA oligonucleotides. In another embodiment the composition comprises first and second oligonucleotides that are an antisense/sense pair of oligonucleotides.

In one embodiment of the present invention, each of the first and second oligonucleotides comprising the composition has from 10 to about 40 nucleosides in length. In another embodiment of the present invention, each of the first and second oligonucleotides comprising the composition has from 18 to about 30 nucleosides in length. In a further embodiment of the present invention, each of the first and second oligonucleotides comprising the composition has from 18 to about 24 nucleosides in length.

In one embodiment of the present invention, the first oligonucleotide is an antisense oligonucleotide. In another embodiment of the present invention, the second oligonucleotide is a sense oligonucleotide. In a further embodiment of the present invention, the second oligonucleotide has a plurality of ribose nucleotide units.

In one embodiment of the present invention, the first oligonucleotide includes the nucleoside having the modification.

In one embodiment of the present invention, a process for the preparation of 1,4-anhydro-2-O-(2,4-dimethoxybenzoyl)-3,5-O-(1,1,3,3-tetraisopropyldisiloxane-1,3-diyl)$_4$-sulfinyl-D-ribitol is disclosed comprising:

preparing an oxidizing mixture by adding diethyl-L-tartrate to a solution of Ti(IV) isopropoxide in a suitable solvent followed by the addition of a suitable peroxide in said suitable solvent;

treating 1,4-anhydro-3,5-O-(1,1,3,3-tetraisopropyldisiloxane-1,3-diyl)-4-thio-D-ribitol in a suitable solvent with said oxidizing mixture to form 1,4-anhydro-2-O-(2,4-dimethoxybenzoyl)-3,5-O-(1,1,3,3-tetraisopropyldisiloxane-1,3-diyl)-4-sulfinyl-D-ribitol.

Yet another embodiment of the present invention includes processes of making any of the compounds of the present invention delineated herein.

BRIEF DESCRIPTION OF THE DRAWINGS

FIG. 1. depicts representative PTEN siRNA constructs of the present invention.

DETAILED DESCRIPTION OF THE INVENTION

Figure 2:
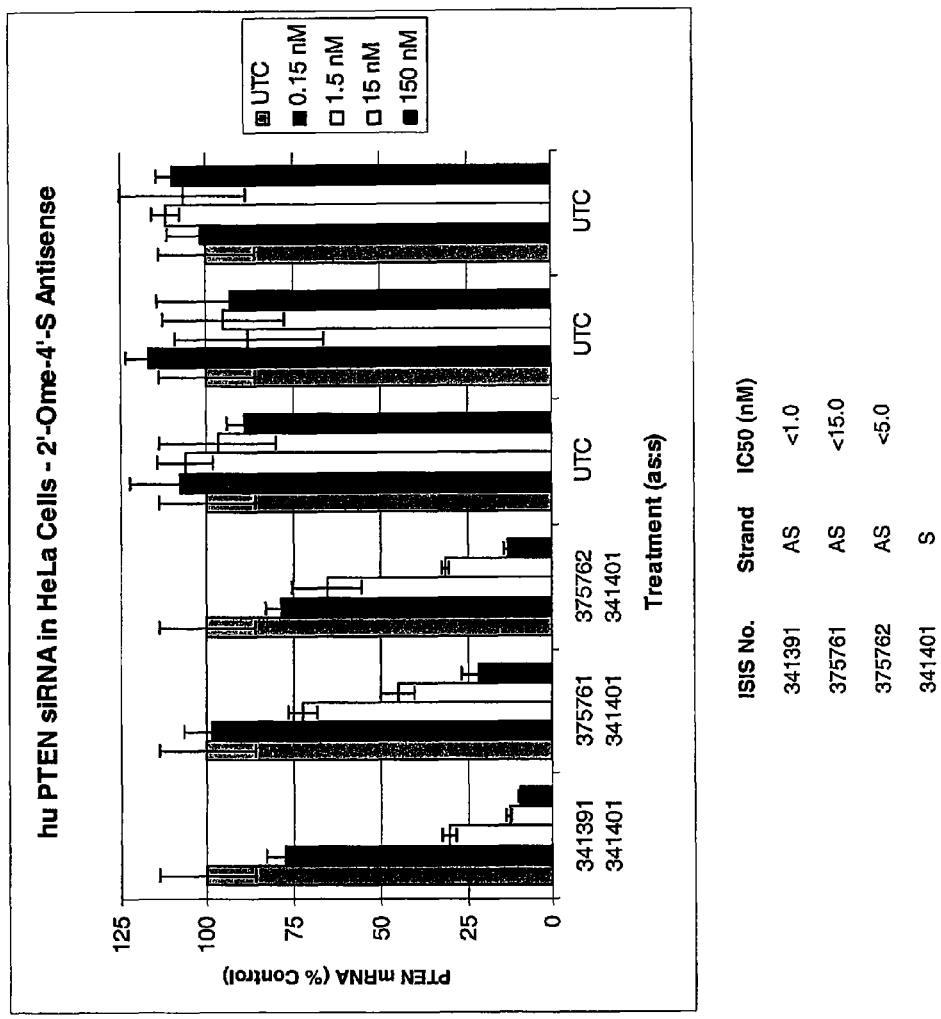
FIG. 2 depicts the reduction of human PTEN mRNA in HeLa cells achieved with select siRNAs of the present invention.

The present invention provides novel 4'-thionucleosides, single and double stranded oligomeric compounds prepared therefrom. The 4'-thionucleosides of the present invention are useful for chemically and enzymatically stabilizing oligomeric compounds in which they are incorporated, especially oligoribonucleotides. It is further believed that the 4'-thionucleosides of the present invention have the desired conformation to enhance the substrate specificity for mechanisms of action that utilize siRNA duplexes, micro RNAs and asRNA single stranded compounds. The oligomers of the present invention may also be useful as primers and probes in diagnostic applications.

The 4'-thionucleosides of the present invention are useful in a variety of motifs including but not limited to hemimers, gapmers, uniform, alternating with other chemistries. In conjunction with these motifs a wide variety of linkages can also be used including but not limited to phosphodiester and phosphorothioate linkages used uniformly or in combinations. The positioning of 4'-thio nucleosides and the use of linkage strategies can be easily optimized for the best activity for a particular target.

The 4'-thionucleosides of the present invention retain, for the most part, the chemical reactivity and steric positioning of functional groups found in natural ribonucleosides having similar conformations to corresponding ribonucleosides. Hence, when incorporated into oligonucleotides, the resulting 4'-thioRNA has a similar conformation to natural RNA with an expected increase in stability.

NMR experiments indicate a predominantly anti-conformation of the nucleobase as in unmodified ribonucleosides. Importantly the pKa values of nucleobases in 4'-thionucleosides are unchanged. This results in retention of the expected hybridization properties found in native RNA. Therefore, the 4'-thionucleosides are expected to have comparable hybridization and Tm properties with enhanced nuclease stability as compared to native phosphodiester linked RNA. The phosphodiester 4'-thionucleoside modified oligomeric compounds of the present invention are expected to have enhanced protein-binding, altered tissue-distribution, and pK properties.

4'-thionucleosides of the present invention are compounds of formula I, wherein X is selected from halogallyl, amino, azido, O-allyl, O—$CH_3$, O—$CH_2CH_2$—O—$CH_3$, O—$(CH_2$—$CH_2$—O—$N(R_m)(R_n)$ or O—$CH_2$—$C(=O)$—$N(R_m)(R_n)$, where each $R_m$ and $R_n$ is, independently, H, an amino protecting group or substituted or unsubstituted $C_1$-$C_{10}$ alkyl.

Oligomeric compounds and compositions having two strands have at least one modified nucleoside wherein X is selected from is halogen especially fluoro, alkyl especially methyl, alkenyl especially allyl, amino, substituted amino, azido, alkoxy especially —O-methyl or alkoxy substituted alkoxy especially —O—$CH_2CH_2$—O—$CH_3$.

Other suitable X substituent groups are aminooxy, substituted aminooxy, —O-acetamido, substituted —O-acetamido (—O—$CH_2C(=O)NR_mR_n$), aminoethyloxyethoxy, substituted aminoethyloxyethoxy(—O—$CH_2CH_2$—O—$CH_2CH_2$—$NR_mR_n$), aminooxyethyloxy and substituted aminooxyethyloxy(—O—$CH_2CH_2$—O—$NR_mR_n$).

Other suitable X substituents are selected from fluoro, allyl, amino, azido, O—$CH_3$, O—$CH_2CH_2$—O—$CH_3$, O—$(CH_2)_{ma}$—O—$N(R_m)(R_n)$ or O—$CH_2$—$C(=O)$—N$(R_m)(R_n)$, wherein:

each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester; and ma is from 1 to about 10.

The present invention also discloses a novel process for the preparation of 1,4-anhydro-2-O-(2,4-dimethoxybenzoyl)-3,5-O-(1,1,3,3-tetraisopropyldisiloxane-1,3-diyl)-4-sulfinyl-D-ribitol comprising:

preparing an oxidizing mixture by adding diethyl-L-tartrate to a solution of Ti(IV) isopropoxide in a suitable solvent followed by the addition of a suitable peroxide in a suitable solvent;

treating 1,4-anhydro-3,5-O-(1,1,3,3-tetraisopropyldisiloxane-1,3-diyl)-4-thio-D-ribitol in a suitable solvent with said oxidizing mixture to form 1,4-anhydro-2-O-(2,4-dimethoxybenzoyl)-3,5-O-(1,1,3,3-tetraisopropyl disiloxane-1,3-diyl)-4-sulfinyl-D-ribitol.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The methods of preparing oligomeric compounds of the present invention can also be applied in the areas of drug discovery and target validation. The present invention comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Definitions

General Chemistry

Listed below are definitions of various terms used to describe this invention. These definitions apply to the terms as they are used throughout this specification and claims, unless otherwise limited in specific instances, either individually or as part of a larger group. All terms appearing herein which are not specifically defined, shall be accorded the meaning that one of ordinary skill in the relevant art would attached to said term.

The terms "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_{12}$ alkyl radicals include, but are not limited to, ethyl, propyl, isopropyl, n-hexyl, octyl, decyl, dodecyl radicals.

An "aliphatic group" is an acyclic, non-aromatic moiety that may contain any combination of carbon atoms, hydrogen atoms, halogen atoms, oxygen, nitrogen, sulfur or other atoms, and optionally contain one or more units of unsaturation, e.g., double and/or triple bonds. An aliphatic group may be straight chained, or branched and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable substituents of the present invention include, but are not limited to, —F, —Cl, —Br, —I, —OH, protected hydroxy, aliphatic ethers, aromatic ethers, oxo, azido, —NO$_2$, —CN, —C$_1$-C$_{12}$-alkyl optionally substituted with halogen (such as perhaloalkyls), —C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$-heteroaryl, —CO$_2$-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$-C$_{12}$ alkenyl" or "C$_2$-C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$-C$_{12}$ alkenyl" or "C$_2$-C$_6$ alkenyl" group as previously defined, substituted by one, two, three or more substituents.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by one, two, three or more substituents.

The term "alkoxy," as used herein, refers to an aliphatic group, as previously defined, attached to the parent molecular moiety through an oxygen atom. Examples of alkoxy include, but are not limited to, methoxy, ethoxy, propoxy, isopropoxy, n-butoxy, sec-butoxy, tert-butoxy, n-pentoxy, neopentoxy and n-hexoxy.

The term "substituted alkoxy," as used herein, is an alkoxy group as defined herein substituted with one, two, three or more substituents as previously defined.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl or aromatic group substituted by one, two, three or more substituents.

The term "arylalkyl," as used herein, refers to an aryl group attached to the parent compound via a C$_1$-C$_3$ alkyl or C$_1$-C$_6$ alkyl residue. Examples include, but are not limited to, benzyl, phenethyl and the like.

The term "substituted arylalkyl," as used herein, refers to an arylalkyl group, as previously defined, substituted by one, two, three or more substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted alicyclic," as used herein, refers to an alicyclic group substituted by one, two, three or more substituents.

The term "heterocyclic," as used herein, refers to a non-aromatic ring, comprising three or more ring atoms, or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more substituents.

The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more substituents.

The term "alkylamino" refers to a group having the structure —NH($C_1$-$C_{12}$ alkyl).

The term "dialkylamino" refers to a group having the structure —N($C_1$-$C_{12}$ alkyl)($C_1$-$C_{12}$ alkyl) and cyclic amines. Examples of dialkylamino are, but not limited to, dimethylamino, diethylamino, methylethylamino, piperidino, morpholino and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, NHC(O)($C_1$-$C_{12}$ alkyl), N($C_1$-$C_{12}$ alkyl)C(O)($C_1$-$C_{12}$ alkyl) and the like.

The term "protecting groups," as used herein, refers to a labile chemical moiety which is known in the art to protect a hydroxyl or amino group against undesired reactions during synthetic procedures. After said synthetic procedure(s) the blocking group as described herein may be selectively removed. Blocking groups as known in the are described generally in T. H. Greene and P. G. M. Wuts, *Protective Groups in Organic Synthesis,* 3rd edition, John Wiley & Sons, New York (1999). Examples of hydroxyl blocking groups include, but are limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl(trityl), 4,4'-dimethoxytriphenylmethyl (DMT), substituted or unsubstituted pixyl, tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl blocking groups for the present invention are DMT and substituted or unsubstituted pixyl.

Amino blocking groups as known in the are described generally in T. H. Greene and P. G. M. Wuts, *Protective Groups in Organic Synthesis,* 3rd edition, John Wiley & Sons, New York (1999). Examples of amino blocking groups include, but are not limited to, t-butoxycarbonyl, 9-fluorenylmethoxycarbonyl, benzyloxycarbonyl, and the like.

The term "protected hydroxyl group," as used herein, refers to a hydroxyl group protected with a protecting group, as defined above.

The term "acyl" includes residues derived from substituted or unsubstituted acids including, but not limited to, carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al, Vol. II, in the Techniques of Chemistry Series, John Wiley & Sons, NY, 1986. Aprotic solvents useful in the processes of the present invention includes, but are not limited to, toluene, acetonitrile, DMF, THF, dioxane, MTBE, diethylether, NMP, acetone, hydrocarbons, and haloaliphatics.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Gene Modulation

As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In one embodiment of the invention, the target nucleic acid is a messenger RNA. In another embodiment, the degradation of the targeted messenger RNA is facilitated by a RISC complex that is formed with oligomeric compounds of the invention. In another embodiment, the degradation of the targeted messenger RNA is facilitated by a nuclease such as RNaseH.

The hybridization of an oligomeric compound of this invention with its target nucleic acid is generally referred to as "antisense". Consequently, one mechanism in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently suitable to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the desired form of modulation of expression and mRNA is often a desired target nucleic acid.

The compounds and methods of the present invention are also useful in the study, characterization, validation and modulation of small non-coding RNAs. These include, but are not limited to, microRNAs (mRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like mRNAs, have been shown to be involved in developmental timing regulation. Other non-coding small RNAs are involved in events as diverse as cellular splicing of transcripts, translation, transport, and chromosome organization.

As modulators of small non-coding RNA function, the compounds of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compounds of the present invention can be modified in order to optimize their effects in certain cellular compartments, such as the cytoplasm, nucleus, nucleolus or mitochondria.

The compounds of the present invention can further be used to identify components of regulatory pathways of RNA processing or metabolism as well as in screening assays or devices.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds are routinely prepared linearly but can be joined or otherwise prepared to be circular and may also include branching. Oligomeric compounds can include double stranded constructs such as for example two strands hybridized to form double stranded compounds. The double stranded compounds can be linked or separate and can include overhangs on the ends. In general, an oligomeric compound comprises a backbone of linked momeric subunits where each linked momeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonulceotides. Such non-naturally occurring oligonucleotides are often desired over the naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Further included in the present invention are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In addition to the modifications described above, the nucleosides of the oligomeric compounds of the invention can have a variety of other modification so long as these other modifications either alone or in combination with other nucleosides enhance one or more of the desired properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

The term "nucleobase," as used herein, is intended to by synonymous with "nucleic acid base or mimetic thereof." In general, a nucleobase is any substructure that contains one or more atoms or groups of atoms capable of hydrogen bonding to a base of an oligonucleotide.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified Nucleobases

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

The term "universal base" as used herein, refers to a monomer in a first sequence that can pair with a naturally occuring base, i.e A, C, G, T or U at a corresponding position in a second sequence of a duplex in which one or more of the following is true: (1) there is essentially no pairing between the two; or (2) the pairing between them occurs non-discriminantly with each of the naturally occurring bases and without significant destabilization of the duplex.

For examples of universal bases see Survey and summary: the applications of universal DNA base analogs. Loakes, D. *Nucleic Acids Research*, 2001, 29, 12, 2437-2447.

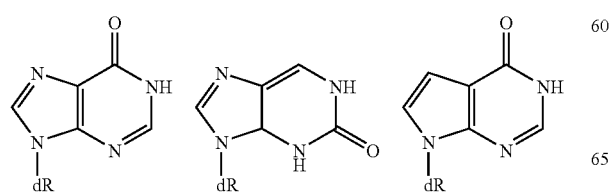

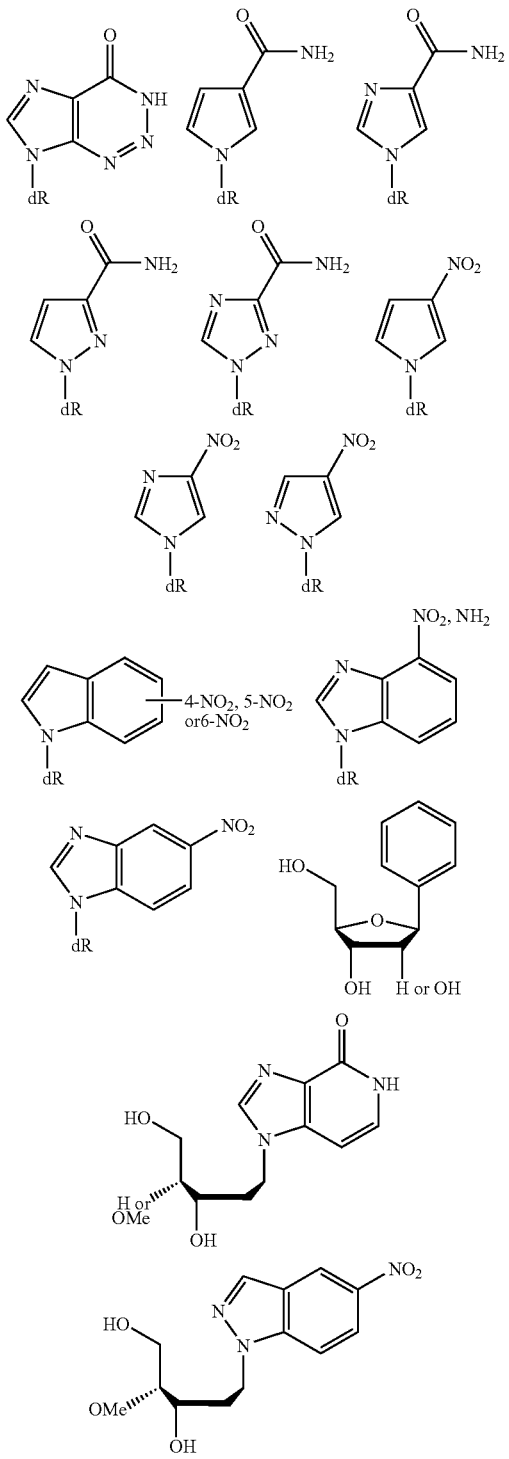

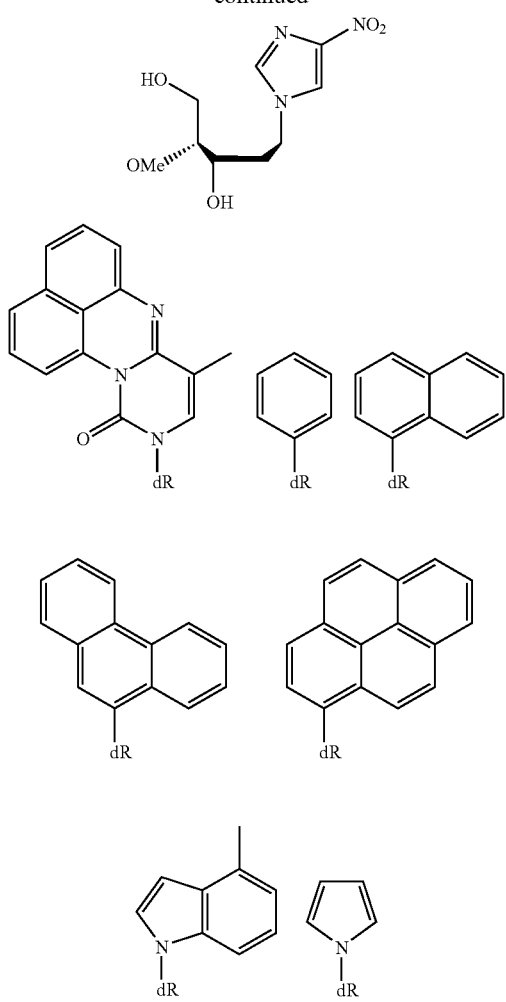

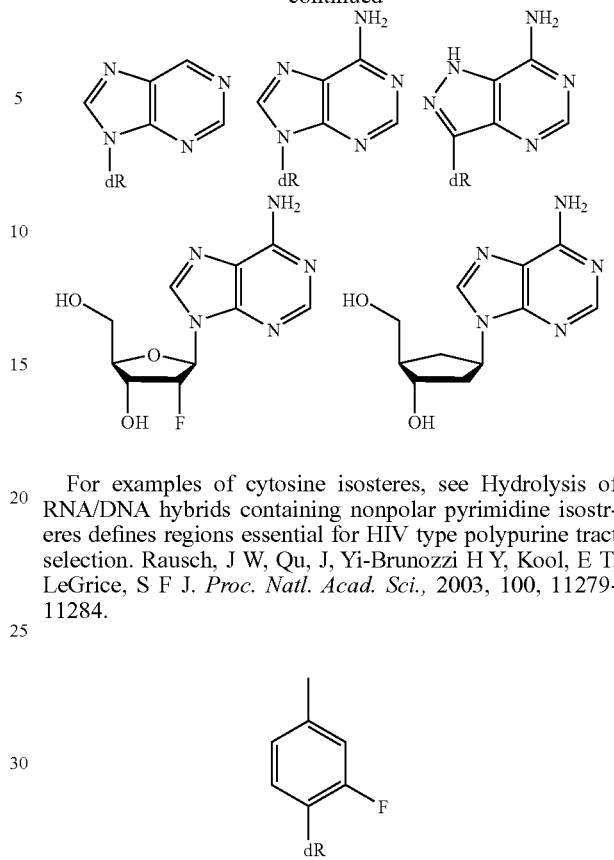

For examples of cytosine isosteres, see Hydrolysis of RNA/DNA hybrids containing nonpolar pyrimidine isostreres defines regions essential for HIV type polypurine tract selection. Rausch, J W, Qu, J, Yi-Brunozzi H Y, Kool, E T, LeGrice, S F J. *Proc. Natl. Acad. Sci.*, 2003, 100, 11279-11284.

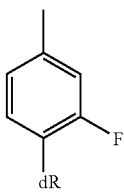

For examples of guanosine isosteres, see A highly effective nonpolar isostere of doeoxguanosine: synthesis, structure, stacking and base pairing. O'Neil, B M, Ratto, J E, Good, K L, Tahmassebi, D C, Helquist, S A, Morales, J C, Kool, E T. *J. Org. Chem.*, 2002, 67, 5869-5875.

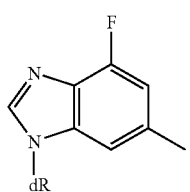

For examples of thymidine isosteres, see A thymidine triphosphate shape analog lacking Watson-Crick pairing ability is replicated with high sequence selectivity. Moran, S, Ren, R X-F, Kool, E T. *Proc. Natl. Acad. Sci.*, 1997, 94, 10506-10511 or Difluorotoluene, a nonpolar isostere for thymidine, codes specifically and efficiently for adenine in DNA replication. *J. Am. Chem. Soc.* 1997, 119, 2056-2057.

The term "hydrophobic base" as used herein, refers to a monomer in a first sequence that can pair with a naturally occuring base, i.e A, C, G, T or U at a corresponding position in a second sequence of a duplex in which one or more of the following is true: (1) the hydrophobic base acts as a non-polar close size and shape mimic (isostere) of one of the naturally occurring nucleosides; or (2) the hydrophobic base lacks all hydrogen bonding functionality on the Watson-Crick pairing edge.

For examples of adenine isosteres, see Probing the requirements for recognition and catalysis in Fpg and MutY with nonpolar adenine isosteres. Francis, A W, Helquist, S A, Kool, E T, David, S S. *J. Am. Chem. Soc.*, 2003, 125, 16235-16242 or Structure and base pairing properties of a replicable nonpolar isostere for deoxyadenosine. Guckian, K M, Morales, J C, Kool, E T. *J. Org. Chem.*, 1998, 63, 9652-96565.

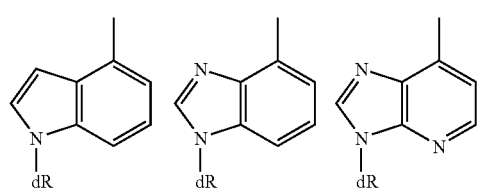

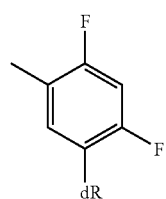

The term "promiscuous base" as used herein, refers to a monomer in a first sequence that can pair with a naturally occuring base, i.e A, C, G, T or U at a corresponding position in a second sequence of a duplex in which the promiscuous base can pair non-discriminantly with more than one of the naturally occurring bases, i.e. A, C, G, T, or U. For an example, see Polymerase recognition of synthetic oligodeoxyribonucleotides incorporating degenerate pyrimidine and purine bases. Hill, F.; Loakes, D.; Brown, D. M. *Proc. Natl. Acad. Sci.,* 1998, 95, 4258-4263.

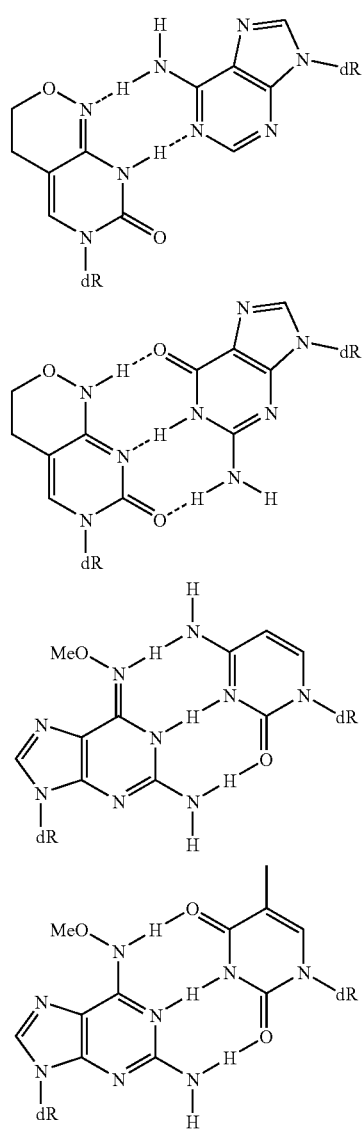

The term "size expanded base" as used herein, refers to analogs of naturally occurring nuceobases that are larger in size and retain their Watson-Crick pairing ability. For examples see A four-base paired genetic helix with expanded size. Liu, B. Gao, J. Lynch, S R, Saito, D, Maynard, L, Kool, E T., *Science,* 2003, 302, 868-871 and Toward a new genetic system with expanded dimension: size expanded analogues of deoxyadenosine and thymidine. Liu, H. Goa, J. Maynard, Y. Saito, D, Kool, E T, *J. Am. Chem. Soc.* 2004, 126, 1102-1109.

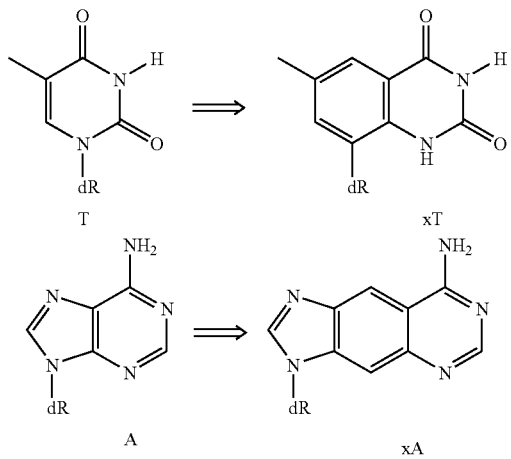

The term "fluorinated nucleobase" as used herein, refers to a nucleobase or nucleobase analog, wherein one or more of the aromatic ring substituents is a fluoroine atom. It may be possible that all of the ring substituents are fluoroine atoms. For examples of fluorinated nucleobases see fluorinated DNA bases as probes of electrostatic effects in DNA base stacking. Lai, J S, QU, J, Kool, E T, *Angew. Chem. Int. Ed.,* 2003, 42, 5973-5977 and Selective pairing of polyfluorinated DNA bases, Lai, J S, Kool, E T, *J. Am. Chem. Soc.,* 2004, 126, 3040-3041 and The effect of universal fluorinated nucleobases on the catalytic activity of ribozymes, Kloppfer, A E, Engels, J W, *Nucleosides, Nucleotides & Nucleic Acids,* 2003, 22, 1347-1350 and Synthesis of 2'aminoalkyl-substituted fluorinated nucleobases and their influence on the kinetic properties of hammerhead ribozymes, Klopffer, A E, Engels, J W, *ChemBioChem.,* 2003, 5, 707-716.

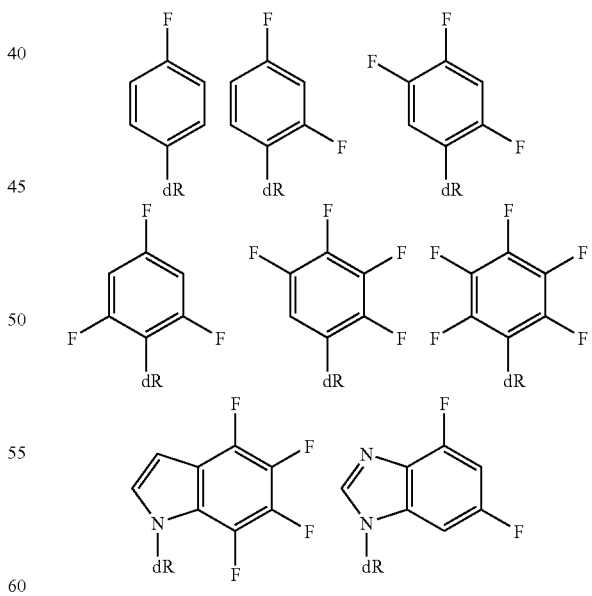

In some embodiments of the invention, oligomeric compounds, e.g. oligonucleotides, are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

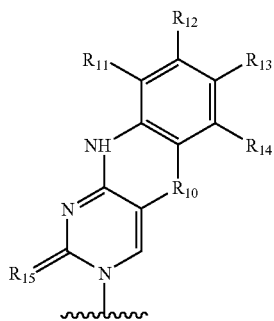

Representative cytosine analogs that make 3 hydrogen bonds with a guanosine in a second oligonucleotide include 1,3-diazaphenoxazine-2-one ($R_{10}=O$, $R_{11}$-$R_{14}=H$) [Kurchavov, et al., *Nucleosides and Nucleotides*, 1997, 16, 1837-1846], 1,3-diazaphenothiazine-2-one ($R_{10}=S$, $R_{11}$-$R_{14}=H$), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}=O$, $R_{11}$-$R_{14}=F$) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}=O$, $R_{11}=-O-(CH_2)_2-NH_2$, $R_{12-14}=H$) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

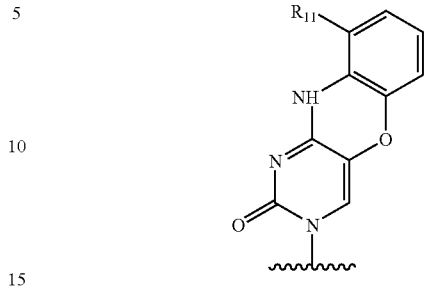

Wherein $R_{11}$, includes $(CH_3)_2N-(CH_2)_2-O-$; $H_2N-(CH_2)_3-$; $Ph-CH_2-O-C(=O)-N(H)-(CH_2)_3-$; $H_2N-$; $Fluorenyl-CH_2-O-C(=O)-N(H)-(CH_2)_3-$; $Phthalimidyl-CH_2-O-C(=O)-N(H)-(CH_2)_3-$; $Ph-CH_2-O-C(=O)-N(H)-(CH_2)_2-O-$; $Ph-CH_2-O-C(=O)-N(H)-(CH_2)_3-O-$; $(CH_3)_2N-N(H)-(CH_2)_2-O-$; $Fluorenyl-CH_2-O-C(=O)-N(H)-(CH_2)_2-O-$; $Fluorenyl-CH_2-O-C(=O)-N(H)-(CH_2)_3-O-$; $H_2N-(CH_2)_2-O-CH_2-$; $N_3-(CH_2)_2-O-CH_2-$; $H_2N-(CH_2)_2-O-$, and $NH_2C(=NR)NH-$.

Also disclosed are tricyclic heterocyclic compounds of the formula:

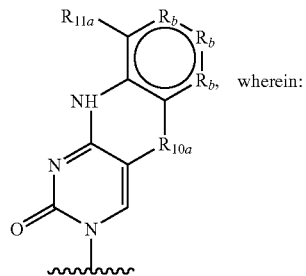

wherein:

$R_{10a}$ is O, S or N—$CH_3$; $R_{11a}$ is $A(Z)_{x1}$, wherein A is a spacer and Z independently is a label bonding group optionally bonded to a detectable label, but $R_{11a}$ is not amine, protected amine, nitro or cyano; and $R_b$ is independently —CH=, —N=, —C($C_{1-8}$ alkyl)= or —C(halogen)=, but no adjacent $R_b$ are both —N=, or two adjacent $R_b$ are taken together to form a ring having the structure:

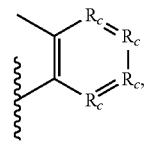

where $R_c$ is independently —CH=, —N=, —C($C_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

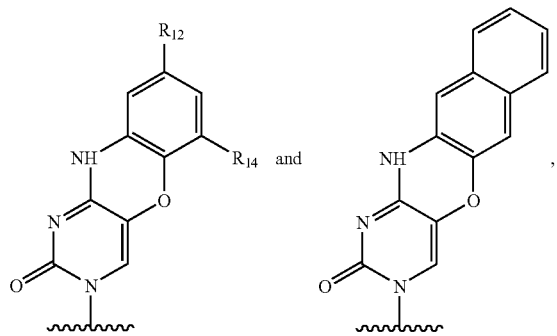

wherein $R_{14}$ is $NO_2$ or both $R_{14}$ and $R_{12}$ are independently —$CH_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety (hereinafter referred to as the "'257, '177 and '269 patents").

Further tricyclic heterocyclic compounds amenable to the present invention also disclosed in the '257, '177 and '269 patents include those having the formula:

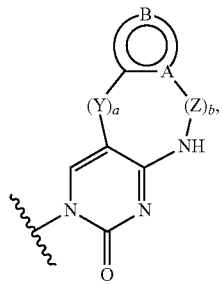

wherein a and b are independently 0 or 1 with the total of a and b being 0 or 1; A is N, C or CH; Y is S, O, C=O, NH or $NCH_2$, $R^6$; Z is C=O; B is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is substituted with $R^{20}$ or =O; or Z is taken together with A to form an aryl ring structure comprising 6 ring atoms wherein the aryl ring carbon atoms are unsubstituted with other than H or at least 1 nonbridging ring carbon atom is substituted with $R^6$ or =O; $R^6$ is independently H, $C_{1-6}$ alkyl, $C_{2-6}$alkenyl, $C_{2-6}$ alkynyl, $NO_2$, $N(R^3)_2$, CN or halo, or an $R^6$ is taken together with an adjacent B group $R^6$ to complete a phenyl ring; $R^{20}$ is, independently, H, $C_{1-6}$ alkyl, $C_{2-6}$ alkyl, $C_{2-6}$alkenyl, $C_{2-6}$ alkynyl, $NO_2$, $N(R^{21})_2$, CN, or halo, or an $R^{20}$ is taken together with an adjacent $R^{20}$ to complete a ring containing 5 or 6 ring atoms, and tautomers, solvates and salts thereof; $R^{21}$ is, independently, H or a protecting group; $R^3$ is a protecting group or H; and tautomers, solvates and salts thereof.

More specific examples of bases included in the "257, 177 and 269" Patents are compounds of the formula:

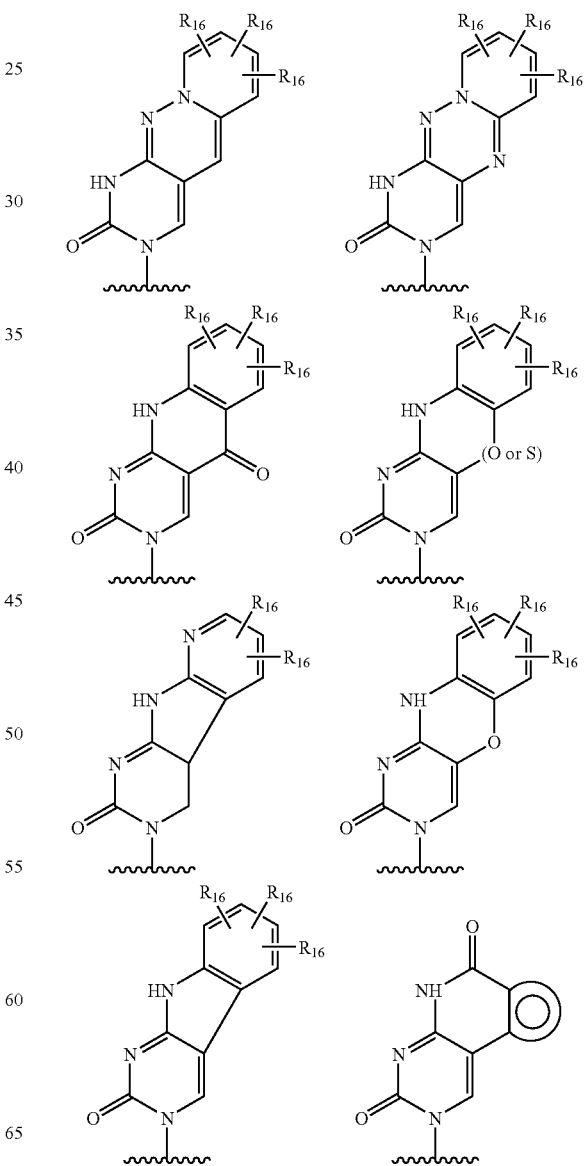

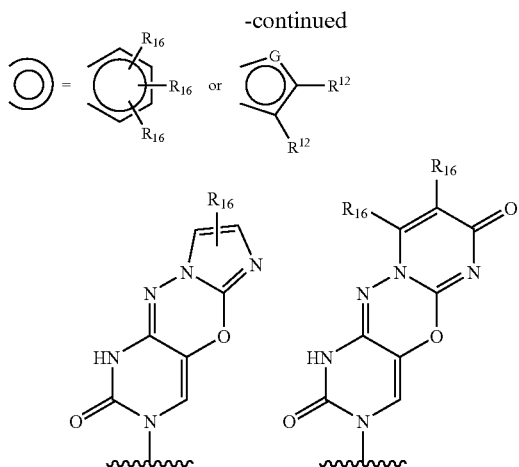

wherein each $R_{16}$, is, independently, selected from hydrogen and various substituent groups. Further polycyclic base moieties having the formula:

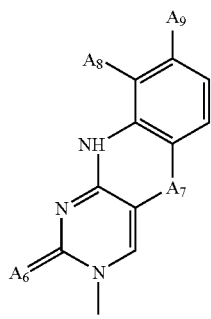

wherein: $A_6$ is O or S; $A_7$ is $CH_2$, N—$CH_3$, O or S; each $A_8$ and $A_9$ is hydrogen or one of $A_8$ and $A_9$ is hydrogen and the other of $A_8$ and $A_9$ is selected from the group consisting of:

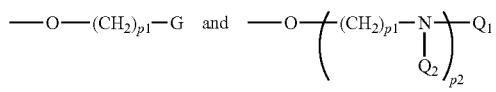

wherein: G is —CN, —$OA_{10}$, —$SA_{10}$, —N(H)$A_{10}$, —ON(H)$A_{10}$ or —C(=NH)N(H)$A_{10}$; $Q_1$ is H, —NH$A_{10}$, —C(=O)N(H)$A_{10}$, —C(=S)N(H)$A_{10}$ or —C(=NH)N(H)$A_{10}$; each $Q_2$ is, independently, H or Pg; $A_{10}$ is H, Pg, substituted or unsubstituted $C_1$-$C_{10}$ alkyl, acetyl, benzyl, —$(CH_2)_{p3}NH_2$, —$(CH_2)_{p3}$N(H)Pg, a D or L α-amino acid, or a peptide derived from D, L or racemic α-amino acids; Pg is a nitrogen, oxygen or thiol protecting group; each p1 is, independently, from 2 to about 6; p2 is from 1 to about 3; and p3 is from 1 to about 4; are disclosed in U.S. patent application Ser. No. 09/996,292 filed Nov. 28, 2001, which is commonly owned with the instant application, and is herein incorporated by reference.

Some particularly useful oligomeric compounds of the invention contain at least one nucleoside having one, two, three, or more aliphatic substituents, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other particularly advantageous 2'-modifications include 2'-methoxy(2'-O—$CH_3$), 2'-aminopropoxy(2'-OCH$_2$CH$_2$CH$_2$NH$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531; 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula are disclosed in co-owned U.S. patent application Ser. No. 09/349,040, entitled "Functionalized Oligomers", filed Jul. 7, 1999, issue fee paid on Oct. 23, 2002.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The oligomeric compounds in accordance with this invention can comprise from about 8 to about 80 nucleobases (i.e., from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In another embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In another embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length, or any range therewithin.

Suitable oligomeric compounds are oligonucleotides from about 12 to about 50 nucleobases or from about 15 to about 30 nucleobases.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally desired. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds which are chimeric oligomeric compounds. "Chimeric" oligomeric compounds or "chimeras," in the context of this invention, are oligomeric compounds which contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomer Mimetics

Another group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

Another modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be preferably a methylene, ethylene (referred to in the art as ENA), or $(-CH_2-)_n$ group bridging the 2' oxygen atom and the 4' carbon atom wherein n is 1 to 10 (Singh et al., Chem. Commun., 1998, 4, 455-456). LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

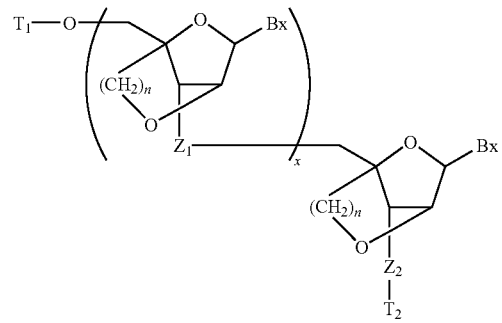

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNAs have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

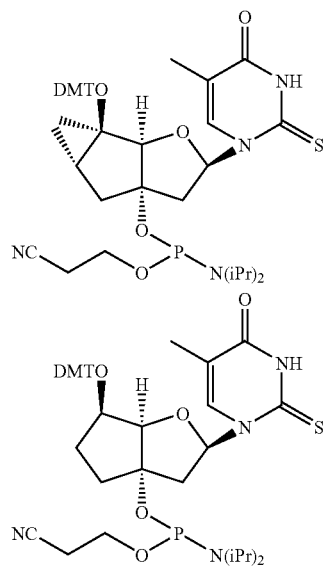

(see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

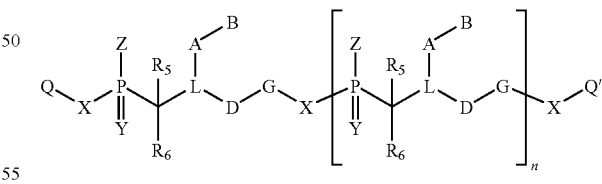

Another oligonucleotide mimetic has been reported wherein the furanosyl ring has been replaced by a cyclobutyl moiety.

Modified Internucleoside Linkages

Specific examples of antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain oligomeric compounds of the invention can also have one or more modified internucleoside linkages. One phosphorus containing modified internucleoside linkage is the phosphorothioate internucleoside linkage.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphos-phonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In some embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Suitable amide internucleoside linkages are disclosed in the above referenced U.S. Pat. No. 5,602,240.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugars

Oligomeric compounds of the invention may also contain one or more substituted sugar moieties. Suitable oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$]$_2$, where n and m are from 1 to about 10. Other oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy(2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. Another modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxyethyl or 2'-DMAEOE), i.e., 2'-O—$CH_2$—O—$CH_2$—N($CH_3$)$_2$.

Other suitable sugar substituent groups include methoxy (—O—$CH_3$), aminopropoxy (—O$CH_2CH_2CH_2NH_2$), allyl (—$CH_2$—CH=$CH_2$), —O-allyl(—O—$CH_2$—CH=$CH_2$) and fluoro (F). 2'-Sugar substituent groups may be in the arabino (up) position or ribo (down) position. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety. Further representative sugar substituent groups include groups of formula Ia or Ib:

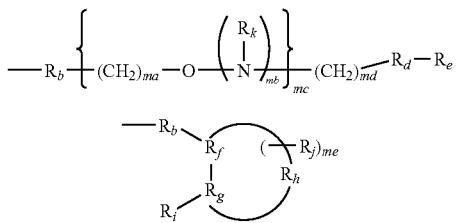

Ia

Ib wherein:
$R_b$ is O, S or NH;
$R_d$ is a single bond, O, S or C(=O);
$R_e$ is $C_1$-$C_{10}$ alkyl, $N(R_k)(R_m)$, $N(R_k)(R_n)$, $N=C(R_p)(R_q)$, $N=C(R_p)(R_r)$ or has formula Ic;

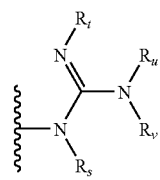

(Ic)

$R_p$ and $R_q$ are each independently hydrogen or $C_1$-$C_{10}$ alkyl;
$R_r$ is —$R_x$—$R_y$;
each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, $R_u$ and $R_v$, together form a phthalimido moiety with the nitrogen atom to which they are attached;
each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;
$R_k$ is hydrogen, an amino protecting group or —$R_x$—$R_y$;
$R_p$ is hydrogen, an amino protecting group or —$R_x$—$R_y$;
$R_x$ is a bond or a linking moiety;
$R_y$ is a chemical functional group, a conjugate group or a solid support medium;
each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;
or $R_m$ and $R_n$, together, are an amino protecting group, are joined in a ring structure that optionally includes an additional heteroatom selected from N and O or are a chemical functional group;
$R_i$ is $OR_z$, $SR_z$, or $N(R_z)_2$;
each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;
$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;
$m_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula Ia are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula Ib are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Sugar substituent groups also include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nH)]_2$, where n and m are from 1 to about 10.

Representative guanidino substituent groups that are shown in formula Ic are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Conjugates

Another substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Scheme 1

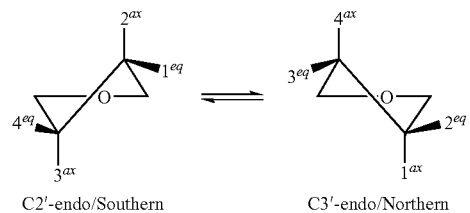

C2'-endo/Southern      C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in Scheme 1a, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Scheme Ia. These examples are meant to be representative and not exhaustive.

Scheme 1

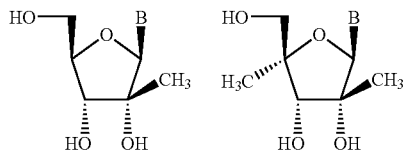

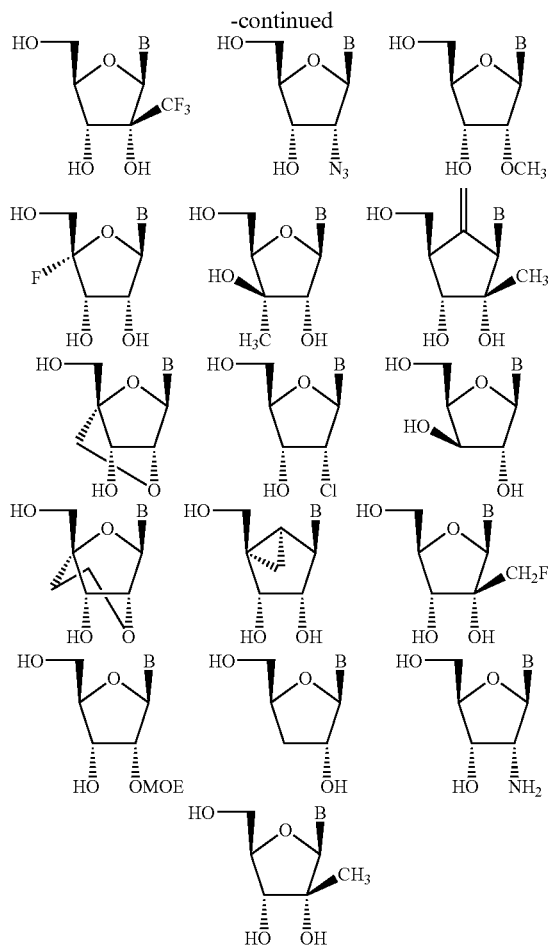

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/ substrates for RNA dependent RNA polymerases (for example HCV NS5B.

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacyl.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy(2'-MOE, 2'-OCH$_2$CH$_2$OCH$_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

In all the preceding formulae, the squiggle (~) indicates a bond to an oxygen or sulfur of the 5'-phosphate. Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

Oligonucleotides are generally prepared either in solution or on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support medium can be soluble or insoluble, or may possess variable solubility in different solvents to allow the growing support bound polymer to be either in or out of solution as desired. Traditional support medium such as solid support media are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support medium is intended to include all forms of support known to one of ordinary skill in the art for the synthesis of oligomeric compounds and related compounds such as peptides. Some representative support medium that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett.,* 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support medium, polyethylene glycol PEG's (see Bonora et al., Organic Process Research & Development, 2000, 4, 225-231).

Further support medium amenable to the present invention include without limitation PEPS support a polyethylene (PE) film with pendant long-chain polystyrene (PS) grafts (molecular weight on the order of 10$^6$, (see Berg, et al., *J. Am. Chem. Soc.,* 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell-plates have not indicated any limitations of the synthetic efficacy.

Further support medium amenable to the present invention include without limitation particles based upon copolymers of dimethylacrylamide cross-linked with N,N'-bisacryloyl-ethylenediamine, including a known amount of N-tertbutoxy-carbonyl-beta-alanyl-N,N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin I 538 (1981)).

Further support medium amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid support media other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175-178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.*, 1989, 54, 1746). Support mediumted synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and nucleotides bearing the appropriate activated phosphite moiety, i.e. an "activated phosphorous group" (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. No. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The term "linking moiety," as used herein is generally a di-functional group, covalently binds the ultimate 3'-nucleoside (and thus the nascent oligonucleotide) to the solid support medium during synthesis, but which is cleaved under conditions orthogonal to the conditions under which the 5'-protecting group, and if applicable any 2'-protecting group, are removed. Suitable linking moietys include, but are not limited to, a divalent group such as alkylene, cycloalkylene, arylene, heterocyclyl, heteroarylene, and the other variables are as described above. Exemplary alkylene linking moietys include, but are not limited to, $C_1$-$C_{12}$ alkylene (e.g. preferably methylene, ethylene (e.g. ethyl-1,2-ene), propylene (e.g. propyl-1,2-ene, propyl-1,3-ene), butylene, (e.g. butyl-1,4-ene, 2-methylpropyl-1,3-ene), pentylene, hexylene, heptylene, octylene, decylene, dodecylene), etc. Exemplary cycloalkylene groups include $C_3$-$C_{12}$ cycloalkylene groups, such as cyclopropylene, cyclobutylene, cyclopentanyl-1,3-ene, cyclohexyl-1,4-ene, etc. Exemplary arylene linking moietys include, but are not limited to, mono- or bicyclic arylene groups having from 6 to about 14 carbon atoms, e.g. phenyl-1,2-ene, naphthyl-1,6-ene, napthyl-2,7-ene, anthracenyl, etc. Exemplary heterocyclyl groups within the scope of the invention include mono- or bicyclic aryl groups having from about 4 to about 12 carbon atoms and about 1 to about 4 hetero atoms, such as N, O and S, where the cyclic moieties may be partially dehydrogenated. Certain heteroaryl groups that may be mentioned as being within the scope of the invention include: pyrrolidinyl, piperidinyl (e.g. 2,5-piperidinyl, 3,5-piperidinyl), piperazinyl, tetrahydrothiophenyl, tetrahydrofuranyl, tetrahydro quinolinyl, tetrahydro isoquinolinyl, tetrahydroquinazolinyl, tetrahydroquinoxalinyl, etc. Exemplary heteroarylene groups include mono- or bicyclic aryl groups having from about 4 to about 12 carbon atoms and about 1 to about 4 hetero atoms, such as N, O and S. Certain heteroaryl groups that may be mentioned as being within the scope of the invention include: pyridylene (e.g. pyridyl-2,5-ene, pyridyl-3,5-ene), pyrimidinyl, thiophenyl, furanyl, quinolinyl, isoquinolinyl, quinazolinyl, quinoxalinyl, etc.

Suitable reagents for introducing the group HOCO-Q-CO include diacids ($HO_2C$-Q-$CO_2H$). Particularly suitable diacids include malonic acid (Q is methylene), succinic acid (Q is 1,2-ethylene), glutaric acid, adipic acid, pimelic acid, and phthalic acid. Other suitable reagents for introducing HOCO-Q-CO above include diacid anhydrides. Particularly suitable diacid anhydrides include malonic anhydride, succinic anhydride, glutaric anhydride, adipic anhydride, pimelic anhydride, and phthalic anhydride. Other suitable reagents for introducing HOCO-Q-CO include diacid esters, diacid halides, etc. One especially preferred reagent for introducing HOCO-Q-CO is succinic anhydride.

The compound of formula may be linked to a support via terminal carboxylic acid of the HOCO-Q-CO group, via a reactive group on the support medium. In some embodiments, the terminal carboxylic acid forms an amide linkage with an amine reagent on the support surface. In other embodiments, the terminal carboxylic acid forms an ester with an OH group on the support medium. In some embodiments, the terminal carboxylic acid may be replaced with a terminal acid halide, acid ester, acid anhydride, etc. Specific acid halides include carboxylic chlorides, bromides and iodides. Specific esters include methyl, ethyl, and other $C_1$-$C_{10}$ alkyl esters. Specific anhydrides include formyl, acetyl, propanoyl, and other $C_1$-$C_{10}$ alkanoyl esters.

The present invention also encompasses the preparation of oligomeric compounds incorporating at least one 2'-O-protected nucleoside into the oligomeric compounds delineated herein. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention. In general, a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for the more specialized protecting groups used for the protection of 2'-hydroxyl groups which will give the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)phenyl] 4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—$CH_2$—O—$Si(iPr)_3$, TOM). One 2'-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl(2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1 (2-fluorophenyl)$_4$-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

Targets of the Invention

"Targeting" an antisense oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts". It is also known that introns can be effectively targeted using antisense oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the antisense oligomeric compounds hybridize are hereinbelow referred to as "suitable target segments." As used herein the term "suitable target segment" is defined as at least an 8-nucleobase portion of a target region to which an active antisense oligomeric compound is targeted. While not wishing to be bound by theory, it is presently believed that these target segments represent portions of the target nucleic acid which are accessible for hybridization.

Exemplary antisense oligomeric compounds include oligomeric compounds that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense compound which is specifically hybridizable to the target nucleic acid and continuing until the oligonucleotide contains from about 8 to about 80 nucleobases). Similarly, antisense oligomeric compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains from about 8 to about 80 nucleobases). One having skill in the art armed with the antisense compounds illustrated herein will be able, without undue experimentation, to identify further antisense compounds.

Once one or more target regions, segments or sites have been identified, antisense oligomeric compounds are chosen which are sufficiently complementary to the target, i.e., hybridize sufficiently well and with sufficient specificity, to give the desired effect.

In accordance with one embodiment of the present invention, a series of nucleic acid duplexes comprising the antisense oligomeric compounds of the present invention and their complements can be designed for a specific target or targets. The ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini.

For example, a duplex comprising an antisense oligomeric compound having the sequence CGAGAGGCGGACGG-GACCG (SEQ ID NO:1) and having a two-nucleobase overhang of deoxythymidine(dT) would have the following structure:

annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexs are evaluated for their ability to modulate target expression. When cells reach 80% confluency, they are treated with synthetic duplexs comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "suitable target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a suitable target segment. The screening method comprises the steps of contacting a suitable target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

The suitable target segments of the present invention may also be combined with their respective complementary antisense oligomeric compounds of the present invention to form stabilized double-stranded (duplexed) oligonucleotides.

Hybridization

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and

```
cgagaggcggacgggaccgdTdT   Antisense Strand   (SEQ ID NO: 2)
||||||||||||||||||
dTdTgctctccgcctgccctggc   Complement Strand  (SEQ ID NO: 3)
```

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of thymine are complementary nucleobases which pair through the formation of hydrogen bonds. Hybridization can occur under varying circumstances.

An antisense oligomeric compound is specifically hybridizable when binding of the compound to the target nucleic acid interferes with the normal function of the target nucleic acid to cause a loss of activity, and there is a sufficient degree of complementarity to avoid non-specific binding of the antisense oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The antisense oligomeric compounds of the present invention can comprise at least about 70%, at least about 80%, at least about 90%, at least about 95%, or at least about 99% sequence complementarity to a target region within the target nucleic acid sequence to which they are targeted. For example, an antisense oligomeric compound in which 18 of 20 nucleobases of the antisense oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Screening and Target Validation

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The suitable target segments of the present invention may also be combined with their respective complementary antisense oligomeric compounds of the present invention to form stabilized double-stranded (duplexed) oligonucleotides. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds of the present invention can also be applied in the areas of drug discovery and target validation. The present invention comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Kits, Research Reagents, Diagnostics, and Therapeutics

The oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense oligomeric compounds are compared to control cells or tissues not treated with antisense oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The oligomeric compounds of the invention are useful for research and diagnostics, because these oligomeric compounds hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

For therapeutics, an animal, such as a human, suspected of having a disease or disorder which can be treated by modulating the expression of a selected protein is treated by administering antisense oligomeric compounds in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In some embodiments, the activity or expression of a protein in an animal or cell is inhibited by at least about 10%, at least about 20%, at least about 30%, at least about 40%, at least about 50%, at least about 60%, at least about 70%, at least about 80%, at least about 90%, at least about 95%, at least about 99%, or by 100%.

For example, the reduction of the expression of a protein may be measured in serum, adipose tissue, liver or any other body fluid, tissue or organ of the animal. The cells contained within the fluids, tissues or organs being analyzed can contain a nucleic acid molecule encoding a protein and/or the protein itself.

The oligomeric compounds of the invention can be utilized in pharmaceutical compositions by adding an effective amount of an oligomeric compound to a suitable pharmaceutically acceptable diluent or carrier. Use of the oligomeric compounds and methods of the invention may also be useful prophylactically.

In another embodiment, the present invention provides for the use of a compound(s) of the invention in the manufacture of a medicament for the treatment of any and all diseases and conditions disclosed herein.

Formulations

The antisense oligomeric compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein in its entirety.

While the present invention has been described with specificity in accordance with certain of its embodiments, the following examples serve only to illustrate the invention and are not intended to limit the same.

Synthetic Schemes

The compounds and processes of the present invention will be better understood in connection with the following synthetic schemes which are illustrative of the methods by which the compounds of the invention may be prepared.

Scheme 2: Synthesis of a thio-sugar

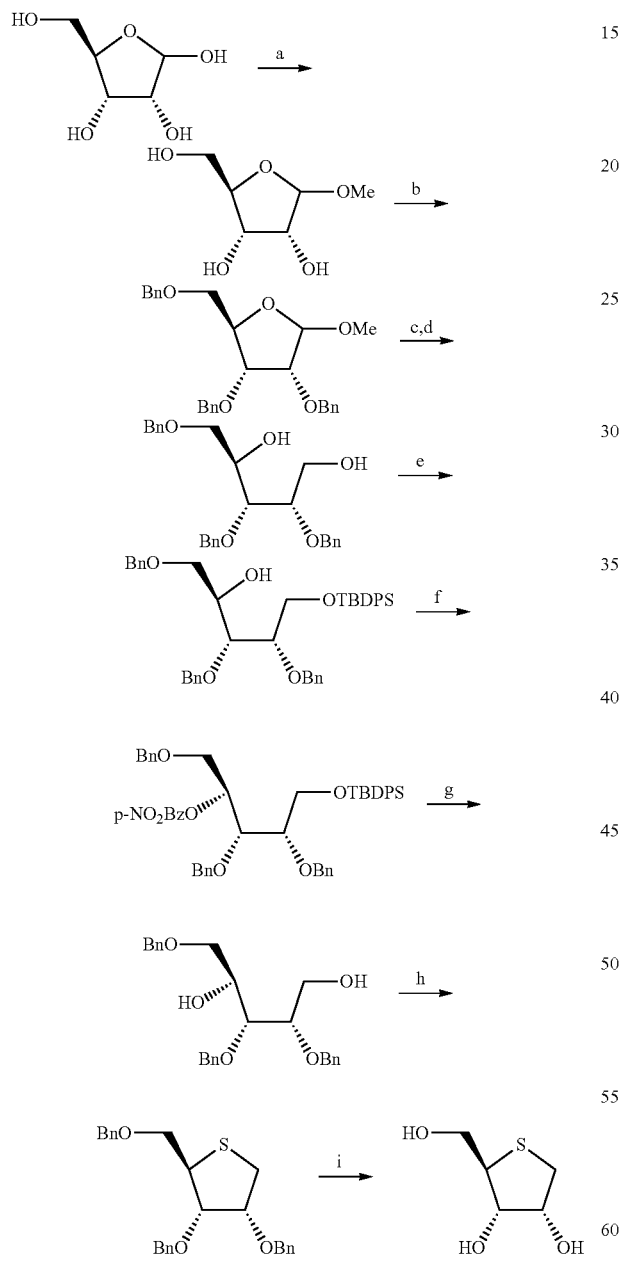

a) 0.5% HCl in Methanol; b) BnBr, NaH, DMF; c) 2N HCl, reflux; d) NaBH4; e) TBDPS-Cl, pyridine; f) p-nitrobenzoic acid, PPh3, diisopropylazodicarboxylate, THF; g) NaOMe, then TREAT•HF; h) MsCl, pyridine, then Na2S•9H2O, DMF, 100° C.; i) BCl3, dichloromethane, -98° C. See Naka et al. (2000) *J. Am. Chem. Soc.* 122, 7233-7243

Scheme 3: Synthesis of 4'Thio-U Phosphoramidite

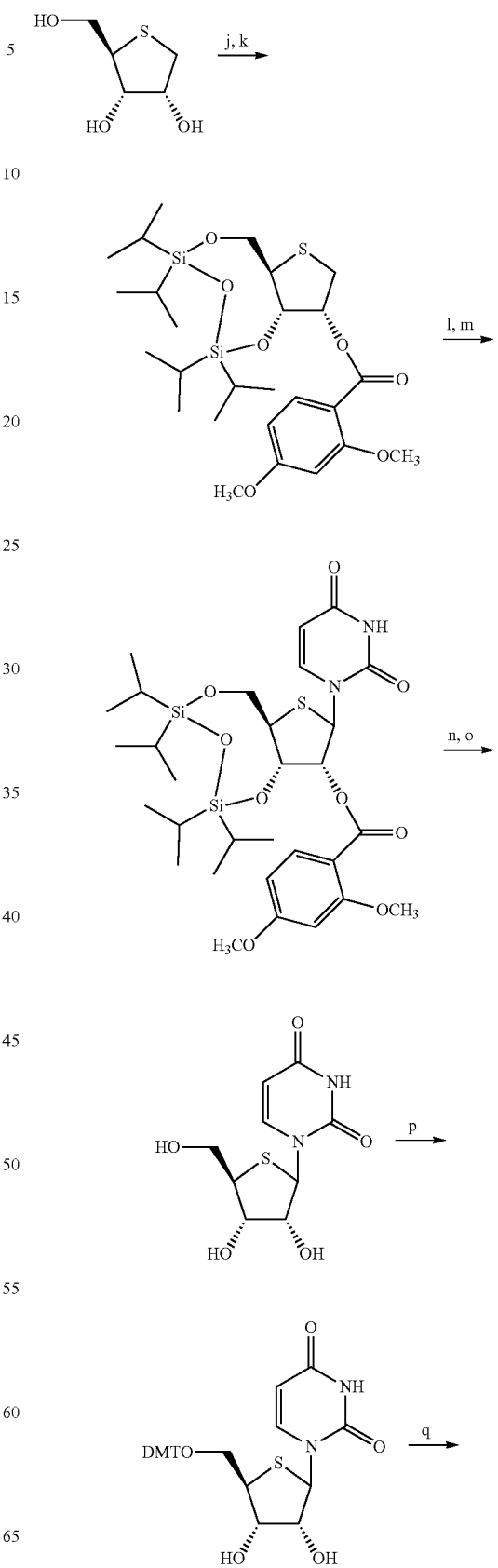

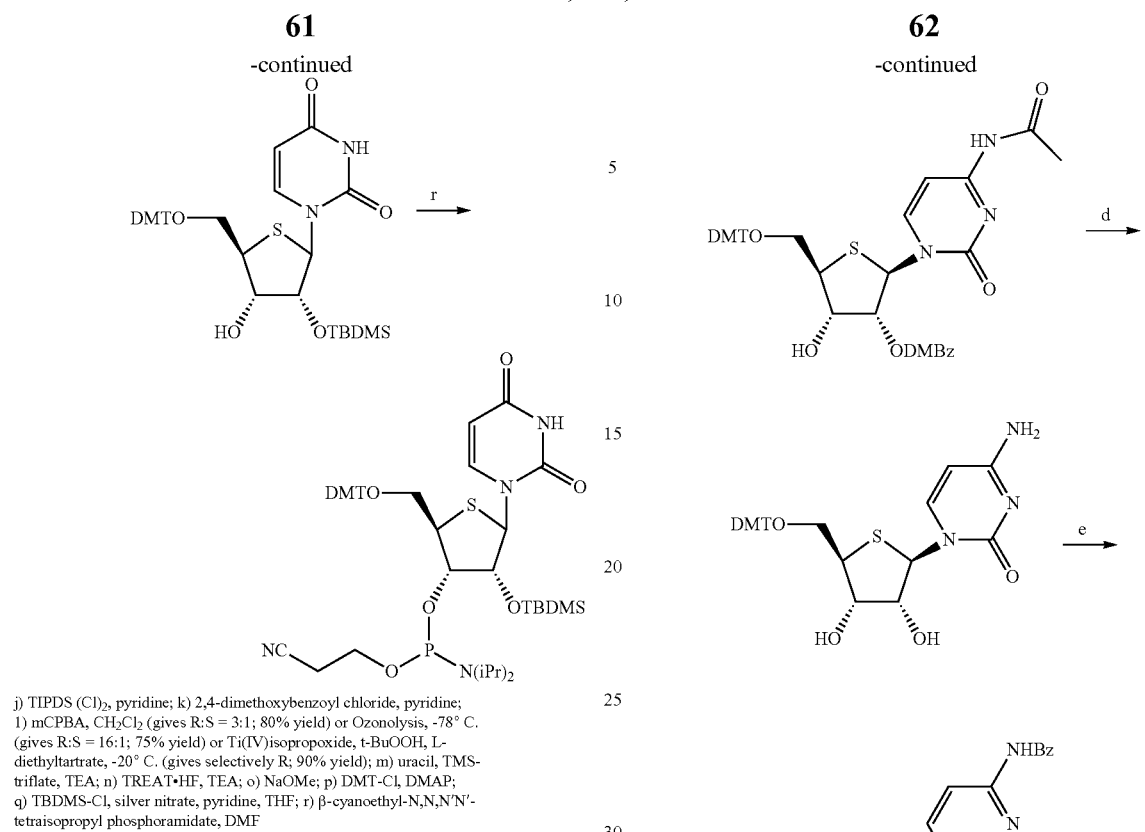

j) TIPDS (Cl)$_2$, pyridine; k) 2,4-dimethoxybenzoyl chloride, pyridine;
l) mCPBA, CH$_2$Cl$_2$ (gives R:S = 3:1; 80% yield) or Ozonolysis, -78° C. (gives R:S = 16:1; 75% yield) or Ti(IV)isopropoxide, t-BuOOH, L-diethyltartrate, -20° C. (gives selectively R; 90% yield); m) uracil, TMS-triflate, TEA; n) TREAT•HF, TEA; o) NaOMe; p) DMT-Cl, DMAP; q) TBDMS-Cl, silver nitrate, pyridine, THF; r) β-cyanoethyl-N,N,N'N'-tetraisopropyl phosphoramidate, DMF Scheme 4: Synthesis of 4'Thio-C Phosphoramidite

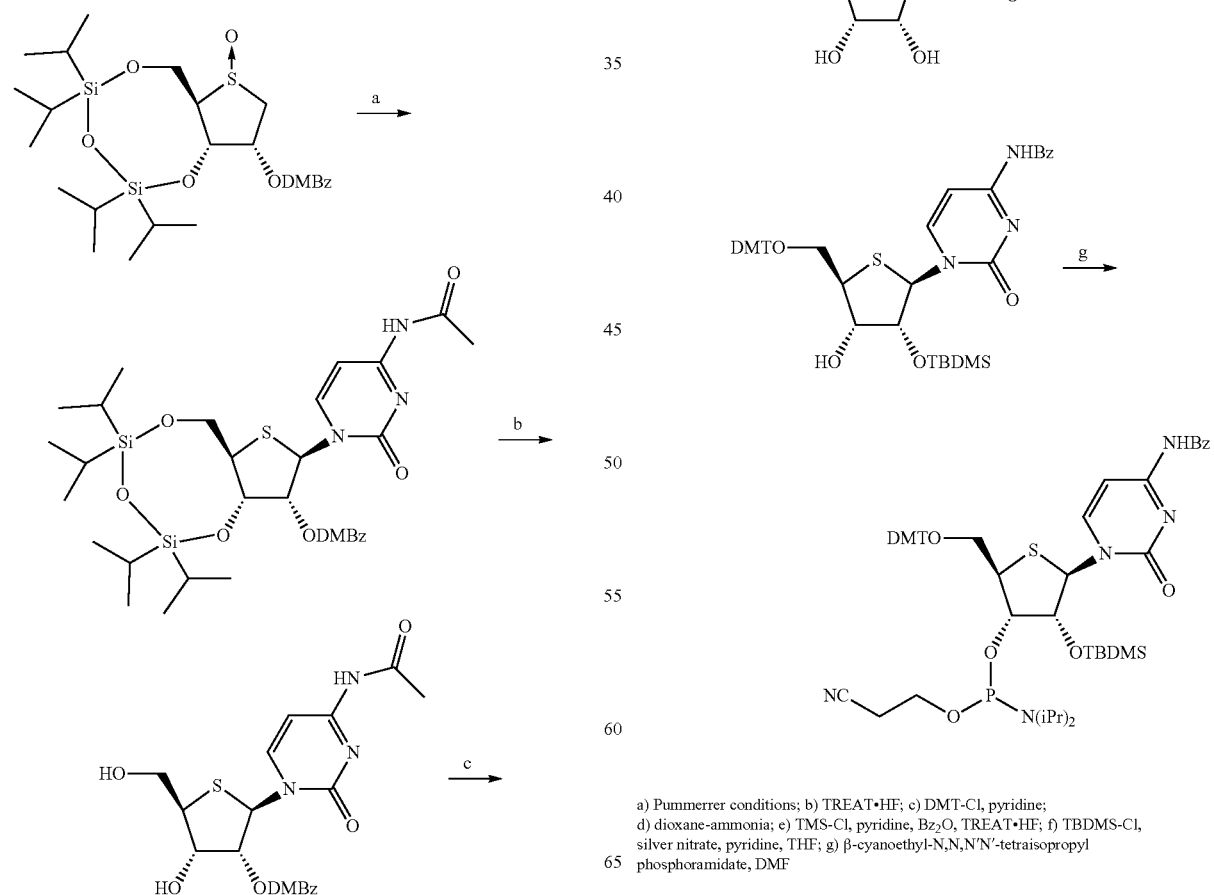

a) Pummerrer conditions; b) TREAT•HF; c) DMT-Cl, pyridine;
d) dioxane-ammonia; e) TMS-Cl, pyridine, Bz$_2$O, TREAT•HF; f) TBDMS-Cl, silver nitrate, pyridine, THF; g) β-cyanoethyl-N,N,N'N'-tetraisopropyl phosphoramidate, DMF Scheme 5: Synthesis of 4'Thio-G Phosphoramidite
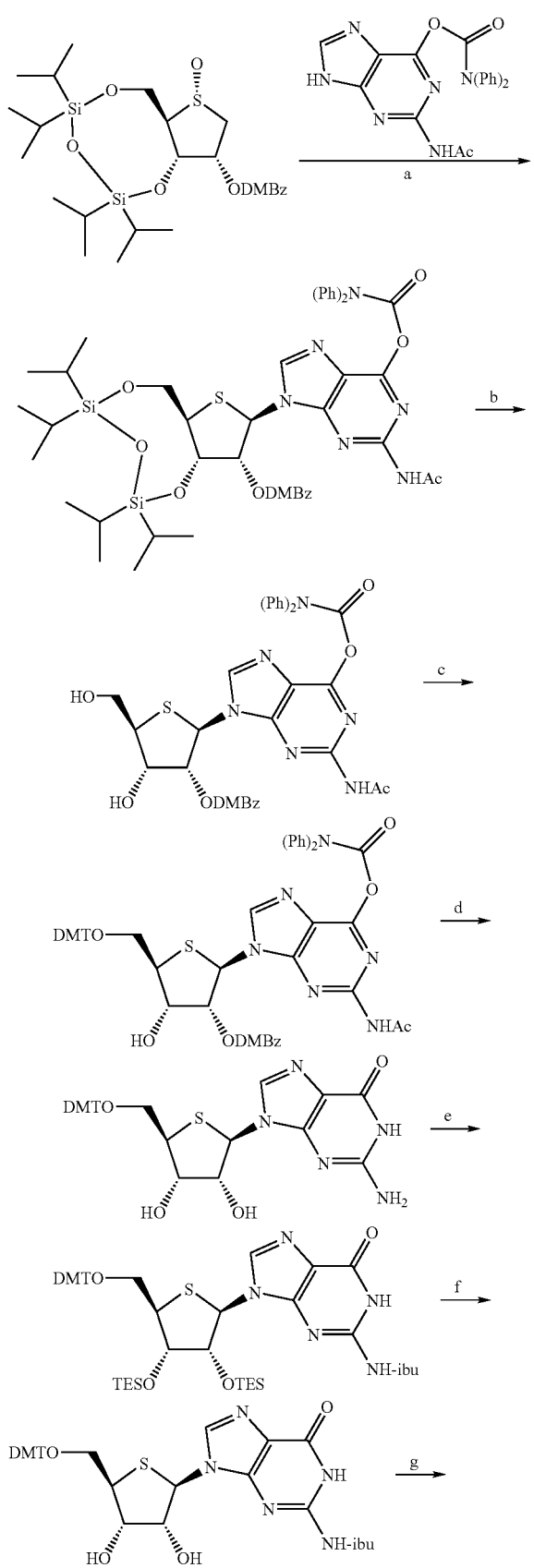
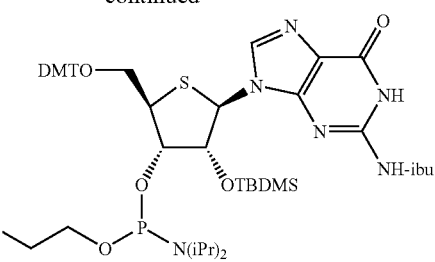
a) Pummerrer conditions; b) TREAT•HF; c) DMT-Cl, pyridine; d) dioxane-ammonia; e) TES-Cl, pyridine, isobutyryl chloride, TREAT•HF; f) TBDMS-Cl, silver nitrate, pyridine, THF; g) β-cyanoethyl-N,N,N'N'-tetraisopropyl phosphoramidate, DMF
Scheme 6: Synthesis of 2'-OMe-4'-Thio-U
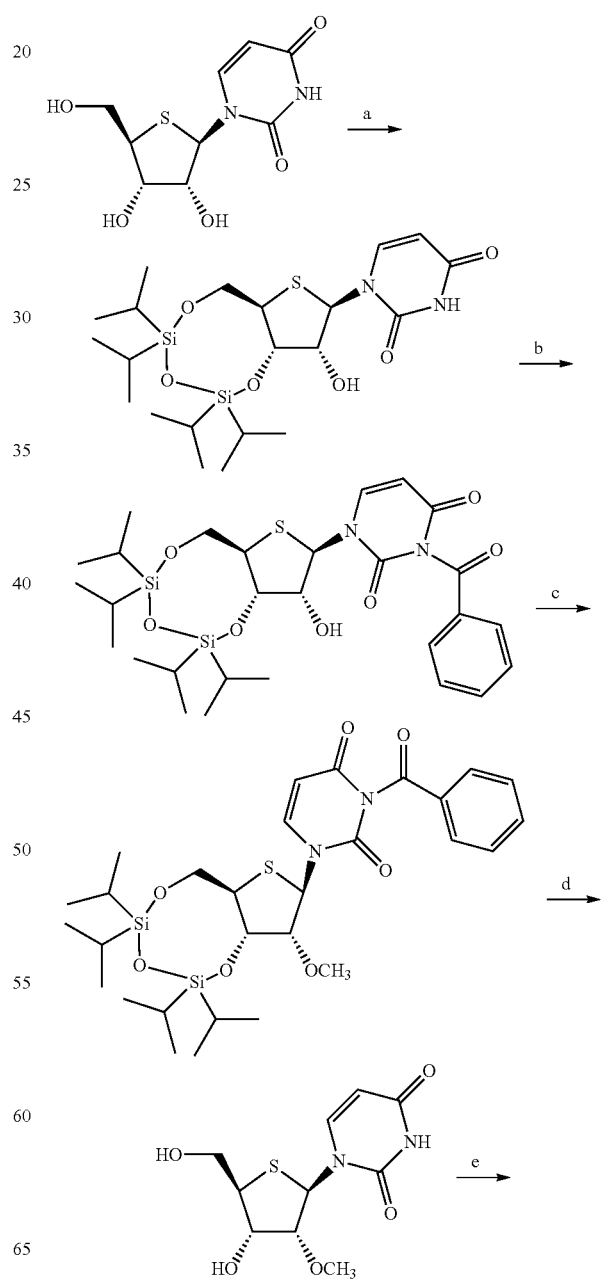

65

-continued

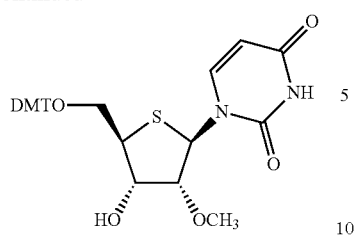

a) TIPDSCl$_2$, pyridine; b) tetrabutylammonium bromide, CH$_2$Cl$_2$, NaCO$_3$ soln., dichloroethane, benzoyl chloride; c) silver oxide, iodomethane; d) TREAT·HF, TEA, methanolic ammonia; e) DMT-Cl, pyridine Scheme 7: Synthesis of 2'-OMe-4'-Thio-C

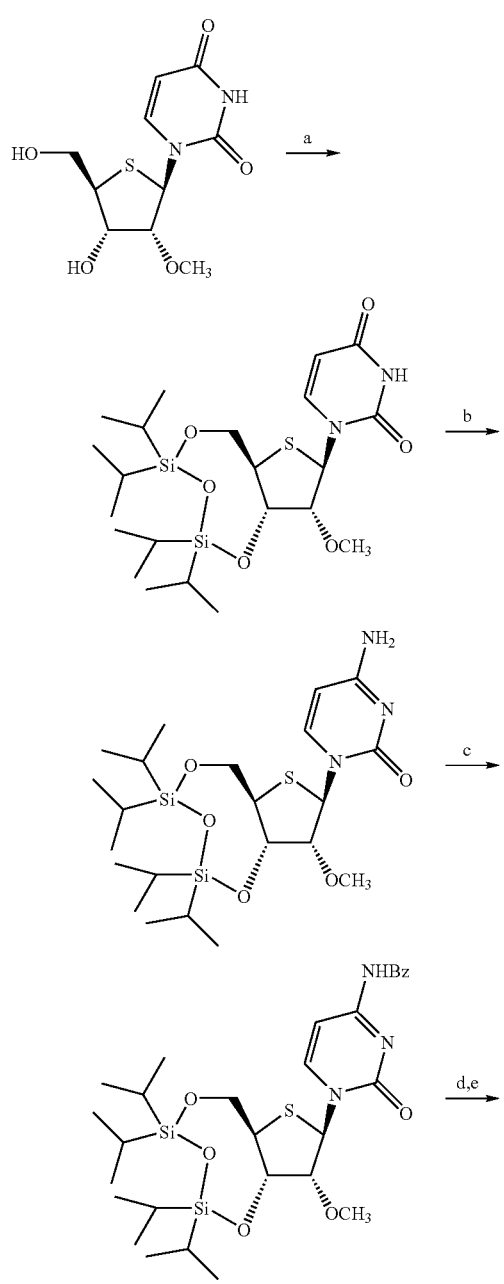

66

-continued

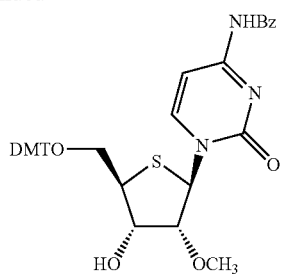

a) TIPDSCl$_2$, pyridine; b) POCl$_3$, TEA, CH$_3$CN, then NH$_4$OH, Dioxane c) Benzoyl tetrazole CH$_3$CN, 60° C. d) TREAT·HF, TEA; e) DMT-Cl, pyridine Scheme 8: Synthesis of 2'-fluoro-4'-thio-uracil

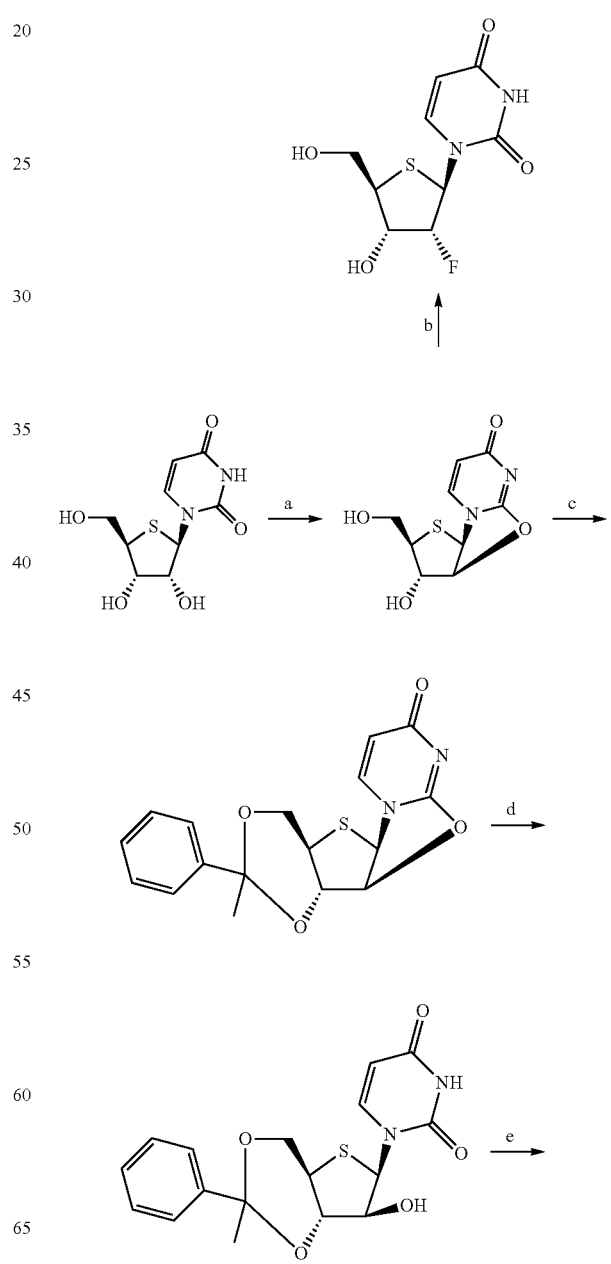

-continued

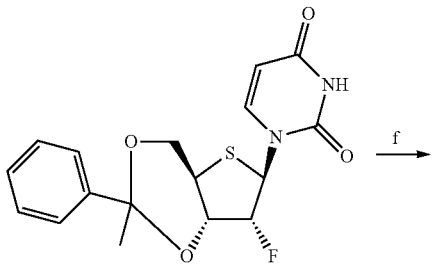

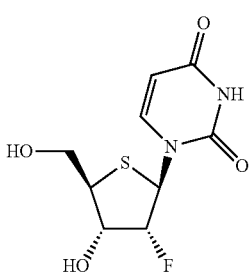

a) diphenyl carbonate, sodium bicarbonate, DMA, heat; b) Tetrabutylammonium fluoride, THF, heat; c) benzylidene dimethyl acetal, camphor sulfonic acid, DMF; d) 1N NaOH, water/Dioxane, reflux; e) nonafluorobutanesulfonyl fluoride, DBU, toluene, heat; e) TCA, methanol.

EXAMPLES

The compounds and processes of the present invention will be described further in detail with respect to specific preferred embodiments by way of examples, it being understood that these are intended to be illustrative only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

1-O-methyl-D-ribose (2)

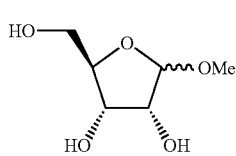

D-ribose (500 g, 3.33 moles) was dissolved in 1.5 L of dry methanol containing 0.5% hydrochloric acid and stirred in a flask equipped with a calcium carbonate drying tube for 48 hrs. The reaction mixture was neutralized with Dowex (OH form) resin to pH 7. The reaction mixture was filtered and concentrated under reduced pressure followed by drying in vacuo overnight to give compound 2 (550 g) in 98% yield.

Example 2

2,3,5-tri-O-benzyl-1-O-methyl-D-ribose (3)

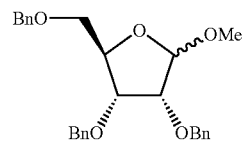

Compound 2 (150 g, 0.914 mole) was dissolved in dry N,N-dimethylformamide (DMF, 1.5 L), under nitrogen, in a three necked flask equipped with a mechanical stirrer and an addition funnel. The solution was cooled to 0° C. in an ice bath. NaH (220 g, 60% dispersion in mineral oil, 5.48 mole, 6 eq.) was added in small portions taking care to control the reaction and avoid overheating. When all the NaH had been added, addition of benzyl bromide (650 mL, 5.48 mole, 6 eq.) was initiated drop-wise via the addition funnel. When all the benzyl bromide had been added the reaction was allowed to come to room temperature and stirred for 5 hrs. The reaction was then heated to 60° C. and stirred at this temperature overnight. The reaction was quenched with methanol, concentrated in vacuo, and partitioned between ether and water. The ether layer was washed once with 10% citric acid solution, once with saturated sodium bicarbonate solution and once with brine. The ether layer was dried over anhydrous sodium sulfate, and concentrated to a pale, yellow syrup. This syrup was dissolved in 5% ethyl acetate in hexane and applied to a silica gel plug in a 2 L sintered glass funnel. 5% ethyl acetate in hexane was used to elute the desired product in 2 L fractions. The target fractions were concentrated under reduced pressure to give compound 3 (300 g) in 75% yield.

Example 3

2,3,5-Tri-O-benzyl-D-ribitol (4)

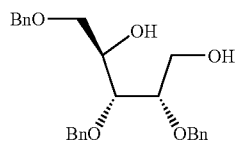

Compound 3 (300 g, 0.688 mole) was treated as per procedures described in Naka et al. in J. Am. Chem. Soc., Vol. 122, No. 30, 2000 to obtain compound 4 (200 g) in 70% yield.

Example 4

2,3,5-Tri-O-benzyl-1-O-tert-butyldiphenylsilyl-D-ribitol (5)

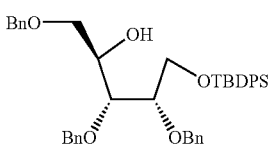

To an ice-cold solution of Compound 4 (200 g, 0.47 mole) in dry pyridine (1 L), under nitrogen, was added tert-butyldiphenylsilyl chloride (130 mL, 0.50 mole, 1.05 eq.) slowly with vigorous stirring. The reaction mixture was allowed to come to room temperature and stirred overnight. The reaction was then quenched with methanol, and solvent was removed under reduced pressure. The residue was taken up in ethyl acetate and washed successively with, water (twice), 10% citric acid solution, sat. sodium bicarbonate solution, and brine. The ethyl acetate layer was separated, dried over anhydrous sodium sulfate, and concentrated under reduced pressure to give compound 5 (400 g) in 98% yield. The material was of sufficient purity to be used without further purification.

Example 5

2,3,5-Tri-O-benzyl-1-O-tert-butyldiphenylsilyl-4-O-p-nitrobenzoyl-L-lyxitol (6)

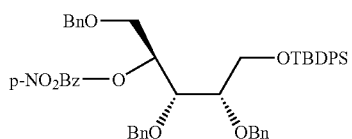

6

Compound 5 (150 g, 232.5 mmole) was treated as per procedures described in Naka et al. in J. Am. Chem. Soc., Vol. 122, No. 30, 2000 to obtain Compound 6 (130 g) in 70% yield.

Example 6

2,3,5-Tri-O-benzyl-L-lyxitol (7)

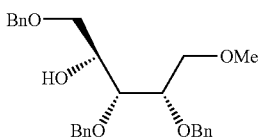

7

Compound 6 (110 g, 138.54 mmole) was dissolved in methanol (500 mL) and sodium methoxide (11 g, 204.0 mmole, 1.5 eq.) was added and the solution was stirred at room temperature for 2 hours. The reaction mixture was concentrated under reduced pressure, and the residue was partitioned between ether and water. The separated organic layer was washed with brine, dried over anhydrous sodium sulfate and concentrated under reduced pressure. The residue was dried in vacuo for 3 hrs and dissolved in dry THF under nitrogen. Triethylamine (TEA) (100 mL, 0.752 mole, 5 eq.) was added followed by triethylamine trihydrofluoride (TREAT.HF) (220 mL, 1.38 mole, 10 eq.) and the mixture was stirred overnight at room temperature. The solvent was removed under reduced pressure and the residue partitioned between ether and water. The ether layer was washed with brine and dried over anhydrous sodium sulfate. The solvent was removed under reduced pressure and the residue purified by flash chromatography (40% ethyl acetate in hexane) to give 51 g of compound 7 in 90% yield (reported literature yield 81%).

Example 7

1,4-anhydro-2,3,5-tri-O-benzyl-4-thio-D-ribitol (8)

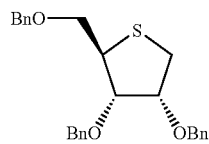

8

Compound 7 (51 g, 121.0 mmole) was treated as per procedures described in Naka et al. in J. Am. Chem. Soc., Vol. 122, No. 30, 2000 to obtain 47 g of 8 in 85% yield.

Example 8

1,4-anhydro-4-thio-D-ribitol (9)

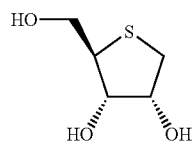

9

Compound 8 (47 g, 112 mmole) was treated as per procedures described in Naka et al. in J. Am. Chem. Soc., Vol. 122, No. 30, 2000 to obtain Compound 9 (13 g) in 80% yield.

Example 9

1,4-anhydro-3,5-O-(1,1,3,3-tetraisopropyldisiloxane-1,3-diyl)-4-thio-D-ribitol (10)

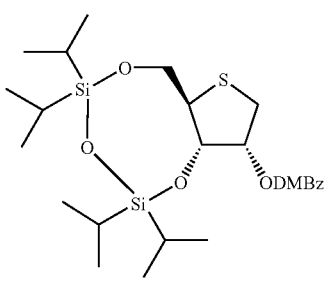

10

Compound 9 (15 g, 100.0 mmole) was treated as per procedures described in Naka et al. in J. Am. Chem. Soc., Vol. 122, No. 30, 2000 to obtain Compound 10 (24 g) in 80% yield.

Example 10

1,4-anhydro-2-O-(2,4-dimethoxybenzoyl)-3,5-O-(1,1,3,3-tetraisopropyldisiloxane-1,3-diyl)-4-thio-D-ribitol (11)

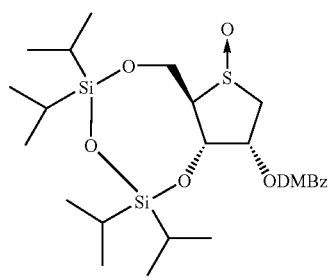

11

Compound 10 (24 g, 61 mmole) was treated as per procedures described in Naka et al. in J. Am. Chem. Soc., Vol. 122, No. 30, 2000 to obtain Compound 11 (30 g) in 90% yield.

Example 11

1,4-anhydro-2-O-(2,4-dimethoxybenzoyl)-3,5-O-(1,1,3,3-tetraisopropyl disiloxane-1,3-diyl)-4-sulfinyl-D-ribitol (11a)

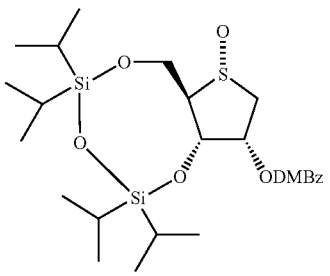

11a

The title compound was prepared by a new route (followed similar precedence, to synthesize asymmetric 1,3-Dithiolane Nucleoside analogs, Romualo Caputo et. al. Eur. J. Org. Chem. 2003, 346-350). To a solution of Ti(IV) isopropoxide (0.3 mL, 1.10 mmole, 0.45 eq.) in dry dichloromethane (5 mL), under nitrogen was added diethyl-L-tartrate (0.6 mL, 1.15 mmole, 1.5 eq) with vigorous stirring. The stirring was continued for 20 min at room temperature until a clear straw yellow colored solution was obtained. This solution was cooled to −15° C. to −20° C. and tert-butyl hydroperoxide was added (0.4 mL of 6 M solution in decane, 2.4 mmole). The solution was stirred at the same temperature for 5 minutes and a solution of Compound 10 (1.3 g, 2.3 mmole) in dry dichloromethane (5 mL) was added. The reaction mixture was stirred at the same temperature for 24 hrs when TLC indicated that all starting material had been consumed. The reaction was quenched by the addition of water and allowed to come to room temperature. The reaction mixture was transferred to a separating funnel and partitioned between brine and dichloromethane. The brine layer was extracted several times with dichloromethane and the combined dichloromethane extracts were dried over anhydrous sodium sulfate. The cloudy solution was clarified by filtration through a celite pad and concentrated to syrup under reduced pressure. The residue was purified by flash chromatography using 5 to 10% ethyl acetate in dichloromethane as eluant to obtain Compound 11 (1.2 g) in 90% yield. $^1$H NMR indicated that the product contained only the desired (R) isomer that corresponded to the literature values. The product was contaminated with residual L-diethyl-tartrate but since this impurity does not interfere with the subsequent steps the material was used as such without further purification.

Example 12

1-[2-O-(2,4,-dimethoxybenzoyl)-3,5-O-1,1,3,3-tetraisopropyldisiloxane-1,3-diyl)-4-thio-β-D-ribofuranosyl]uracil (12)

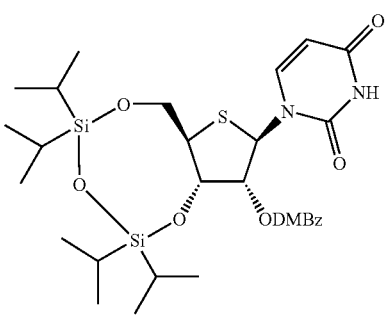

12

Compound 11 (1.2 g, 2.1 mmole) was treated as per procedures described in Naka et al. in J. Am. Chem. Soc., Vol. 122, No. 30, 2000 to obtain Compound 12 (1.3 g) in 90% yield.

Example 13

1-(4-thio-β-D-ribofuranosyl)uracil (13)

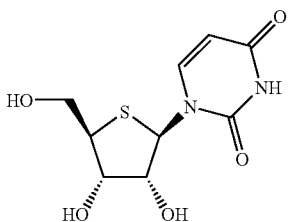

13

Compound 12 (1.2 g, 1.90 mmole) was dissolved in dry THF under nitrogen. TEA (1.3 mL, 9.5 mmole, 5 eq.) and TREAT.HF (2.8 mL, 20 mmole, 10 eq.) were added and the mixture stirred at room temperature for 4 to 5 h. The solvent was removed under reduced pressure and the residue was co-evaporated three times with toluene. Methanolic ammonia (20 mL) was added and the reaction mixture was stirred at room temperature overnight. The solvent was removed under reduced pressure and the residue was purified by flash chromatography (10% methanol in dichloromethane) to give Compound 13 (420 mg) in 90% yield.

Compound 13 was also synthesized using literature procedure (Naka et al. in J. Am. Chem. Soc., Vol. 122, No. 30, 2000) with few modifications that resulted in significant increase in yields.

Example 14

1-[5-(4,4'-dimethoxytrityl)-4-thio-β-D-ribofuranosyl]uracil (14)

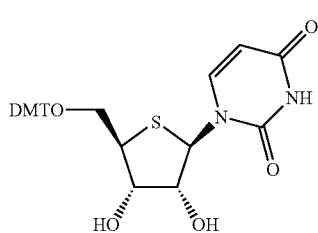

14

Compound 13 (2 g, 7.754 mmol) was dissolved in dry pyridine (20 mL), 4,4'-dimethoxytrityl chloride (2.9 g, 8.53 mmol) was added and the mixture stirred at room temperature overnight. The reaction was quenched with methanol and taken up in ethyl acetate (200 mL). The ethyl acetate solution was washed twice with saturated sodium bicarbonate solution, once with water, once with brine, and dried over anhydrous sodium sulfate. The solvents were removed under reduced pressure and the residue purified by flash chromatography (7% methanol in dichloromethane). The desired fractions were pooled and concentrated to give Compound 14 (3.0 g) in 80% yield. The structure of Compound 14 was confirmed by $^1$H NMR & ESMS.

Example 15

1-[5-(4,4'-dimethoxytrityl)-2-(t-butyldimethylsilyl)-4-thio-β-D-ribofuranosyl]uracil (15a-c)

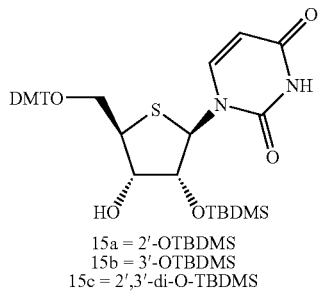

15a = 2'-OTBDMS
15b = 3'-OTBDMS
15c = 2',3'-di-O-TBDMS

Compound 14 (4.3 g, 7.66 mmol), silver nitrate (3.1 g, 18.5 mmol), anhydrous pyridine (4.5 mL, 56.0 mmol) and TBDMS-Cl (2.8 g, 18.57 mmol) were dissolved in dry THF (75 mL) and stirred at room temperature overnight. The precipitated silver chloride was removed by filtration through a pad of celite and washed with several portions of THF. The combined washings were concentrated to furnish a foam, which was purified by flash chromatography (40% ethyl acetate in hexane) to give Compound 15a (3.2 g, 63%), 15b (1.2 g, 23%) & 15c (0.43 g, 8.3%). The structures were confirmed by 1H NMR.

Example 16

1-(3-O-(2-Cyanoethoxy(diisopropylamino)phosphino)-5-O-(4,4'-dimethoxytrityl)-2-O-tert.Butyldimethylsilyl)-4-thio-β-D-ribofuranosyl)uracil (16)

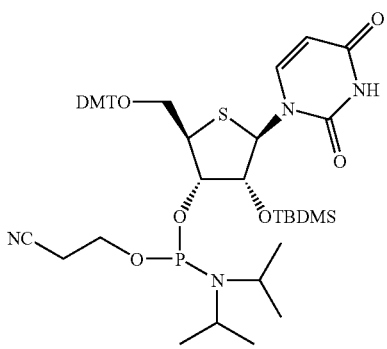

16

To a solution of Compound 15a (2.5 g, 3.7 mmol) in anhydrous DMF (13 mL) was added dried 1H-tetrazole (0.2 g, 2.8 mmol), N-methylimidazole (0.077 g, 0.9 mmol) and 2-cyanoethoxy-N,N,N',N'-tetraisopropylphosphoramidite (1.6 g, 5.30 mmol). The reaction mixture was stirred at room temperature for 8 h. It was taken up in EtOAc (200 mL) and washed with brine (5×50 mL). The organic layer was concentrated and the resulting oil purified by column chromatography using 10% acetone in dichloromethane as the eluent. Appropriate fractions were collected and concentrated to a foam, which was dried for two days under high vacuum to furnish pure amidite, yield, 2.96 g, 91.6%. 1H and 31P NMR indicated the correct structure of Compound 16.

Example 17

N$^4$-Acetyl-1-[2-O-(2,4,-dimethoxybenzoyl)-3,5-O-(1,1,3,3-tetraisopropyldisiloxane-1,3-diyl)-4-thio-β-D-ribofuranosyl]cytosine (17)

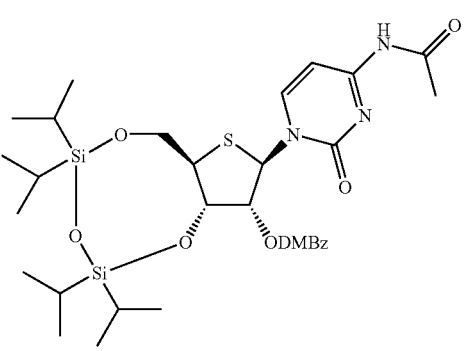

17

Compound 11 (1.2 g, 2.1 mmole) is treated as per procedures described in Naka et al. in J. Am. Chem. Soc., Vol. 122, No. 30, 2000 to obtain Compound 17.

Example 18

1-(4-thio-β-D-ribofuranosyl)cytosine (18)

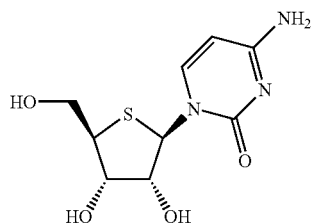

18

Compound 17 (1 eq.) is dissolved in dry THF under nitrogen. TEA (1.3 mL, 9.5 mmole, 5 eq.) and TREAT.HF (2.8 mL, 20 mmole, 10 eq.) are added and the mixture stirred at room temperature for 4 to 5 h. The solvent is removed under reduced pressure and the residue is co-evaporated three times with toluene. Methanolic ammonia (2 mL) is added and the reaction mixture is stirred at room temperature overnight. The solvent is removed and the residue is purified by flash chromatography (10% methanol in $CH_2Cl_2$ containing 0.1% TEA) to give Compound 18.

Example 19

1-[2,3-di-O-acetyl-5-(4,4'-dimethoxytrityl)-4-thio-β-D-ribofuranosyl]uracil (19)

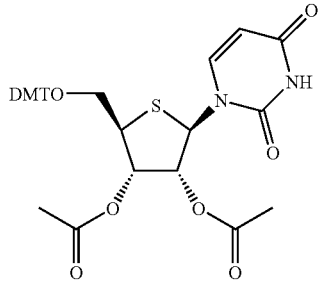

19

Compound 14 (3.0 g, 5.36 mmol) was dissolved in dry pyridine (25 mL). Acetic anhydride (5 mL, 53.6 mmol) was added and the mixture was stirred at room temperature for 16 hrs. The reaction was quenched with methanol and taken up in ethyl acetate (100 mL). The ethyl acetate solution was washed twice with saturated sodium bicarbonate solution, once with water, once with brine, and dried over anhydrous sodium sulfate. The solvents were removed under reduced pressure and the residue purified by flash chromatography (2% methanol in dichloromethane). The desired fractions were pooled and concentrated to give Compound 19 (2.5 g) in 75% yield.

Example 20

1-[5-(4,4'-dimethoxytrityl)-4-thio-β-D-ribofuranosyl]cytosine (20)

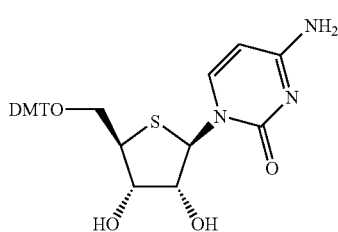

20

1,2,4-triazole (3.73 g, 54 mmol) was suspended in dry acetonitrile (42 mL) and cooled to 0° C. in an ice bath. $POCl_3$ (1.44 mL, 15.4 mmol) was added drop wise with stirring. TEA (10.73 mL, 77 mmol) was added slowly with vigorous stirring and the mixture was stirred at this temperature for an additional 30 min. A solution of Compound 19 (2.43 g, 3.85 mmol) in dry acetonitrile (14 mL) was added and the mixture stirred at 0° C. for 2 h and at room temperature for 1 hr. The solvents were removed under reduced pressure and the residue taken up in ethyl acetate. The ethyl acetate solution was washed twice with saturated sodium bicarbonate solution, once with brine and dried over anhydrous sodium sulfate. The solvents were removed under reduced pressure and the residue was taken up in dioxane (40 mL) and 30% ammonium hydroxide solution (20 mL) was added. The mixture was stirred in a sealed flask overnight at room temperature. The solvents were removed under reduced pressure and the residue purified by flash chromatography (10% methanol in dichloromethane) to give Compound 20, (2.0 g) in 75% yield.

Example 21

N-benzoyl-1-[5-(4,4'-dimethoxytrityl)-4-thio-β-D-ribofuranosyl]cytosine (21)

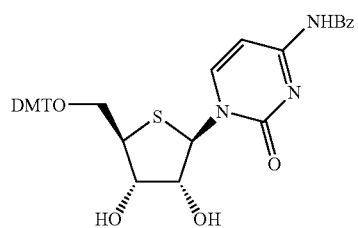

21

Compound 20 (2.0 g, 3.6 mmole) was dissolved in dry DMF (20 mL) and benzoic anhydride (1.63 g, 7.2 mmol) was added. The mixture was stirred at room temperature overnight. The reaction was quenched by pouring into ice cold saturated sodium bicarbonate solution and stirred for 30 min. The mixture was transferred to a separating funnel and extracted three times with dichloromethane. The organic layer was dried over anhydrous sodium sulfate and concentrated under reduced pressure. The residue was purified by flash chromatography (5% methanol in dichloromethane) to give Compound 21 (2.0 g) in 85% yield.

Example 22

N-benzoyl-1-[5-(4,4'-dimethoxytrityl)-2-(t-butyldimethylsilyl)-4-thio-β-D-ribofuranosyl]cytosine (23)

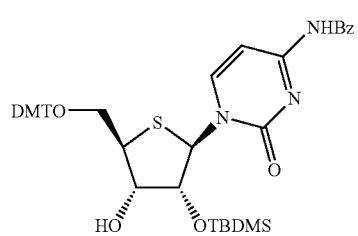

23

Compound 21 (200 mg, 0.3 mmol), silver nitrate (100 mg, 0.6 mmol), and TBDMS-Cl (70 mg, 0.45 mmol) were dissolved in dry THF and stirred at room temperature overnight. The reaction was diluted with ethyl acetate and washed with saturated sodium bicarbonate solution, water and brine. The organic layer was dried over anhydrous sodium sulfate and concentrated under reduced pressure. The residue was purified by flash chromatography (30% ethyl acetate in hexanes) to give Compound 23 (100 mg) in 45% yield. The 3-protected analog (N-benzoyl-1-[5-(4,4'-dimethoxytrityl)-3-(t-butyldimethylsilyl)-4-thio-β-D-ribofuranosyl]cytosine) was also isolated as a minor product.

Example 23

N⁴-Bz-1-(3-O-2-Cyanoethoxy(diisopropylamino)
phosphino)-5-O-(4,4'-dimethoxy-trityl)-2-O-tert.
Butyldimethylsilyl)-4-thio-β-D-ribofuranosyl)cy-
tosine (24)

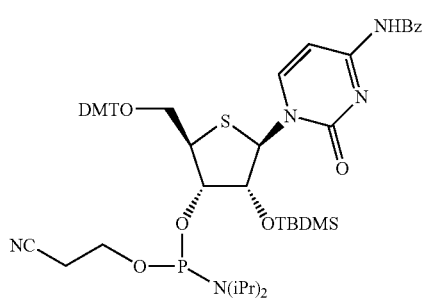

Compound 23 (0.49 g, 0.628 mmol) in anhydrous DMF (3 mL) was added dried 1H-tetrazole (0.04 g, 0.56 mmol), N-methylimidazole (0.013 g) and 2-cyanoethoxy-N,N,N',N'-tetraisopropylphosphoramidite (0.286 g, 0.948 mmol). The reaction mixture was stirred at room temperature for 8 h and then taken up in EtOAc (20 mL) and washed with brine (5×10 mL). The organic layer was dried over anhydrous sodium sulfate and concentrated. The resulting oil was purified by column chromatography using 10% acetone in dichloromethane as the eluent. Appropriate fractions were collected and concentrated to a foam, which was dried for two days under high vacuum to furnish pure amidite, yield, 0.552 mg, 89%. 1H and 31P NMR indicated the correct structure of compound 24.

Example 24

Synthesis of 4'-thioadenosine

The synthesis of this compound is carried out according to the literature procedure by Naka et al. in J. Am. Chem. Soc., Vol. 122, No. 30, 2000.

Example 25

N6-benzoyl-5'-dimethoxytrityl-2'-O-tert-butyldim-
ethylsilyl-3'-O-(cyanoethoxy-N,Ndiisopropyl-pho-
phoramidite)-4'-thio-adenosine The title compound is prepared from 4'-thioadenosine, using the standard procedures (Claudine Leydier et.al., Antisense Research and Development 5, 1995, 167 and the references therein & Claudine Leydier et.al. Nucleosides & Nucleotides, 13, 1994, 2035 and the references therein.)

Example 26

Synthesis of 4'-Thioguanosine (33)

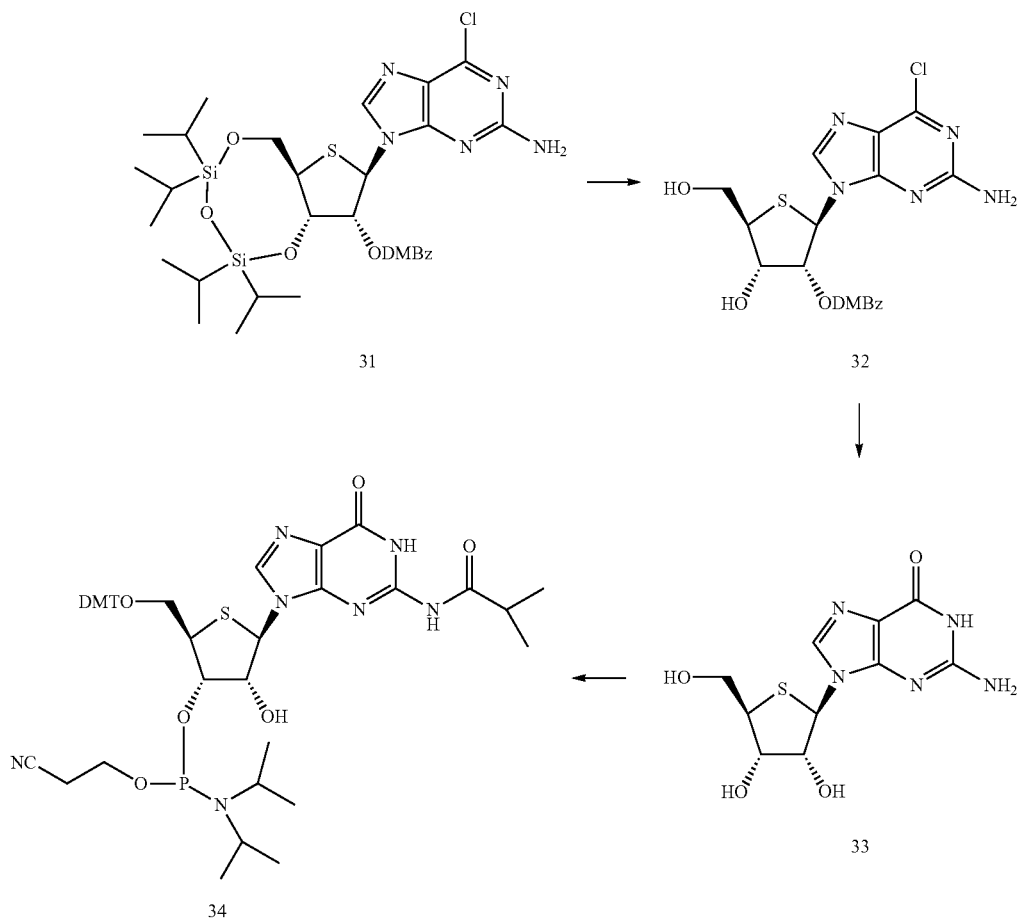

The title compound is prepared according to literature procedures starting with Compound 11 (Naka et al. in J. Am. Chem. Soc., Vol. 122, No. 30, 2000.)

Example 27

N²-isobutyryl-5'-dimethoxytrityl-2'-O-tert-butyldimethylsilyl-3'-O-(cyanoethoxy-N,N-diisopropyl-phophoramidite)-4'-thio-guanosine (34)

This compound is prepared from 4'-thioguanosine using one of a number of literature procedures (Masad J. Damha & Kelvin K. Ogilvie in ""Methods in Molecular Biology, Vol. 20: page 81 (and the references therein) Protocols for Oligonucleotide and Analogs; Edited by: S. Agarwal Humana Press Inc, Totowa, N.J. Oligonucleotide synthesis a practical approach. (1984) M. J. Gait editor IRL Press, Oxford; Scaringe, Stephen A.; Francklyn, Christopher; Usman, Nassim, Chemical synthesis of biologically active oligoribonucleotides using b-cyanoethyl protected ribonucleoside phosphoramidites, Nucleic Acids Research (1990), 18(18), 5433-41.)

Example 28

Synthesis of 2'-OMe-4'-thio-U Phosphoramidite

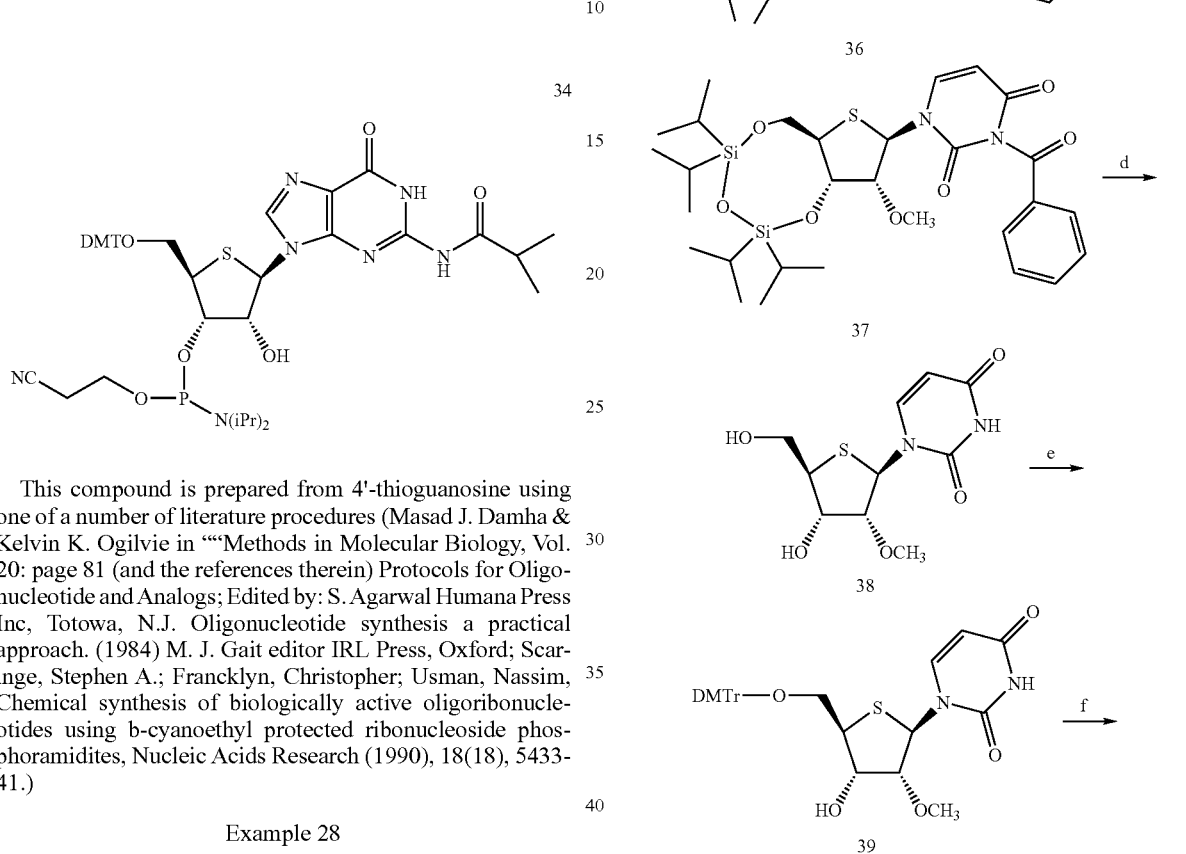

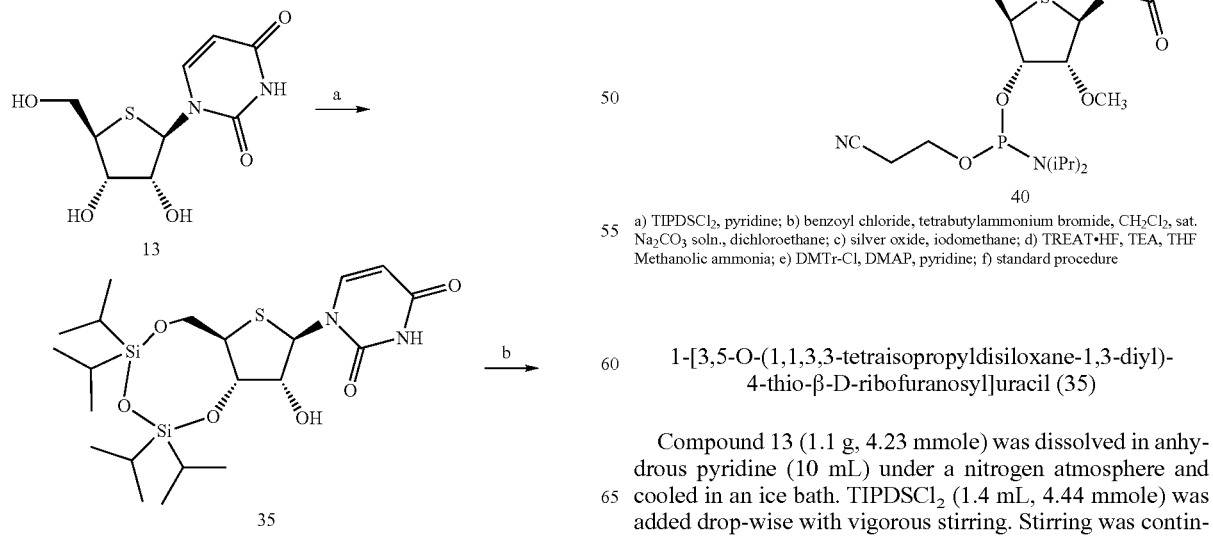

a) TIPDSCl₂, pyridine; b) benzoyl chloride, tetrabutylammonium bromide, CH₂Cl₂, sat. Na₂CO₃ soln., dichloroethane; c) silver oxide, iodomethane; d) TREAT•HF, TEA, THF Methanolic ammonia; e) DMTr-Cl, DMAP, pyridine; f) standard procedure 1-[3,5-O-(1,1,3,3-tetraisopropyldisiloxane-1,3-diyl)-4-thio-β-D-ribofuranosyl]uracil (35)

Compound 13 (1.1 g, 4.23 mmole) was dissolved in anhydrous pyridine (10 mL) under a nitrogen atmosphere and cooled in an ice bath. TIPDSCl₂ (1.4 mL, 4.44 mmole) was added drop-wise with vigorous stirring. Stirring was continued at the same temperature for an additional 2 to 4 h. When all of 13 had been consumed the reaction was quenched by pouring onto ice. The mixture was separated between ethyl acetate and water and the ethyl acetate layer was washed thrice with cold sat. sodium bicarbonate solution and once with brine. The ethyl acetate layer was dried over anhydrous sodium sulfate and concentrated under reduced pressure. The crude material was purified by flash chromatography (5% methanol in dichloromethane) to give Compound 35 (1.7 g, 80% yield).

3-N-benzoyl-1-[3,5-O-(1,1,3,3-tetraisopropyldisiloxane-1,3-diyl)-4-thio-β-D-ribofuranosyl]uracil (36)

A mixture of Compound 35 (250 mg, 0.5 mmole), $Na_2CO_3$ (424 mg, 4 mmole) and tetrabutylammonium bromide (7 mg, 0.02 mmole) were dissolved in a biphasic mixture of $CH_2Cl_2$—$H_2O$. Benzoyl chloride (87 μL, 0.75 mmole) was added and the mixture was stirred at room temperature until all of Compound 35 was consumed. The mixture was transferred to a separating funnel. The organic phase was collected and the aqueous phase extracted twice with $CH_2Cl_2$. The organic extracts were combined, dried over anhydrous sodium sulfate and concentrated under reduced pressure. The residue was taken up in 1,2-dichloroethane and heated at 60° C. for 15 min. The solvent was removed under reduced pressure and the residue purified by flash chromatography (10% acetone in dichloromethane) to obtain Compound 36 (225 mg, 75% yield).

3-N-benzoyl-1-[2-O-methyl-3,5-O-(1,1,3,3-tetraisopropyldisiloxane-1,3-diyl)-4-thio-β-D-ribofuranosyl]uracil (37)

Compound 36 (100 mg, 0.165 mmole) was dissolved in dry DMF under an inert atmosphere. Silver oxide (383 mg, 1.65 mmole) and iodomethane (200 μL, 3.3 mmole) were added and the mixture stirred at room temperature overnight. Methanol was added to quench the reaction and the reaction mixture was partitioned between ethyl acetate and water. The ethyl acetate layer was washed twice with water, once with brine, dried over anhydrous sodium sulfate and concentrated under reduced pressure. The residue was purified by flash chromatography (gradient ethyl acetate in hexanes) to give Compound 37 (67 mg, 65% yield).

1-(2-O-methyl-4-thio-AD-ribofuranosyl)uracil (38)

Compound 37 (260 mg, 0.42 mmole) was dissolved in dry THF (10 mL). TREAT.HF (1.5 mL) and TEA (0.75 mL) were added and the mixture stirred for 4 hrs. The solvent was removed under reduced pressure followed by two co-evaporations with dry toluene. The residue was taken up in methanolic ammonia (5 mL) and stirred in a sealed tube overnight. The solvents were removed under reduced pressure and the residue purified by flash chromatography (10% methanol in dichloromethane) to give Compound 38 (100 mg, 85% yield). $^1H$ NMR (DMSO-$d_6$) δ 11.35 (br s, 1H), 8.0 (d, 1H), 5.97 (d, 1H), 5.64 (d, 1H), 5.2 (br s, 2H), 4.2 (d, 1H), 3.9 (d, 1H), 3.58 (dd, 2H), 3.26 (s, 3H), 1.18 (m, 1H).

1-(5-(4,4'-Dimethoxy-trityl)-2-O-methyl-4-thio-β-D-ribofuranosyl)uracil (39)

Compound 38 (400 mg, 1.46 mmole) was dissolved in dry pyridine in cold. Dimethoxytrityl chloride (600 mg, 1.752 mmole) was added and the mixture was stirred at room temperature for 24 hrs. Solvents were removed under reduced pressure and the residue was purified by flash chromatography (1:1 ethyl acetate: dichloromethane) to give Compound 39 (600 mg, 75% yield).

2'-O-methyl-4'-thio-U Phosphoramidite (40)

Compound 39 is converted into its corresponding phosphoramidite Compound 107 according to standard procedures. (Oligonucleotide Synthesis: A Practical Approach. Gait, M. J. (Editor) UK. (1984), Publisher: (IRL Press, Oxford, UK).

Example 29

1-[2-O-(2,4,-dimethoxybenzoyl)-4-thio-β-D-ribofuranosyl]uracil (41)

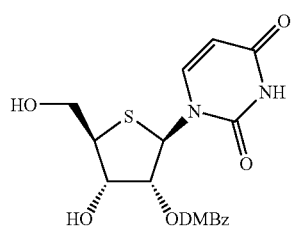

41

Compound 12 (1 eq.) is dissolved in dry THF. TEA (5 eq.) and TREAT.HF (10 eq.) are added and the mixture is stirred at room temperature for 6 h. The solvents are removed under reduced pressure and the residue is co-evaporated with toluene in vacuo. The residue is purified by flash chromatography to give Compound 41.

Example 30

1-[3,5-O-p-methoxybenzylidene-2-O-(2,4,-dimethoxybenzoyl)-4-thio-β-D-ribofuranosyl]uracil (42)

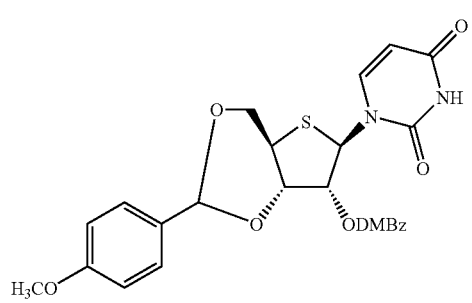

42

Compound 41 (1 eq.) is dissolved in dry DMF. Camphor sulfonic acid (0.2 eq.), and p-methoxybenzaldehyde-dimethylacetal (4 eq.) are added and the reaction is stirred at room temperature until all starting material is consumed. The reaction mixture is diluted with ethyl acetate and washed with saturated sodium bicarbonate solution (2×), water (1×), brine (1×) and dried over anhydrous sodium sulfate. Following concentration under reduced pressure the residue is purified by flash chromatography to give Compound 42.

Example 31

1-[3,5-Op-methoxybenzylidene-4-thio-β-D-ribofuranosyl]uracil (43)

Compound 42 is dissolved in methanolic ammonia and stirred at room temperature for 13 h. The reaction mixture is concentrated under reduced pressure and the residue is purified by flash chromatography to give Compound 43.

Example 32

3',5'-O-p-methoxybenzylidene-4'-thio-$O^2$,2'-anhydrouridine (44)

Compound 43 (1 eq.) is treated with diphenylcarbonate (21.2 eq.) in dry DMF, heated to 90° C. and sodium bicarbonate is added (10 grams per gram of Compound 43). The reaction is held at 110° C. for 2.5 h., cooled and filtered. The residue is washed several times with ethyl acetate and the washings are combined with the initial filtrate. The combined filtrates are washed with water (2×), brine (1×), and dried over anhydrous sodium sulfate. The solvents are removed under reduced pressure and the residue is purified by flash chromatography to give Compound 44.

Example 33

1-[3,5-O-p-methoxybenzylidene-2-fluoro-4-thio-β-D-ribofuranosyl]uracil (45)

Compound 44 (1 eq.) is dissolved in dry THF. TBAF (10 eq.) is added and the reaction mixture is refluxed until starting material is consumed. The solvent is removed under reduced pressure and the residue purified by flash chromatography to give Compound 45.

Alternately Compound 45 is also obtained by heating Compound 44 in dry DMF in presence of 18-crown-6 (5 eq.) and KF (20 eq) at 110° C. followed by above work-up and flash chromatography.

Example 34

1-[2-fluoro-4-thio-β-D-ribofuranosyl]uracil (46)

Compound 45 is dissolved in 80% AcOH and stirred at room temperature for 10 h. The reaction mixture is concentrated under reduced pressure and co-evaporated twice with toluene. The residue is purified by flash chromatography to give Compound 46.

Example 35

1-[3,5-O-p-methoxybenzylidene-4-thio-β-D-arabinofuranosyl]uracil (47)

Compound 44 (0.3 mmol) is dissolved in dioxane (2 mL) and a 2N NaOH soln (2 mL) is added. The reaction mixture is stirred at room temperature till all starting material is consumed. The reaction mixture is neutralized with acetic acid and concentrated to dryness under reduced pressure. The residue is purified by flash chromatography to give Compound 47.

Example 36

1-[3,5-O-p-methoxybenzylidene-2-methanesulfonyl-4-thio-β-D-arabinofuranosyl]uracil (48)

Compound 47 (1 eq.) is dissolved in dry pyridine and cooled to 0° C. Methanesulfonyl chloride (1.5 eq.) is added and the reaction is stirred at room temperature over night. The reaction is quenched by pouring onto ice and the aqueous phase is extracted three times with dichloromethane. The dichloromethane solution is concentrated under reduced pressure and the residue is purified by flash chromatography to give Compound 48.

Example 37

1-[3,5-O-p-methoxybenzylidene-2-fluoro-4-thio-β-D-ribofuranosyl]uracil (45)

Compound 48 (1 eq.) is dissolved in dry DMF. TBAF (10 eq.) is added and the reaction mixture is heated at 100° C. until starting material is consumed. The solvent is removed under reduced pressure and the residue purified by flash chromatography to give Compound 45.

Alternately, Compound 45 is obtained by heating Compound 48 in dry DMF in presence of 18-crown-6 (5 eq.) and KF (20 eq) at 110° C. followed by above work-up and flash chromatography.

Example 38

1-[2-fluoro-4-thio-β-D-ribofuranosyl]uracil (46)

Compound 45 is dissolved in 80% AcOH and stirred at room temperature for 10 h. The reaction mixture is concentrated under reduced pressure and co-evaporated twice with toluene. The residue is purified by flash chromatography to give Compound 46.

Example 39

5'-O-DMT-2'-fluoro-2'-deoxy-4'-thio-uridine

The title compound is prepared using the procedures illustrated above for Compound 14.

Example 40

1-(3-O-(2-Cyanoethoxy(diisopropylamino)phosphino)-5-O-(4,4'-dimethoxytrityl)-2-fluoro-2-deoxy)-4-thio-β-D-ribofuranosyl)uracil (49)

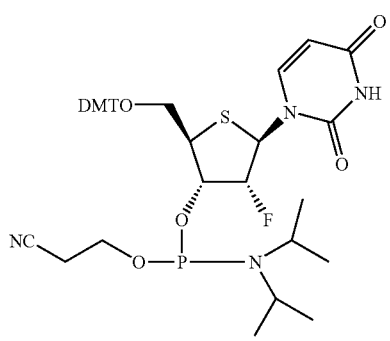

The title compound is prepared from 5'-O-DMT-2'-fluoro-2'-deoxy-4'-thio-uridine using the procedures illustrated above for Compound 16.

Example 41

5'-O-4,4'-Dimethoxytrityl)-2'-O-[2-(methoxy)ethyl] 4'-thiouridine-3'-[(2-cyanoethyl)-N,N-diisopropyl] phosphoramidite (53)

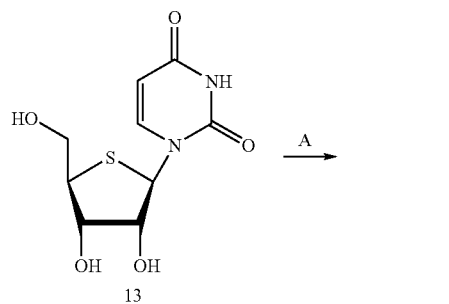

13

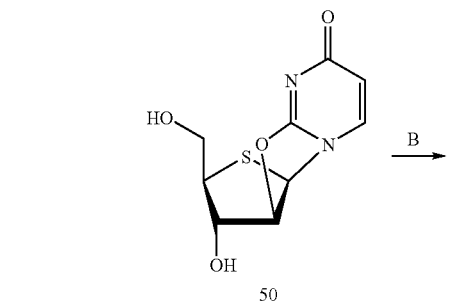

50

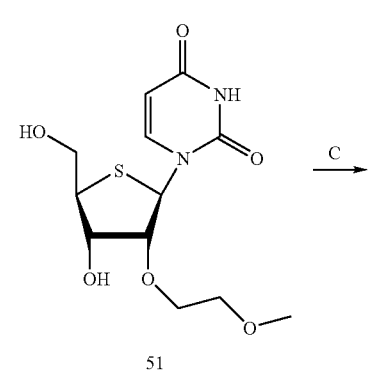

51

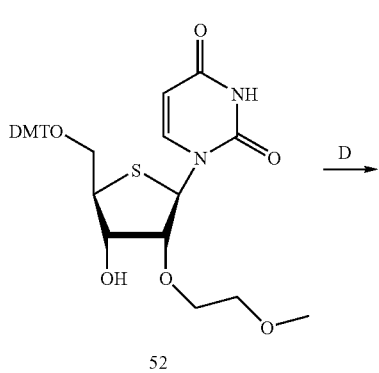

52

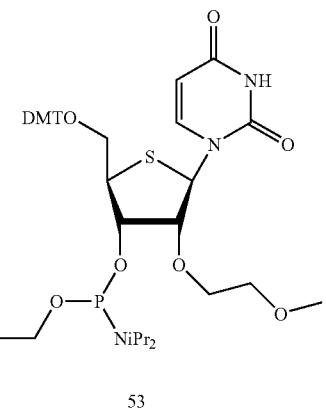

53

(A) (PhO)$_2$CO, NaHCO$_3$, DMA, 100 C.; (B) Al(OCH$_2$CH$_2$OMe)$_3$, reflux, 48 h; (C) DMTCl, DMAP, Pyridine, RT; (D) tetrazole, NMI, Phosphitylating reagent, DMF, RT.

Compound 13 is heated with diphenylcarbonate and sodium bicarbonate at 100° C. in dimethyl acetamide to yield Compound 50. Compound 50 on refluxing with anhydrous 2-methoxyethanol and aluminium 2-methoxyrthoxide will yield Compound 51. Compound 51 on selective tritylation at 5'-position with DMTCl and in pyridine in presence of catalytic amount of DMAP will yield Compound 52, which is phosphitylated at 3'-position to yield Compound 53.

Example 42

N$^4$-Benzoyl-5'-O-(4,4'-dimethoxytrityl)-2'-O-[2-(methoxy)ethyl]4'-thiocytidine-3'-[(2-cyanoethyl)-N,N-diisopropyl]phosphoramidite (56)

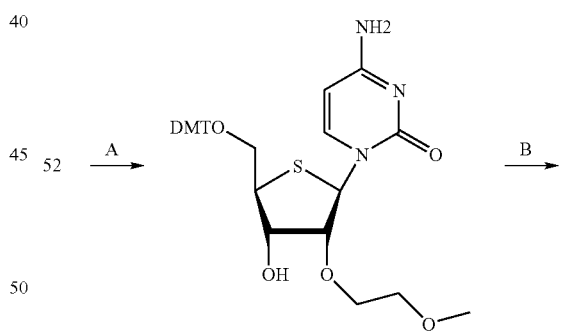

54

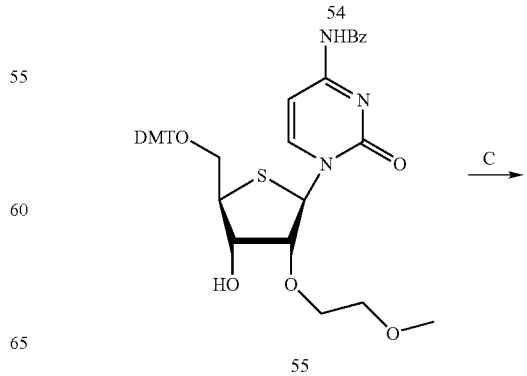

55

87

-continued

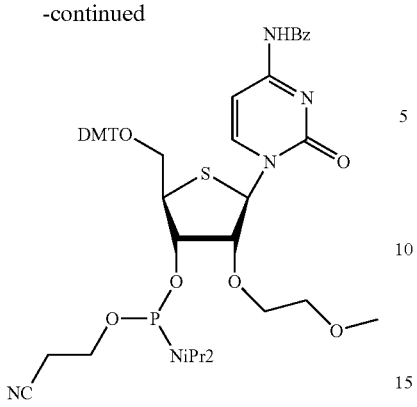

56

(A) TMSCl, pyridine, 1,2,4-triazole, POCl₃, Et₃N, CH₃CN, NH₄OH/dioxane; (B) DMF, benzoic anhydride, RT; (C) 1-H terarzole, NMI, phosphitylating reagent, DMF.

The 3'-hydroxyl group of Compound 52 is transiently protected with trimethylsilyl group on treatment with TMSCl in pyridine. This transiently protected compound is further treated with 1,2,4-triazole and POCl₃ in acetonitrile to give the triazole derivative at 4-position of the base. The triazolide is treated with ammonium hydroxide in dioxane to give Compound 54 which is converted to Compound 55 by treatment with benzoic anhydride in DMF at room temperature. Phosphitylation of Compound 55 will yield Compound 56.

Example 43

5'-O-(4,4'-Dimethoxytrityl)-2'-O-[2-(methoxy)ethyl]-$N^2$-isobutyryl-4'-thioguanosine-3'-[(2-cyanoethyl)-N,N-diisopropyl]phosphoramidite (66)

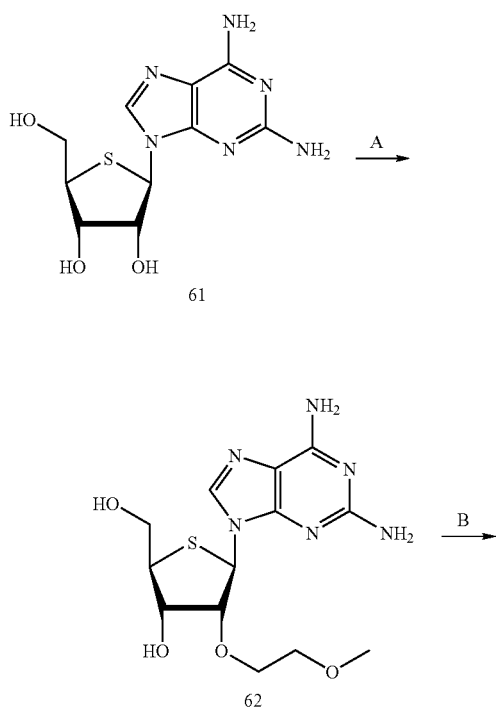

88

-continued

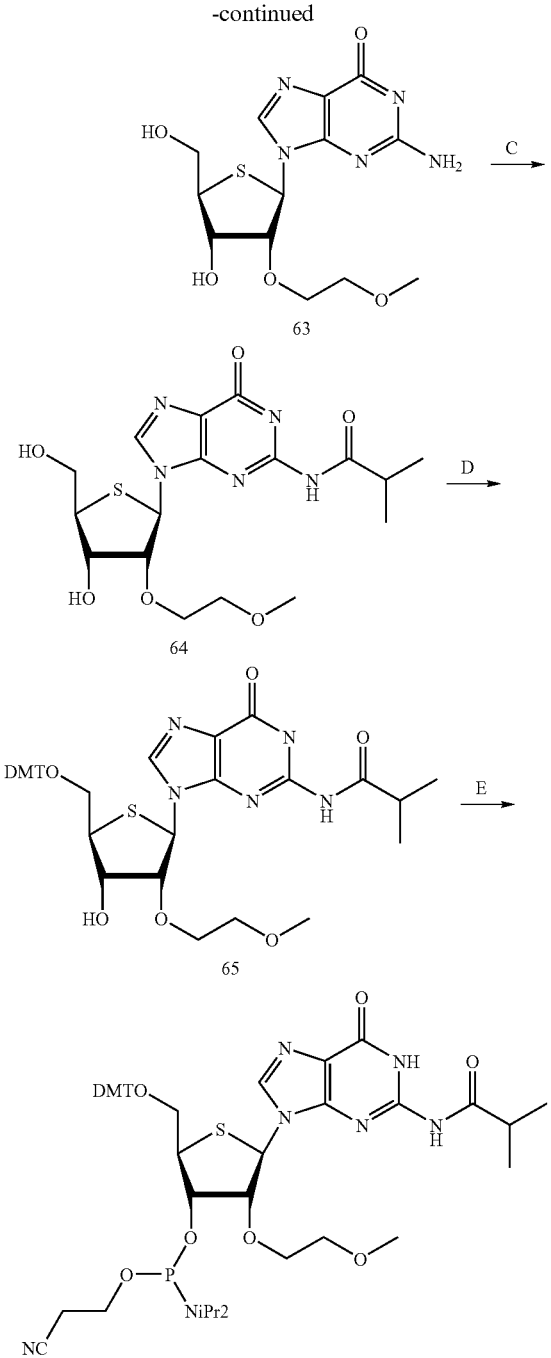

(A) CsCO₃, toluene-sulfonic acid-2-methoxy-ethyl ester, DMF; (B) adenosine deaminase, phosphate buffer, pH 7.5, RT; (C) TMSCl, pyridine, isobutyryl chloride followed by NH₄OH; (D) DMTCl, pyridine, DMAP; (E) 1-H tetrazole, NMI, DMF, 2-cyanoethyl-teraisopropylphosphoramidite, RT.

Synthesis of compound 66 is described in Scheme 13. Compound 61 on treatment with Cs₂CO₃, and toluene-4-sulfonic acid 2-methoxy-ethyl ester in DMF will give Compound 62. Treatment of Compound 62 with adenosine deaminase in phosphate buffer at pH 7.5 will yield Compound 63. The exocyclic amino group of Compound 63 is protected by treatment with isobutyryl group under transient protection conditions to yield Compound 64. Compound 64 is treated with DMTCl in pyridine at room temperature in the presence of catalytic amount of DMAP to yield Compound 65. Phosphitylation of Compound 65 will give Compound 66.

Example 44

5'-O-(4,4'-dimethoxytrityl)-3'-O-(tert-butyldimethylsilyl)-2'-O-succinyl-4'-thiouridine (67)

Compound 15b (0.26 g, 0.38 mmol) was mixed with succinic anhydride (0.06 g, 0.57 mmol) and DMAP (0.02 g, 0.2 mmol) and dried under reduced pressure at 40° C. overnight. The mixture was dissolved in anhydrous ClCH$_2$—CH$_2$Cl (1 mL) and triethyl amine (0.11 mL, 0.8 mmol) was added. The solution stirred at room temperature under argon atmosphere for 7 h. It was then diluted with CH$_2$Cl$_2$ (20 mL) and washed with ice cold aqueous citric acid (10 wt %, 20 mL) and brine (20 mL). The organic phase was dried over anhydrous Na$_2$SO$_4$ and concentrated to dryness. The residue thus obtained was purified by flash column chromatography on silica-gel. The column was eluted with 10% MeOH in CH$_2$Cl$_2$ to afford the title compound in 83% isolated yield (0.24 g): R$_f$ 0.1 (50% ethyl acetate in hexane).

$^1$H NMR (200 MHz, CDCl$_3$) δ 0.06 (s, 3H), 0.07 (s, 3H), 0.91 (s, 9H), 2.45-2.67 (m, 4H), 3.35-3.50 (m, 2H), 3.79 (s, 6H), 4.32 (d, J=3.2 Hz, 1H), 5.19 (dd, J=3.2 and 5.6 Hz, 1H), 5.55 (d, J=8.20 Hz, 1H), 6.45 (d, J=8.80 Hz, 4H), 6.84 (d, J=8.8 Hz, 1H), 7.23-7.45 (m, 9H), 7.59 (d, J=8.2 Hz, 1H), 10.12 (br s, 1H); $^{13}$C NMR (50 MHz, CDCl$_3$) δ −4.3, −4.8, 25.5, 28.5, 29.0, 55.1, 60.6, 60.3, 64.9, 73.6, 77.4, 87.2, 103.2, 113.2, 127.0, 127.9, 128.1, 130.1, 135.0, 135.3, 140.8, 144.2, 151.3, 158.6, 163.8, 171.3, 175.7; MS (FAB) m/z 799.20 [M+Na]$^+$.

Example 45

5'-O-(4,4'-dimethoxytrityl)-3'-O-(tert-butyldimethylsilyl)-4'-thiouridine-2'-O-succinyl CPG (68)

Compound 67 was loaded on to the aminoalkyl controlled pore glass (CPG) according to the standard synthetic procedure (TBTU mediated synthesis of functionalized CPG synthesis: Bayer, E.; Bleicher, K.; Maier, M. A.; Z. Naturforsch. 1995, 50b, 1096-1100) to yield the functionalized solid support 68 (49 µmol/g).

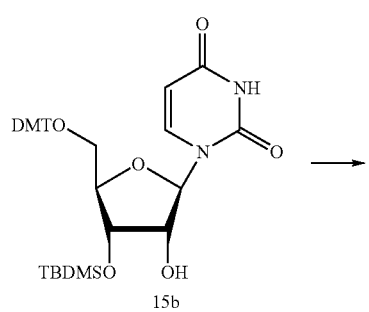

15b

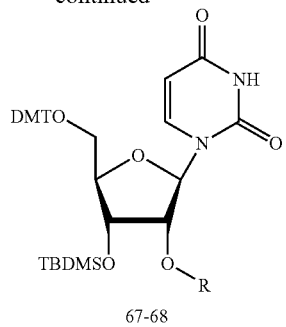

67-68

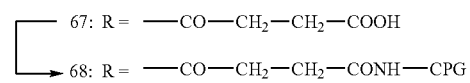

Example 46

5'-O-(4,4'-Dimethoxytrityl)-2'-O-[2-(methoxy)ethyl]-N$^6$-benzoyl-4'-thioadenosine-3'-[(2-cyanoethyl)-N,N-diisopropyl]phosphoramidite (69)

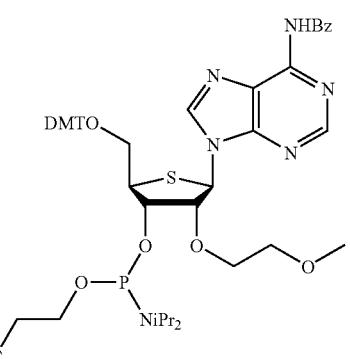

Compound 69 is prepared by first treating 4'-thioadenosine (Example 24) with Cs$_2$CO$_3$, and toluene-4-sulfonic acid 2-methoxy-ethyl ester in DMF to provide the 2'-O-methoxyethyl intermediate. This material is further transiently protected with TMSCl in pyridine and is further treated with benzoyl chloride to give the N6-Bz protected intermediate. The 5'-hydroxyl group of the N6-Bz protected intermediate is selectively protected using dimethoxytritylchloride. The DMT protected compound is phosphitylated under standard conditions using 2-cyanoethoxy-N,N,N',N'-tetraisopropylphosphoramidite as previously described as per example 16 above to give the title compound.

Example 47

4'-Thio Modified RNA Synthesis

Oligonucleotides with 4'-thio modifications were synthesized. 0.1 M solution of amidites in anhydrous acetonitrile was used for the synthesis of the modified oligonucleotides. The phosphoramidite solutions were delivered in two portions, each followed by a 5 min. coupling wait time. The standard 2'-O-TBDMS phosphoramidites and commercial solid supports (Glen Research Inc.) were used for the incorporation of A, C, G and U residues. Oxidation of the internucleotide phosphite triester to phosphate triester was carried out using tert-butylhydroperoxide/acetonitrile/water (10:87:3) with a wait time of 10 min. All other steps in the protocol supplied by Millipore were used without modifications. The coupling efficiencies were more than 97%. After completion of the synthesis, CPG was suspended in aqueous ammonium hydroxide (30 wt. %):ethanol (2:1) and kept at room temperature for 2 h. The CPG was filtered and the filtreate was heated at 55° C. for 6 h to complete the removal of all protecting groups except the TBDMS group at 2'-position. The residue obtained was re-suspended in anhydrous TEA.HF/NMP solution (1 mL of a solution of 1.5 mL N-methylpyrrolidine, 750 μl TEA and 1 ml of TEA3HF to provide a 1.4 M HF concentration) and heated at 65° C. for 1.5 h to remove the TBDMS groups at 2'-position. The reaction was quenched with 1.5 M ammonium bicarbonate (1 mL) and the mixture was loaded on to a Sephadex G-25 column (NAP Columns, Amersham Biosciences Inc.). The oligonucleotides were eluted with water and the fractions containing the oligonucleotides were pooled together and purified by High Performance Liquid Chromatography (HPLC, Waters, C-18, 7.8×300 mm, A=100 mM triethylammonium acetate, pH=7, B=acetonitrile, 5 to 20% B in 40 min, then 60% B in 60 min, Flow 2.5 mL min$^{-1}$, λ=260 nm). Fractions containing full-length oligonucleotides were pooled together (assessed by CGE analysis >90%) and evaporated. The residue was dissolved in sterile 10 M ammonium acetate (0.3 mL) solution. Ethanol (1 mL) was added and cooled to −78° C. for 1 h to get a precipitate and pelleted out the precipitate in a microfuge (NYCentrifuge 5415C; Eppendorf, Westbury, N.Y.) at 3000 rpm (735 g) for 15 min. The pellets were collected by decanting the supernatant. The pelleted oligonucleotides are dissolved in sterile water (0.3 mL) and precipitated by addition of ethanol (1 mL) and cooling the mixture at −78° C. for 1 h. The precipitate formed was pelleted out and collected as described above. The isolated yields for modified oligonucleotides were 30-35%. The oligonucleotides were characterized by ES MS analysis and purity was assessed by capillary gel electrophoresis and HPLC (Waters, C-18, 3.9×300 mm, A=100 mM triethylammonium acetate, pH=7, B=acetonitrile, 5 to 60% B in 40 min, Flow 1.5 mL min$^{-1}$, λ=260 nm).

Example 48

Synthesis of 2'-OMe-4'-thio-U phosphoramidite (40)

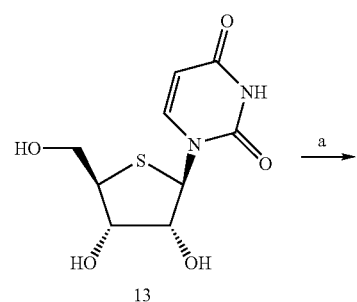

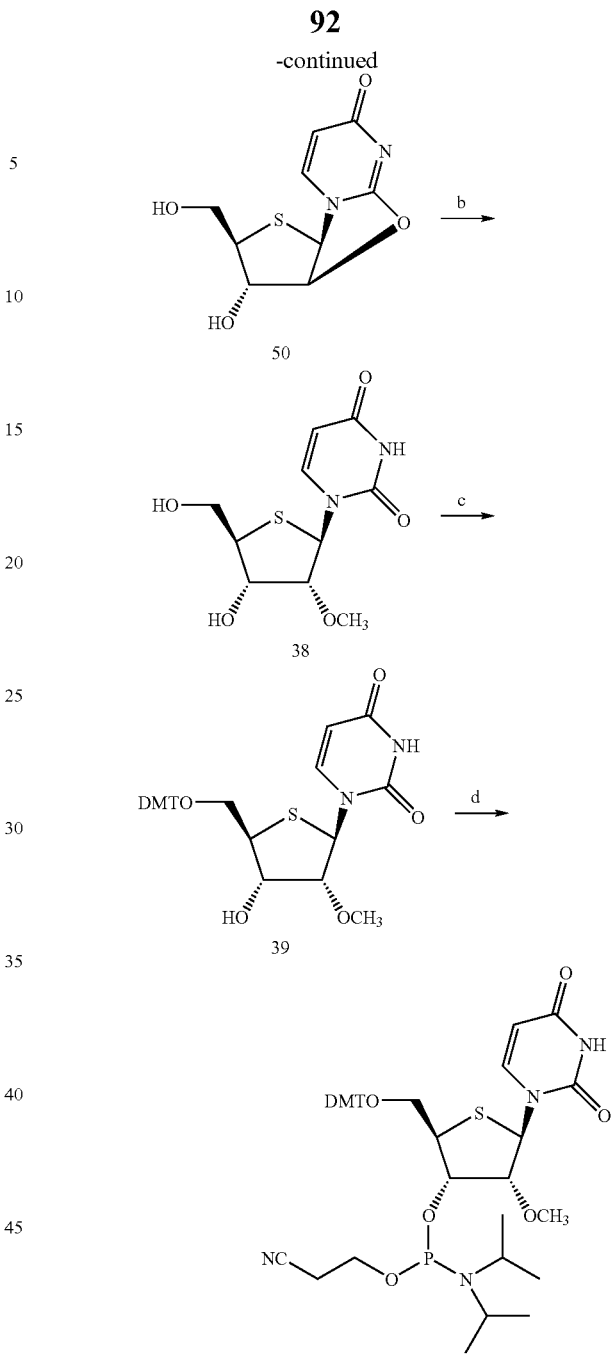

(A) Diphenyl carbonate, sodium bicarbonate, N,N-Dimethyl acetamide, heat; (b) Trimethyl borate, trimethyl orthoformate, sodium bicarbonate, methanol, heat; (c) 4,4'-Dimethoxytrityl chloride, pyridine, DMAP,; (d) 2-Cyanoethyl diisopropylchloro phosphoramidite, Diisopropylethylamine, methylene chloride 2,2'-Anhydro-4'-Thio-Uridine (50)

4'-Thio-uridine (13) (1 gm, 3.8 mmole), sodium bicarbonate (5 mg), diphenyl carbonate (900 mg, 4.0 mmol) were dissolved in 10 mL dry N,N-dimethylacetamide and heated at 100° C. for 2 hrs. The reaction mixture was cooled to room temperature and poured into rapidly stirring ether. The resulting precipitate was isolated by centrifugation (800 mg, 76% yield) and used as such in the next step. 1H NMR (DMSO-d6): δ 7.8 (d, 1H), 6.2 (d, 1H), 5.82 (m, 2H), 5.4 (d, 1H), 5.2 (m, 1H), 4.6 (m, 1H), 3.2-3.4 (m, 3H). ESMS=243 (MH$^+$), calc for $C_9H_{10}N_2O_4S$=242.03.

2'-O-methyl-4'-thio-Uridine (38)

Compound 50 (1 gm, 4.0 mmole), trimethyl borate (2 mL), trimethyl orthoformate (1 mL), sodium bicarbonate (5 mg) and methanol (3 mL) were added to a steel bomb and heated at 150° C. for 2 days. The bomb was cooled to room temperature and the residue was concentrated under reduced pressure and coevaporated several times with methanol. The residue was purified by flash chromatography (2% methanol in dichloromethane) to give 38 (800 mg, 75% yield). 1H NMR (DMSO-d6): δ 8.0 (d, 1H), 5.95 (d, 1H), 5.6 (d, 1H), 5.15-5.25 (br, 2H), 4.2 (m, 1H), 3.82 (m, 1H), 3.62 (m, 2H), 3.5 (s, 3H), 3.38 (m, 1H). ESMS=275 (MH$^+$), calc for C10H14N2O5S=274.06.

5'-(4,4'-dimethoxytrityl)-2'-O-methyl-4'-thio-uridine (39)

Compound 38 (400 mg, 1.46 mmole) was dissolved in cold, dry pyridine. Dimethoxytrityl chloride (600 mg, 1.752 mmole) was added and the mixture was stirred at room temperature for 24 hrs. Solvents were removed under reduced pressure and the residue was purified by flash chromatography (1:1 ethyl acetate: dichloromethane) to give 39 (600 mg, 75% yield). $^1$H NMR CDCl$_3$: δ 8.05 (d, 1H), 7.15-7.45 (m, 9H), 6.85 (m, 4H), 6.05 (d, 1H), 5.45 (d, 1H), 4.2 (br, 1H), 3.8 (s, 7H), 3.62 (m, 2H), 3.55 (s, 3H), 3.4 (br, 1H). FAB MS=577.2 (MH$^+$), calc for C31H32N2O7S=576.19.

3'-[(2-cyanoethyl)-N,N-diisopropylphosphoramidite]-5'-(4,4'-dimethoxytrityl)-2'-O-methyl-4'-thio-uridine (40)

Compound 39 (400 mg, 0.7 mmole) was treated with 2-cyanoethyl-N,N-diisopropyl chloro phosphoramidite (125 μL) and diisopropylethylamine (200 μL) in dry dichloromethane (5 mL) for 2 hrs at 0° C. The reaction mixture was separated between ethyl acetate (50 mL) and saturated sodium bicarbonate solution (20 mL). The ethyl acetate layer was washed twice with saturated sodium bicarbonate solution (20 mL), dried over anhydrous sodium sulfate and concentrated under reduced pressure. The residue was purified by flash chromatography (10% acetone in methylene chloride) to give 40 (400 mg, 60% yield). 1H NMR (CDCl3): δ 8.1 (d, 0.5H), 7.9 (d, 0.5H), 7.2-7.5 (m, 10H), 6.85 (m, 4H), 6.05 (dd, 1H), 5.55 (dd, 1H), 4.3 (m, 1H), 3.8 (m, 7H), 3.55 (m, 5H), 2.6 (m, 1.2H), 2.4 (m, 0.8H), 1.0-1.2 (m, 12H). FABMS=777.300 (MH$^+$), calc for C40H49N4O8PS=776.3009.

Example 49

Synthesis of 2'-OMe-4'-Thio-C Phosphoramidite

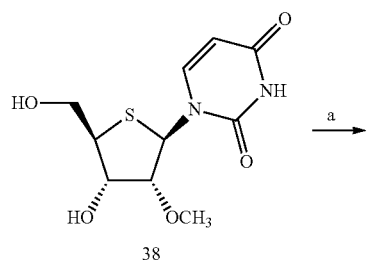

38

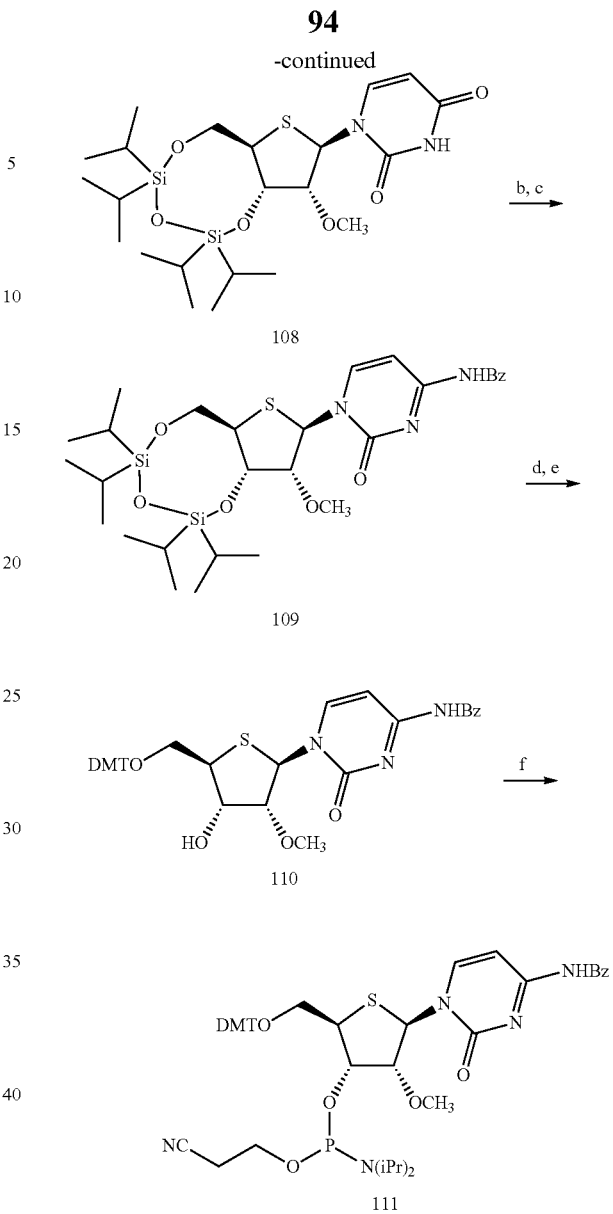

a) TIPDSCl$_2$, pyridine; b) POCl$_3$, TEA, CH$_2$CN, then 1,4-dioxane, NH$_4$OH; c) benzoic anhydride, DMAP, pyridine; d) TREAT•HF, TEA, THF; e) DMTr-Cl, DMAP, pyridine; f) 2-cyanoethyl diisopropylchlorophosphoramidite, diisopropylethylamine, methylene chloride Compound 38 (70 mg, 0.26 mmole) was dissolved in anhydrous pyridine (3 mL) under a nitrogen atmosphere and cooled in an ice bath. TIPDS-Cl$_2$ (166 μL, 0.52 mmole) was added drop-wise with vigorous stirring. Stirring was continued at the same temperature for an additional 2 to 4 h. When all of 38 had been consumed the reaction was quenched by pouring onto ice. The mixture was separated between ethyl acetate and water and the ethyl acetate layer was washed thrice with cold sat. sodium bicarbonate solution and once with brine. The ethyl acetate layer was dried over anhydrous sodium sulfate and concentrated under reduced pressure. The crude material was purified by flash chromatography (5% methanol in dichloromethane) to give Compound 108 (120 mg, 90% yield). 1H NMR (CDCl3): δ 8.02 (d, 1H), 6.02 (d, 1H), 5.6 (d, 1H), 4.2 (br, 1H), 3.62 (m, 3H), 3.55 (s, 3H), 3.4 (br, 1H), 1.1-0.9 (m, 28H). ESMS=517 (MH$^+$), calc for C$_{22}$H$_{40}$N$_2$O$_6$SSi$_2$=516.02.

1-[3,5-O-(1,1,3,3-tetraisopropyldisiloxane-1,3-diyl)-2-O-methyl-4-thio-β-D-ribofuranosyl]-N-benzoyl-cytosine (109)

Compound 108 (475 mg, 0.92 mmole) was dissolved in dry acetonitrile (4 mL). In a separate flask 1,2,4-triazole (0.89 g, 12.88 mmole) was suspended in dry acetonitrile (12 mL), under nitrogen and cooled to 0° C. in an ice-bath. POCl$_3$ (0.33 mL, 3.68 mmole) was added dropwise with vigorous stirring, followed by dropwise addition of TEA (2.6 mL, 18.4 mmole) in acetonitrile (6 mL). After TEA addition was complete the reaction mixture was stirred at the same temperature for an additional 30 min. The solution of 108 was added and the reaction stirred at 0° C. for 1 hr. and then at room temperature for 12 hrs. At the end of this period the crude reaction was separated between ethyl acetate and sat. bicarbonate solution. The ethyl acetate layer was washed twice with sat. sodium bicarbonate solution and once with brine. After drying over anhydrous sodium sulfate the solvents were removed under reduced pressure. The resulting oily residue was taken up in 1,4-dioxane (10 mL) and aqueous ammonia solution (5 mL) was added. The reaction was stirred in a sealed flask for 12 hrs. The reaction mixture was separated between ethyl acetate and water. The ethyl acetate layer was washed twice with water and once with brine, dried over anhydrous sodium sulfate, and concentration under reduced pressure. The resulting crude residue was dissolved in dry acetonitrile (220 mg, 0.43 mmole). Dimethylaminopyridine (DMAP) (55 mg, 0.43 mmole) and benzoic anhydride (150 mg, 0.853 mmole) were added and the reaction was stirred at 65° C. for 20 min. The reaction was partitioned between ethyl acetate and water and the ethyl acetate layer was washed thrice with sat. sodium bicarbonate solution, once with brine, and dried over anhydrous sodium sulfate. Solvents were removed under reduced pressure and the residue was purified by flash chromatography (50% ethyl acetate in dichloromethane) to give Compound 109 (480 mg, 85% yield). 1H NMR (CDCl3): δ 8.9 (d, 1H), 8.7 (br s, 1H), 7.9 (d, 2H), 7.5 (m, 3H), 5.96 (s, 1H), 4.15 (m, 3H), 3.85 (m, 5H), 1.15-0.8 (m, 28H). ESMS=620 (MH$^+$) calc for C$_{29}$H$_{45}$N$_3$O$_6$SSi$_2$=619.2.

1-[5-(4,4'-dimethoxytrityl)-2-O-methyl-4-thio-β-D-ribofuranosyl]-N-benzoyl-cytosine (110)

Compound 109 (200 mg, 0.32 mmole) was dissolved in dry THF. TREAT.HF (1.5 mL) and TEA (0.75 mL) were added and the mixture stirred for 4 hrs. The solvent was removed under reduced pressure followed by two co-evaporations with dry toluene. The residue was further coevaporated twice with anhydrous pyridine (10 mL) and dried overnight over phosphorous pentoxide. The residue was dissolved in cold, dry pyridine (5 mL). DMAP (8 mg, 0.07 mmole) and dimethoxytrityl chloride (200 mg, 0.6 mmole) were added and the mixture was stirred at room temperature for 24 hrs. The residue purified by flash chromatography (10% methanol in dichloromethane) to give Compound 110 (180 mg, 80% yield). 1H NMR (CDCl3): δ 8.8 (d, 1H), 8.6 (d, 1H), 7.9 (d, 2H), 7.6-7.2 (m, 13H), 6.9 (d, 4H), 6.15 (s, 1H), 4.2 (br, 1H), 3.8 (s, 6H), 3.76 (m, 1H), 3.73 (s, 3H), 3.66 (m, 3H). FABMS=680.2 (MH$^+$), cal for C$_{38}$H$_{37}$N$_3$O$_7$S=679.235.

3'-[(2-cyanoethyl)-N,N-diisopropylphosphoramidite]-5'-(4,4'-dimethoxytrityl)-2'-O-methyl-4'-thio-N-benzoyl-cytidine (111)

Compound 110 (190 mg) was treated with 2-cyanoethyl-N,N-diisopropyl chloro phosphoramidite (125 μL) and diisopropylethylamine (200 μL) in dry dichloromethane (5 mL) for 2 hrs at 0° C. The reaction mixture was separated between ethyl acetate (50 mL) and saturated sodium bicarbonate solution (20 mL). The ethyl acetate layer was washed twice with saturated sodium bicarbonate solution (20 mL), dried over anhydrous sodium sulfate and concentrated under reduced pressure. The residue was purified by flash chromatography (30% ethyl acetate in hexanes) to give 113 (150 mg, 75% yield). 1H NMR (CDCl$_3$): δ 8.8 (d, 0.5H), 8.6 (d, 0.5H), 7.9 (d, 2H), 6.9 d(4H), 7.6-7.2 (15H), 6.1 (d, 1H), 4.4 (m, 0.5H), 4.2 (m, 0.5H), 3.9 (m, 1H), 3.8 (d, 6H), 3.7-3.3 (m, 7H), 2.55 (m, 0.5H), 2.4 (m, 0.5H), 1.3-1.0 (m, 12H). FABMS=880.3 (MH$^+$), calc for C$_{47}$H$_{54}$N$_5$O$_8$PS=879.3431.

Example 50

Synthesis of 2'-O-methyl-4'-thio-modified siRNA

The standard phosphoramidites and solid supports were used for incorporation of A, U, G, and C residues. A 0.1 M solution of the amidites in anhydrous acetonitrile was used for the synthesis. Chemical phosphorylation reagent procured form Glen Research Inc., Virginia, USA was used to phosphorylate the 5'-terminus of modified oligonucleotides. The modified oligonucleotides were synthesized on functionalized controlled pore glass (CPG) on an automated solid phase DNA synthesizer. The universal solid support was used for the synthesis of oligonucleotides bearing a terminal 2'-deoxy-2'-fluoro modification.[43] Twelve equivalents of phosphoramidite solutions were delivered in two portions, each followed by a 6 min coupling wait time. All other steps in the protocol supplied by the manufacturer were used without modification. A solution of tert-butyl hydroperoxide/acetonitrile/water (10:87:3) was used to oxidize inter nucleosidic phosphite to phosphate. The coupling efficiencies were more than 97%. After completion of the synthesis, solid support was suspended in aqueous ammonium hydroxide (30 wt. %): ethanol (3:1) and heated at 55° C. for 6 h to complete the removal of all protecting groups except TBDMS group at 2'-position. The solid support was filtered and the filtrate was concentrated to dryness. The residue obtained was re-suspended in anhydrous triethylamine trihydrofluoride/triethylamine/1-methyl-2-pyrrolidinone solution (0.75 mL of a solution of 1 ml of triethyl amine trihydofluoride, 750 μl triethylamine and 1.5 mL 1-methyl-2-pyrrolidine, to provide a 1.4 M HF concentration) and heated at 65° C. for 1.5 h to remove the TBDMS groups at the 2'-position.[37] The reaction was quenched with 1.5 M ammonium bicarbonate (0.75 mL) and the mixture was loaded on to a Sephadex G-25 column (NAP Columns, Amersham Biosciences Inc.). The oligonucleotides were eluted with water and the fractions containing the oligonucleotides were pooled together and purified by High Performance Liquid Chromatography (HPLC) on a strong anion exchange column (Mono Q, Pharmacia Biotech, 16/10, 20 mL, 10 μm, ionic capacity 0.27-0.37 mmol/mL, A=100 mM ammonium acetate, 30% aqueous acetonitrile, B=1.5 M NaBr in A, 0 to 60% B in 40 min, Flow 1.5 mL min$^{-1}$, λ=260 nm). Fractions containing full-length oligonucleotides were pooled together (assessed by CGE analysis >90%) and evaporated. The residue was dissolved in sterile water (0.3 mL) and absolute ethanol (1 mL) was added and cooled in dry ice (−78° C.) for 1 h and the precipitate formed was pelleted out by centrifugation (NYCentrifuge 5415C; Eppendorf, Westbury, N.Y.) at 3000 rpm (735 g). The supernatant was decanted and the pellet was re-dissolved in 10 M ammonium acetate (0.3 mL) solution. Ethanol (1 mL) was added and cooled to −78° C. for 1 h to get a precipitate and pelleted out the precipitate in a centrifuge (NYCentrifuge 5415C; Eppendorf, Westbury, N.Y.) at 3000-rpm (735 g) for 15 min. The pellet was collected by decanting the supernatant. Re-dissolved the pelleted oligonucleotides in sterile water (0.3 mL) and precipitated by adding ethanol (1 mL) and cooling the mixture at −78° C. for 1 h. The precipitate formed was pelleted out and collected as described above. The oligonucleotides were characterized by ES MS and purity was assessed by capillary gel electrophoresis and HPLC (Waters, C-18, 3.9×300 mm, A=100 mM triethylammonium acetate, pH=7, B=acetonitrile, 5 to 60% B in 40 min, Flow 1.5 mL min$^{-1}$, λ=260 nm).

TABLE 2

2'-O-methyl-4'-thio modified antisense strand of SiRNA targeted to PTEN mRNA

| ISIS No. | Construct | Cald Mass | Found Mass |
|---|---|---|---|
| 375762 | 3'-UU*CAUUC*CUGGUCUCUG⁹UU-5' | 5995.01 | 5994.40 |
| 375761 | 3'-U*U*C*AUUCCUGGUCUCUGU^σU^σ-5' | 6013.01 | 6012.01 |

U* = 2'-O-methyl-4'-thiouridine, C* = 2'-O-methyl-4'-thiocytidine, G9 = 2'-O-methyl guanosine, U^σ = 4'-thiouridine

Example 51

Synthesis of 2'-O-(2-Methoxyethyl)-4'-thio-uridine

4'-thio-uridine —(i)→

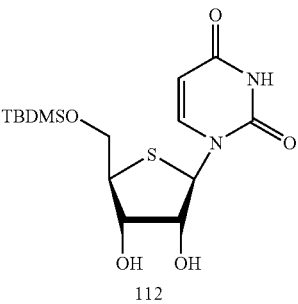

112

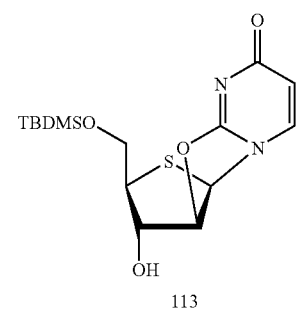

113

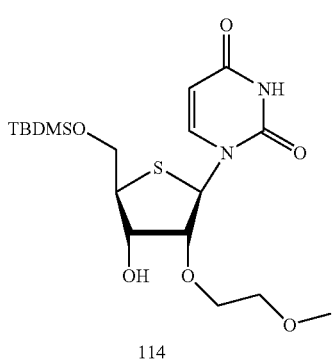

114

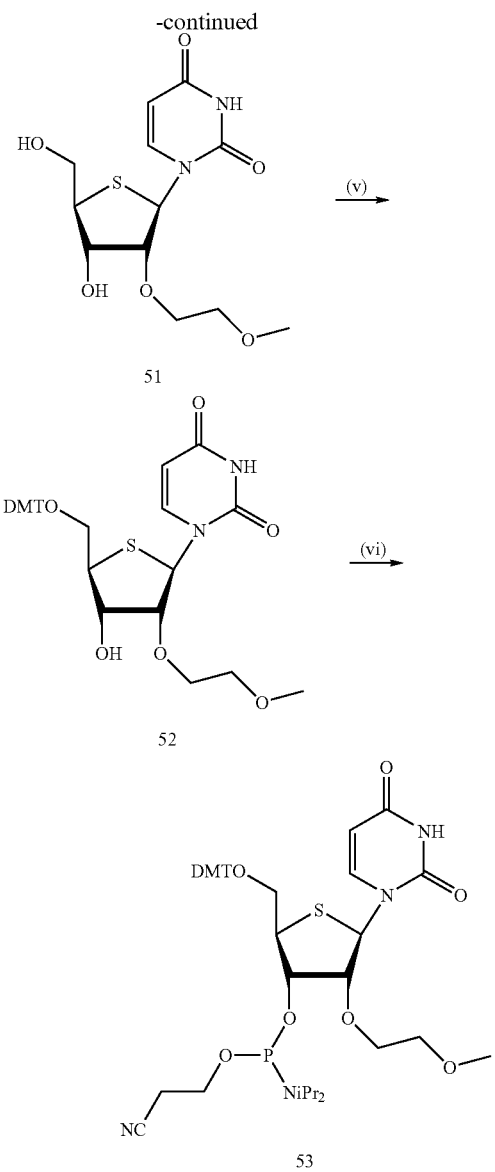

$^a$(i) TBDPSCl, Py, rt, 91% (ii) (PhO)$_2$CO, NaHCO$_3$, DMA, 100° C., 80%; (iii) B(OCH$_2$CH$_2$OMe)$_3$, HOCH$_2$CH$_2$OMe, reflux, 21 h, 63%, (iv) 1M TBAF in THF, THF, acetic acid, (iV) DMTCl, DMAP, Py, rt, 60%, 2-Cyanoethyl diisopropylchlorophosphoramidite, Diisopropylethylamine, methylene chloride 5'-O-tert-butyldiphenylsilyl-4-thiouridine (112)

4'-thio-uridine (2.95 g, 11.43 mmol) was mixed with DMAP (0.02 g, 0.15 mmol) and dried under reduced pressure over P$_2$O$_5$. The reaction mixture was dissolved in anhydrous pyridine (15 mL) and tert.-butyldiphenylsilyl chloride (3.27 mL, 13 mmol) was added. Stirred the reaction mixture at room temperature under argon atmosphere for 12 h. The solvent was removed under reduced pressure residue dissolved in ethyl acetate (100 mL). The organic phase washed with aqueous NaHCO$_3$ (5%, 50 mL), brine (50 mL). Organic layer separated and dried over anhydrous Na2SO4 and concentrated under reduced pressure. The residue obtained was purified by flash silica gel column chromatography and eluted with dichloromethane containing in cremental amount odf methanol (5-10%) to yield Compound 112 (5.21 g, 91%) as a foam. $^1$H NMR (200 MHz, DMSO-d$_6$): 11.33 (s, 1H), 7.84 (d, J=8.2 Hz, 1H,), 7.66-7.33 (m, 10H), 5.86 (d, J=6.4 Hz, 1H), 5.58 (d, J=5.6 Hz, 1H), 5.47 (d, J=8.2 Hz, 1 H), 5.34 (d, J=4.4 Hz, 1H), 4.09 (m, 2H), 3.97 (m, 1H), 3.77 (m, 1H), 3.35 (m, 1H), 1.01 (s, 9H); MS (API-ES) m/z 499.1 [M+H]$^+$.

2,2'-Anhydro-5'-O-tert-butyldiphenylsilyl-4'-thio-uridine (113)

To a dried mixture of Compound 112 (1.1 g, 2.20 mmol), diphenylcarbonate (0.55 g, 2.42 mmol) and anhydrous NaHCO$_3$ (73.7 mg, 0.88 mmol) dimethyl acetamide (5.5 mL) was added. The reaction mixture was heated at 100° C. 5 h. The solvent was distilled out under reduced pressure to get an oils and the oil was purified by falsh silica gel column chromatography and eluted with 5 to 10% MeOH in dichloromethane to yield Compound 113 (0.87 g, 82%). $^1$H NMR (200 MHz, DMSO-d$_6$): 7.81 (d, J=7.4 Hz, 1H,), 7.57-7.34 (m, 10H), 6.19 (d, J=7.4 Hz, 1H), 5.98 (d, J=4.4 Hz, 1H), 5.39 (d, 1H), 5.58 (d, J=5.6 Hz, 1H), 4.76 (br s, 1 H), 3.40-3.7 (m, 3H), 1.00 (s, 9H); MS (API-ES) m/z 481.1 [M+H]$^+$.

5'-O-tert-Butyldiphenylsilyl-2'-O-(2-methoxyethyl)-4'-thio-uridine (114)

Compound 113 (0.7 g, 1.45 mmol) was mixed with tris(2-methoxyethyl)borate (0.63 g, 2.93 mmol), NaHCO$_3$ (0.02 g, 0.23 mmol) and 2-methoxyethanol (7 mL). The mixture was heated at 140° C. for 21 h. The solvent was removed under reduced pressure and to the residue water (5 mL) and concentrated the solvent on a rotavapour keeping water bath temperature 50-60° C. Repeated this process twice. Residue obtained was purified by falsh silica gel column chromatography and eluted with 5% MeOH in CH$_2$Cl$_2$ to yield Compound 114 (0.51 g, 66%0 as a foam. $^1$H NMR (200 MHz, DMSO-d$_6$): 11.38 (s, 1 H), 7.89 (d, 1H,), 7.67-7.44 (m, 10H), 5.92 (d, 1H), 5.69 (d, 1H), 5.46 (d, 1H), 5.30 (d, 1H), 4.17 (m, 1 H), 4.01-3.94 (m, 2H), 3.82 (m, 1H), 3.58 (m, 1H), 3.52-3.38 (m, 4H), 3.20 (s, 3H), 1.01 (s, 9H); MS (API-ES) m/z 579.1 [M+Na]$^+$.

2'-O-(2-Methoxyethyl)-4'-thio-uridine (51)

To a solution of Compound 114 (0.49 g, 0.88 mmol) in anhydrous THF (37 mL) 1M tetrabutylammonium fluoride in THF (1.8 mL) was added. Acetic acid (0.12 mL, 2.03 mmol) was added to this mixture and the resulting reaction mixture stirred at room temperature for 30 min. The solvent was removed under reduced pressure and the residue obtained was purified by flash silica gel column chromatography and eluted with acetone to yield Compound 51 (0.23 g, 83%). $^1$H NMR (300 MHz, DMSO-d$_6$): 11.2 (s, 1 H), 8.04 (d, 1H,), 5.94 (d, 1H), 5.69 (d, 1H), 5.20 (d, 1H), 4.15 (t, 1H), 4.04 (m, 1H), 3.67-3.53 (m, 6 H), 3.47-3.36 (m, 2H), 3.31 (s, 3H); MS (API-ES) m/z 341.0 [M+Na]$^+$.

2'-O-(2-Methoxyethyl)-4'-thio-uridine (52)

Compound 51 (0.27, 0.85 mmol) was mixed with DMAP (0.05 g, 0.43 mmol) and dried under reduced pressure. The mixture was dissolved in anhydrous pyridine and 4,4'-dimethoxytrityl chloride (0.36 g, 1.06 mmol) was added and the resulting solution stirred at room temperature under inert atmosphere for 20 h. Solvent was removed under reduced pressure and the residue obtained was dissolved in dichloromethane (50 ml) and washed with aqueous NaHCO$_3$ (5 wt %, 40 mL) and brine (40 mL). The organic phase dried over anhydrous Na$_2$SO$_4$ and evaporated under reduced pressure. The residue obtained was purified by flash silica gel column chromatography and eluted with 0-5% MeOH in CH$_2$Cl$_2$ to yield Compound 52 (0.32 g, 61%). $^1$H NMR (200 MHz, DMSO-d$_6$): 11.39 (s, 1H), 7.76 (d, 1H), 7.74-7.15 (m, 9H) 6.90 (d, 4H), 5.89 (d, 1H), 5.50 (dd, 1H), 5.25 (d, 1H), 4.05 (m, 1H), 3.88 (m, 1H), 3.73 (s, 6 H), 3.53 (m, 1H), 3.48-3.53 (m, 5H), 3.18 (s, 3 H); MS (API-ES) m/z 643.2 [M+Na]$^+$.

Example 52

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy(2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 53

Oligonucleotide and Oligonucleoside Synthesis

The antisense oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 54

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate (S$_2$Na$_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., J. Am. Chem. Soc., 1998, 120, 11820-11821; Matteucci, M. D. and Caruthers, M. H. J. Am. Chem. Soc., 1981, 103, 3185-3191; Beaucage, S. L. and Caruthers, M. H. Tetrahedron Lett., 1981, 22, 1859-1862; Dahl, B. J., et al., Acta Chem. Scand,. 1990, 44, 639-641; Reddy, M. P., et al., Tetrahedrom Lett., 1994, 25, 4311-4314; Wincott, F. et al., Nucleic Acids Res., 1995, 23, 2677-2684; Griffin, B. E., et al., Tetrahedron, 1967, 23, 2301-2313; Griffin, B. E., et al., Tetrahedron, 1967, 23, 2315-2331).

RNA antisense oligomeric compounds (RNA oligonucleotides) of the present invention can be synthesized by the methods herein or purchased from Dharmacon Research, Inc (Lafayette, Colo.). Once synthesized, complementary RNA antisense oligomeric compounds can then be annealed by methods known in the art to form double stranded (duplexed) antisense oligomeric compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense oligomeric compounds can be used in kits, assays, screens, or other methods to investigate the role of a target nucleic acid.

Example 55

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 56

Design and Screening of Duplexed Antisense Oligomeric Compounds Directed to a Selected Target In accordance with the present invention, a series of nucleic acid duplexes comprising the antisense oligomeric compounds of the present invention and their complements can be designed to target a target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

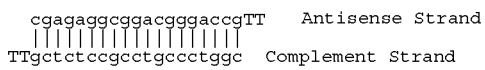

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligomeric compounds are evaluated for their ability to modulate a target expression.

When cells reached 80% confluency, they are treated with duplexed antisense oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

Example 57

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 58

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 59

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

Example 60

Cell Culture and Oligonucleotide Treatment

The effect of antisense oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide. A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier. HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Oligomeric Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO:5) which is targeted to human H-ras, or ISIS 18078, (GTGCGCGCGAGCCCGAAATC, SEQ ID NO:6) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO:7, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 61

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently desired. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 62

Design of Phenotypic Assays and In Vivo Studies for the Use of a Target Inhibitors Phenotypic Assays Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements. Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the a target inhibitor show positive trends in their disease state or condition index at the conclusion of the study.

Example 63

RNA Isolation

Poly(A)+ mRNA Isolation

Poly(A)+ mRNA was isolated according to Miura et al., (Clin. Chem., 1996, 42, 1758-1764). Other methods for poly (A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 64

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 mL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and are designed to hybridize to a human a target sequence, using published sequence information.

Example 65

Northern Blot Analysis of a Target mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 66

Antisense Inhibition of Human a Target Expression by Oligonucleotides

In accordance with the present invention, a series of oligomeric compounds are designed to target different regions of the human target RNA. The oligomeric compounds are analyzed for their effect on human target mRNA levels by quantitative real-time PCR as described in other examples herein. Data are averages from three experiments. The target regions to which these sequences are complementary are herein referred to as "suitable target segments" and are therefore suitable for targeting by oligomeric compounds of the present invention. The sequences represent the reverse complement of the suitable antisense oligomeric compounds.

As these "suitable target segments" have been found by experimentation to be open to, and accessible for, hybridization with the antisense oligomeric compounds of the present invention, one of skill in the art will recognize or be able to ascertain, using no more than routine experimentation, further embodiments of the invention that encompass other oligomeric compounds that specifically hybridize to these suitable target segments and consequently inhibit the expression of a target.

According to the present invention, antisense oligomeric compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 67

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Although the invention has been described in detail with respect to various preferred embodiments it is not intended to be limited thereto, but rather those skilled in the art will recognize that variations and modifications may be made therein which are within the spirit of the invention and the scope of the appended claims.

All publications, patents, published patent applications, and other references mentioned herein are hereby incorporated by reference in their entirety.

What is claimed is:

1. An oligomeric compound having at least one 4'-thionucleoside of formula IIa:

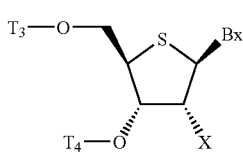

wherein, independently, for each 4'-thionucleoside of formula IIa:
one of $T_3$ and $T_4$ is an internucleoside linking group linking the 4'-thionucleoside of formula IIa to the oligomeric compound and the other of $T_3$ and $T_4$ is H, a protecting group, a conjugate group or an internucleoside linking group linking the 4'-thionucleoside of formula IIa to the oligomeric compound;

Bx is hydrogen or a nucleobase;

X is fluoro, substituted or unsubstituted O—$C_1$-$C_{12}$ alkyl, substituted or unsubstituted O—$C_2$-$C_{12}$ alkenyl, or substituted or unsubstituted O—$C_2$-$C_{12}$ alkynyl.

2. The oligomeric compound of claim 1, wherein X is a group of formula Ia or Ib:

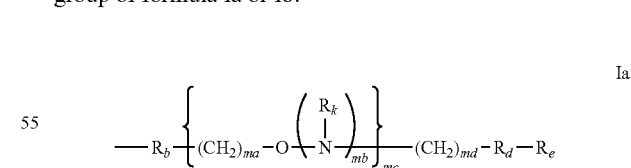

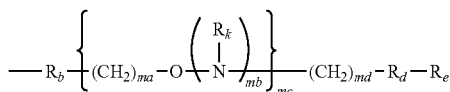

wherein:

$R_b$ is O;

$R_d$ is a single bond, O, S or C(=O);

$R_e$ is $C_1$-$C_{10}$ alkyl, $N(R_k)(R_m)$, $N(R_k)(R_n)$, $N=C(R_p)(R_q)$, $N=C(R_p)(R')$ or has formula Ic;

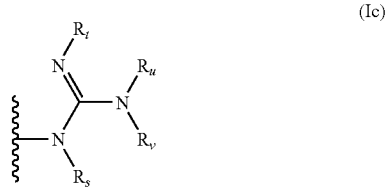

(Ic)

$R_p$, and $R_q$ are each independently hydrogen or $C_1$-$C_{10}$ alkyl;

$R_r$ is $R_x$-$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{13}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, an amino protecting group or $R_x$-$R_y$;

$R_p$ is hydrogen, an amino protecting group or $R_x$-$R_y$;

$R_x$ is a bond or a linking moiety;

$R_y$ is a chemical functional group, a conjugate group or a solid support medium;

each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are an amino protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

3. The oligomeric compound of claim 1, wherein at least one of $T_3$ or $T_4$ is a phosphodiester internucleoside linkage.

4. The oligomeric compound of claim 3, wherein each internucleoside linkage is a phosphodiester internucleoside linkage.

5. The oligomeric compound of claim 1, wherein at least one of $T_3$ or $T_4$ is a phosphorothioate internucleoside linkage.

6. The oligomeric compound of claim 5, wherein each internucleoside linkage is a phosphorothioate internucleoside linkage.

7. The oligomeric compound of claim 1, wherein X is selected from fluoro or substituted or unsubstituted O—$C_1$-$C_{12}$ alkyl.

8. The oligomeric compound of claim 1, wherein X is fluoro.

9. The oligomeric compound of claim 1, wherein X is O—$CH_3$.

10. The oligomeric compound of claim 1, wherein X is O—$CH_2CH_2$—O—$CH_3$.

11. The oligomeric compound of claim 1, wherein X is O-allyl, O—$(CH_2)_{ma}$—O—$N(R_m)(R_n)$ or O—$CH_2$—C(=O)—$N(R_m)(R_n)$;

wherein:

each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl; and ma is from 1 to about 10.

12. The oligomeric compound of claim 1 wherein each X is identical for each 4'-thionucleoside of formula IIa.

13. The oligomeric compound of claim 1 comprising between 8 and 80 nucleosides.

14. The oligomeric compound of claim 1 comprising between 8 and 50 nucleosides.

15. The oligomeric compound of claim 1 comprising between 8 and 30 nucleosides.

16. The oligomeric compound of claim 1 comprising between 10 and 30 nucleosides.

17. The oligomeric compound of claim 1 comprising between 15 and 30 nucleosides.

18. The oligomeric compound of claim 1 comprising between 15 and 25 nucleosides.

19. The oligomeric compound of claim 1 comprising a plurality of ribonucleosides.

20. The oligomeric compound of claim 1 wherein each nucleoside that is not a 4'-thionucleoside of formula IIa is a ribonucleoside.

* * * * *

```
                        SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 1
cgagaggcgg acgggaccg                                                  19

<210> SEQ ID NO 2
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 2
cgagaggcgg acgggaccgt t                                               21

<210> SEQ ID NO 3
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 3
ttgctctccg cctgccctgg c                                               21

<210> SEQ ID NO 4

<400> SEQUENCE: 4

000

<210> SEQ ID NO 5
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 5
```

```
tccgtcatcg ctcctcaggg                                              20

<210> SEQ ID NO 6
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 6
gtgcgcgcga gcccgaaatc                                              20

<210> SEQ ID NO 7
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 7
atgcattctg cccccaagga                                              20

<210> SEQ ID NO 8
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 8
aagtaaggac cagagacaa                                               19

<210> SEQ ID NO 9
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 9
ttgtctctgg tccttactt                                               19
```